(12) United States Patent
Rullo et al.

(10) Patent No.: US 11,827,624 B2
(45) Date of Patent: Nov. 28, 2023

(54) COVALENT IMMUNE RECRUITER COMPOUNDS FOR IMMUNE CELL RECOGNITION AND ASSOCIATED USES

(71) Applicant: McMaster University, Hamilton (CA)

(72) Inventors: Anthony Rullo, Hamilton (CA); Benjamin Lake, Ancaster (CA); Nickolas Semiuck, Oakville (CA)

(73) Assignee: MCMASTER UNIVERSITY, Hamilton (CA)

( * ) Notice: Subject to any disclaimer, the term of this patent is extended or adjusted under 35 U.S.C. 154(b) by 7 days.

(21) Appl. No.: 17/249,332

(22) Filed: Feb. 26, 2021

(65) Prior Publication Data

US 2021/0276981 A1 Sep. 9, 2021

Related U.S. Application Data

(60) Provisional application No. 62/981,767, filed on Feb. 26, 2020.

(51) Int. Cl.
*C07D 403/12* (2006.01)
*C07D 233/90* (2006.01)
*C07D 493/10* (2006.01)
*C07K 16/44* (2006.01)

(52) U.S. Cl.
CPC ......... *C07D 403/12* (2013.01); *C07D 233/90* (2013.01); *C07D 493/10* (2013.01); *C07K 16/44* (2013.01)

(58) Field of Classification Search
CPC ... C07D 233/90; C07D 403/12; C07D 493/10
See application file for complete search history.

(56) References Cited

U.S. PATENT DOCUMENTS 9,296,708 B2 3/2016 Spiegel et al.

OTHER PUBLICATIONS

Abstract "Covalent Dimerizers, A New Tool in Tumor Immunotherapy", Symposium: (BM Division—Chemical Biology Applications in Molecules, Cells, and Disease; Affiliation: Academia—Undergraduate Student, Jun. 5, 2019.
Abstract "Chemical Strategies To Modulate The Immune Recognition of Cancer (CSC181712)", Symposium: Early Career Investigators—joint BM, IC, OR; Division: Biological and Medicinal Chemistry (BM), May 27-31, 2018.
Lake et al., "Covalent Immune Recruiters: Tools to Gain Chemical Control Over Immune Recognition", ACS Chem. Biol. Feb. 26, 2020, 15, 4, 1089-1095.

*Primary Examiner* — Shawquia Jackson
(74) *Attorney, Agent, or Firm* — Bereskin Parr LLP/S.E.N.C.R.L., s.r.l.; Dominique Lambert

(57) ABSTRACT

The present application relates to compounds of Formula I comprising an antibody binding domain (ABD) comprising a hapten that binds to an antibody in a subject, the antibody comprising a hapten binding site, an antibody labelling domain (ALD) comprising a functional group that forms a covalent bond with an amino acid in the antibody that is proximal to the hapten binding site and the formation of the covalent bond results in elimination of the ABD and either a target binding domain (TBD) or a detection moiety domain (DMD), each domain being optionally connected with independently selected linkers. The present application also includes methods and uses of the compounds, for example, for immune recognition of target cells by recruited labelled antibodies.

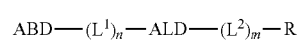

I

15 Claims, 24 Drawing Sheets

Covalent labeling in serum from mice boosted with DNP to produce anti-DNP

Estimation of unknown "x" concentration of boosted anti-DNP

COVALENT IMMUNE RECRUITER COMPOUNDS FOR IMMUNE CELL RECOGNITION AND ASSOCIATED USES

CROSS REFERENCE TO RELATED APPLICATION

The present application claims priority on U.S. 62/981,767 filed on Feb. 26, 2020. This document is hereby incorporated by reference in its entirety.

FIELD

The present application relates to antibody recruiter compounds containing an antibody binding domain, an antibody labelling/reactive domain and either a target binding moiety or a detection moiety domain, as well as processes for their preparation and methods of using such compounds and compositions.

BACKGROUND

The promise of tumor immunotherapy for the treatment of cancer has inspired synthetic small molecule approaches which leverage the specificity of the immune system. One approach advancing toward clinical trials is Antibody Engagers (AE), also known as Antibody Recruiting Molecules (ARMs).[i] AEs are small molecules (≈1-2 kDa) that re-direct hapten specific antibodies (Ab) (e.g. anti-dinitrophenyl (DNP) present in human serum to the surface of tumor cells. These antibodies, which originally lack any intrinsic ability to localize to tumor cells, can now mark the cell for immune mediated destruction. AEs contain reversible tumor surface protein binding (TBD) and antibody binding domains (ABD) allowing the formation of a "ternary complex" at the tumor cell surface (FIG. 1A). These ternary complexes bind activation receptors on immune cells (i.e. CD64 on monocytes) via the recruited antibody to form functional "quaternary complexes" triggering an anti-cancer response.[ii]

The potency and efficacy of ARMs is affected by the number and stability of immunologically active quaternary complexes present at the target surface that bind and activate immune cells. The stability of such complexes is affected by the concentrations and dissociation constants of all species involved.[iii] To maximize quaternary complex formation, ARM affinity for antibody is ideally high ($K_d$=nM) to overcome the potentially low endogenous (native) concentration of target antibody. The antibody concentrations can be sub-saturating (i.e. $[Ab] \leq K_{d(antibody)}$), and thus limit quaternary complex formation in vivo (FIG. 1A). Achieving nM small molecule-protein binding affinity in general is difficult without employing extensive medicinal chemistry protocols.[iiii] Further limits on ARM quaternary complex formation may be due to the rapid clearance of ARMs (≈1-2 kDa MW, Clearance $t_{1/2}$≈1-2 h), driving non-covalent complex dissociation.[iv] Problematically, quaternary complex formation cannot be increased by administering excess ARM because excess ARM leads to autoinhibition of ternary complexes (FIG. 1A).

An alternative tumor immunotherapeutic strategy benefitting from long serum circulation times involves the use of engineered monoclonal antibody engagers (mAb). A number of FDA approved mAbs currently exist such as Trastuzumab "Herceptin" and Daratumumab capable of prolonging survival in metastatic breast and blood cancers associated with a poor prognosis. A major mode of mAb anti-tumor action is known as Antibody Dependent Cellular Cytotoxicity (ADCC). ADCC also involves a "ternary complex" mechanism of action mediated by an IgG antibody which bispecifically binds to/engages the target tumour antigen and immune effector cell receptor such as CD16α.

The efficacy and kinetics of ADCC is especially dependent on the concentration of tumour cell bound antibody which is limited by the poor trafficking/focusing of mAbs to the tumor site following I.V. administration. As a result, exceptionally high therapeutic doses (grams) of mAb are required leading to off-target effects, while placing a burden on manufacturing costs limiting general patient accessibility.

U.S. Pat. No. 9,296,708 describes ARMs comprising an antibody binding terminus linked to a cell binding terminus through a linker and optionally a connector molecule.

There is a need to develop new immune recruiter molecules providing, for example, high binding affinity for target, increased stability of immunological synapses and/or lower pharmacokinetic clearance.

SUMMARY

Described herein is the development of Covalent Immune Recruiters (CIRs) as chemical tools that can "irreversibly" bind Ab and exert control over immune recognition by covalently stabilizing and simplifying quaternary complexes. This is achieved by eliminating the AE:antibody equilibrium through proximity induced covalent labelling. CIRs were synthesized that can selectively label near sub-saturating concentrations of anti-DNP IgG directly in human serum, using only stoichiometric concentrations of the CIR. The resulting conjugates are able to affect immune recognition of model targets including tumor proteins on human cells. CIRs also demonstrate utility as tools in vitro, for example, to directly interrogate immune cell receptor interactions within quaternary complexes by reducing their equilibrium complexity or monitoring and/or quantifying endogenous antibody concentration. In this embodiment, CIRs were prepared having a fluorescent label to facilitate detection. This enables for facile analysis of immune cell binding stability via current three component equilibrium binding models.

Compounds comprising (1) an antibody binding domain (ABD), (2) an antibody labelling domain (ALD), and (3) either a target cell binding domain (TBD) or a detection moiety domain (DMD), displayed immune recognition of target cells by recruited labelled antibodies and detection of labelled antibodies. Specifically, compounds were prepared that displayed selective affinity for recruiting and labelling the DNP binding site of anti-DNP IgGs. Further, the recruited labelled anti-DNPs displayed immune recognition via the TBD moiety to bind to cell surface proteins of the target cell, such as streptavidin or PSMA as well labelled antibodies could be used in standard detection methods, for example, to studying labelling kinetics and/or monitor their concentration. Accordingly, the compounds of Formula I are effective tools for triggering a cytotoxic response to target cells. Comparable compounds not comprising a reactive antibody labelling domain did not display the same immune recognition in the same target cell lines and under similar conditions, highlighting the beneficial results obtained with the compounds of the application.

Therefore, the present application includes a compound of Formula I or a pharmaceutically acceptable salt and/or solvate thereof:

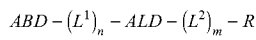

$$ABD-(L^1)_n-ALD-(L^2)_m-R \qquad \text{I}$$

wherein
ABD is an antibody binding domain comprising a hapten that binds to an antibody in a subject, the antibody comprising a hapten binding site;
ALD is an antibody labelling domain comprising a functional group that forms a covalent bond with an amino acid in the antibody that is proximal to the hapten binding site and the formation of the covalent bond results in elimination of the ABD;
$L^1$ and $L^2$ are, independently, linker groups;
n and m are, independently, 0 or 1; and
R is a target binding domain (TBD) or a detection moiety domain (DMD).

In an embodiment, the present application includes a composition comprising one or more compounds of the application and a carrier. In an embodiment, the composition is a pharmaceutical composition and the carrier is a pharmaceutically acceptable carrier.

The present application includes a method for labelling an antibody for detection, either in a biological sample or in a subject, comprising administering an effective amount of one or more compounds of the application wherein R is a DMD, to the biological sample or the subject.

The present application also includes a method for recruiting an antibody and targeting a cell for provoking an immune response to the cell, either in a biological sample or in a subject, comprising administering an effective amount of one or more compounds of the application wherein R is a TBD, to the biological sample or the subject.

The present application also includes a method for recruiting an antibody naturally present in a subject and targeting a cell for provoking an immune response to the cell, either in a biological sample or in the subject, comprising administering an effective amount of one or more compounds of the application wherein R is a TBD, to the biological sample or the subject.

The present application also includes a method for targeting a cell for provoking an immune response to the cell, either in a biological sample or in a subject, comprising administering an effective amount of one or more compounds of the application wherein R is a TBD, to the biological sample or the subject.

The present application also includes a method for provoking cellular phagocytosis of a target cell, either in a biological sample or in a subject, comprising administering an effective amount of one or more compounds of the application wherein R is a TBD, to the biological sample or the subject.

The present application also includes a method of treating a disease, disorder or condition that is treatable by immunotherapy, comprising administering a therapeutically effective amount of one or more compounds of the application wherein R is a TBD, to a subject in need thereof.

The present application also includes a method of treating cancer comprising administering a therapeutically effective amount of one or more compounds of the application wherein R is a TBD, to a subject in need thereof.

Other features and advantages of the present application will become apparent from the following detailed description. It should be understood, however, that the detailed description and the specific examples, while indicating embodiments of the application, are given by way of illustration only and the scope of the claims should not be limited by these embodiments but should be given the broadest interpretation consistent with the description as a whole.

BRIEF DESCRIPTION OF DRAWINGS

The embodiments of the application will now be described in greater detail with reference to the attached drawings in which:

FIG. 1A shows non-covalent complexes for antibody engagers according to prior art; FIG. 1B shows exemplary covalent complexes for covalent immune recruiters of the application.

FIG. 3A shows chemical structures and corresponding domains of exemplary compounds of the application and comparative compounds; FIG. 3B shows antibody labelling kinetic mechanism of exemplary compounds of the application.

FIG. 4A shows the association and dissociation time of an exemplary compound of the application and a comparative compound; FIG. 4B shows antibody recruitment rates of exemplary compounds of the application.

FIG. 5A shows antibody labelling kinetics; FIG. 5B shows quantitative antibody labelling; FIG. 5C shows covalent antibody labelling in human serum; and FIG. 5D shows covalent antibody labelling in mouse serum.

FIG. 7A shows results of flow cytometry covalent antibody recruiting assays; FIG. 7B shows results of a first flow cytometry ADCP assays; FIG. 7C shows an analytical model of data in FIG. 7B; FIG. 7D shows results of a second flow cytometry covalent antibody recruiting assays; FIG. 7E shows a proposed mechanism of CIR mediated ADCP; FIG. 7F shows results of flow cytometry dual colour ADCP assays.

FIG. 9A shows antibody recruitment rates; FIG. 9B shows antibody recruitment kinetics; FIG. 9C and FIG. 9E show results of luminescence ADCC assays; FIG. 9D and FIG. 9F shows results of flow cytometry ADCP assays.

FIG. 10A shows antibody recruitment rates; FIG. 10B shows antibody recruitment kinetics; FIG. 10C shows results of luminescence ADCC assays; FIG. 10D shows results of flow cytometry ADCP assays.

FIG. 12A shows results of flow cytometry antibody recruiting assays using humanized anti-DNP SPE7; FIG. 12B shows results of flow cytometry antibody recruiting assays using monoclonal human anti-DNP.

FIG. 13A shows association and dissociation time with a comparative non-covalent compound; FIG. 13B shows association and dissociation time with an exemplary compound of the application; FIG. 13C and FIG. 13D show results of luminescence ADCC assays.

FIG. 14A shows a proposed mechanism of immune recognition of target cells of comparative compounds; FIG. 14B shows a proposed binding kinetics mechanism of comparative compounds.

DETAILED DESCRIPTION

I. Definitions

Figure 1A:
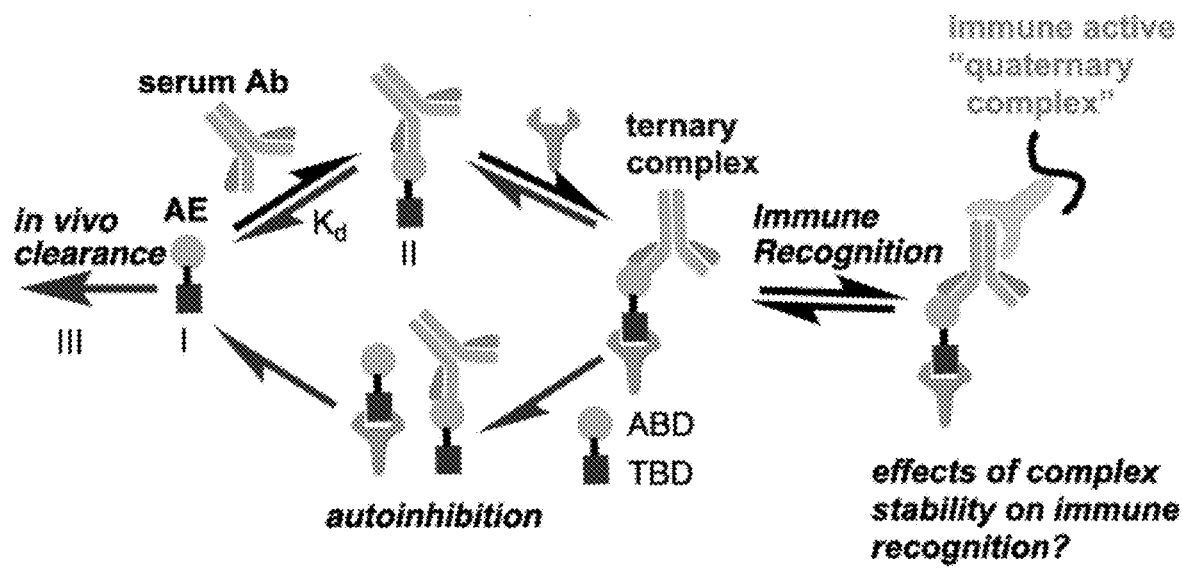
FIGS. 1A and 1B are schematic illustrations of complexes between antibodies, chemical tools and target cells.

Unless otherwise indicated, the definitions and embodiments described in this and other sections are intended to be applicable to all embodiments and aspects of the present application herein described for which they are suitable as would be understood by a person skilled in the art.

The term "compound(s) of the application" or "compound(s) of the present application" and the like as used herein refers to a compound of Formula I or pharmaceutically acceptable salts and/or solvates thereof.

The term "composition(s) of the application" or "composition(s) of the present application" and the like as used herein refers to a composition, such a pharmaceutical composition, comprising one or more compounds of the application.

The term "and/or" as used herein means that the listed items are present, or used, individually or in combination. In effect, this term means that "at least one of" or "one or more" of the listed items is used or present. The term "and/or" with respect to pharmaceutically acceptable salts and/or solvates thereof means that the compounds of the application exist as individual salts and hydrates, as well as a combination of, for example, a solvate of a salt of a compound of the application.

As used in the present application, the singular forms "a", "an" and "the" include plural references unless the content clearly dictates otherwise. For example, an embodiment including "a compound" should be understood to present certain aspects with one compound, or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "consisting" and its derivatives as used herein are intended to be closed terms that specify the presence of the stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The term "suitable" as used herein means that the selection of the particular compound or conditions would depend on the specific synthetic manipulation to be performed, the identity of the molecule(s) to be transformed and/or the specific use for the compound, but the selection would be well within the skill of a person trained in the art.

In embodiments of the present application, the compounds described herein may have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (for example, less than 20%, suitably less than 10%, more suitably less than 5%) of compounds of the present application having an alternate stereochemistry. It is intended that any optical isomers, as separated, pure or partially purified optical isomers or racemic mixtures thereof are included within the scope of the present application.

The compounds of the present application may also exist in different tautomeric forms and it is intended that any tautomeric forms which the compounds form, as well as mixtures thereof, are included within the scope of the present application.

The compounds of the present application may further exist in varying polymorphic forms and it is contemplated that any polymorphs, or mixtures thereof, which form are included within the scope of the present application.

The present description refers to a number of chemical terms and abbreviations used by those skilled in the art. Nevertheless, definitions of selected terms are provided for clarity and consistency.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

The term "alkyl" as used herein, whether it is used alone or as part of another group, means straight or branched chain, saturated alkyl groups. The number of carbon atoms that are possible in the referenced alkyl group are indicated by the prefix "$C_{n1-n2}$". For example, the term $C_{1-10}$alkyl means an alkyl group having 1, 2, 3, 4, 5, 6, 7, 8, 9 or 10 carbon atoms.

The term "alkylene", whether it is used alone or as part of another group, means straight or branched chain, saturated alkylene group, that is, a saturated carbon chain that contains substituents on two of its ends. The number of carbon atoms that are possible in the referenced alkylene group are indicated by the prefix "$C_{n1-n2}$". For example, the term $C_{2-6}$alkylene means an alkylene group having 2, 3, 4, 5 or 6 carbon atoms.

The term "aryl" as used herein, whether it is used alone or as part of another group, refers to carbocyclic groups containing at least one aromatic ring and contains either 6 to 20 carbon atoms.

The term "amine" or "amino," as used herein, whether it is used alone or as part of another group, refers to groups of the general formula NR'R", wherein R' and R" are each independently selected from hydrogen or $C_{1-6}$alkyl.

The term "amino acid" as used herein refers to an organic compound comprising amine ($-NH_2$) and carboxylic acid ($-COOH$) functional groups, along with a side-chain specific to each amino acid. The common elements of an amino acid are carbon, hydrogen, oxygen and nitrogen, though other elements are found in the side-chains of certain amino acids, including S and Se. Unless otherwise specified, an amino acid referenced herein is one of the 23 proteinogenic amino acids, that is amino acids that are precursors to proteins, and are incorporated into proteins during translation.

The term "carbamide" or "carbamido" as used herein, whether it is used alone or as part of another group, refers to a functional group containing a carbonyl group bonded to two nitrogen atoms of the general formula NR'R"CONR'R", wherein R' and R" are each independently selected from hydrogen or other functional groups.

The following symbol:

is used in chemical structures herein to represent a point of covalent attachment of a group to another group.

The term "atm" as used herein refers to atmosphere.

The term "MS" as used herein refers to mass spectrometry.

The term "aq." as used herein refers to aqueous.

DCM as used herein refers to dichloromethane.

DIPEA or DIEA as used herein refers to N,N-diisopropyl ethylamine

DMF as used herein refers to dimethylformamide.

DMSO as used herein refers to dimethylsulfoxide.

EtOAc as used herein refers to ethyl acetate.

MeOH as used herein refers to methanol.

ACN as used herein refers to acetonitrile.

HCl as used herein refers to hydrochloric acid.

TFA as used herein refers to trifluoroacetic acid.

NHS as used herein refers to N-hydroxysuccinimide ester.

Boc as used herein refers to tert-butyloxycarbonyl.

EDCl as used herein refers to 1-ethyl-3-(3-dimethylaminopropyl)carbodiimide.

HOBt as used herein refers to hydroxybenzotriazole.

TEA as used herein refers to trimethylamine.

DTB as used herein refers to di-tert-Butyl peroxide.

PEG as used herein refers to polyethylenglycol.

rt as used herein refers to room temperature.

PSMA as used herein refers to prostate specific membrane antigen.

PBS as used herein refers to phosphate-buffered saline.

FBS as used herein refers to fetal bovine serum.

SDS-PAGE as used herein refers to sodium dodecyl sulfate-polyacrylamide gel electrophoresis.

PMPA as used herein refers to 9-[2-(Phosphonomethoxy)Propyl]Adenine

LCMS as used herein refers to liquid chromatography-mass spectrometry.

ARM as used herein refers to antibody recruiting molecule.

Ab as used herein refers to antibody.

NK as used herein refers to natural killer cells.

BiTEs as used herein refers to bi-specific T cell engagers.

BiKEs as used herein refers to bi-specific NK cell engagers

ABD as used herein refers to antibody binding domain.

ALD as used herein refers to antibody labelling domain.

TBD as used herein refers to target cell binding domain.

CIR as used herein refers to covalent immune recruiter.

NCIR as used herein refers to non-reactive covalent immune recruiter.

DNP as used herein refers to dinitrophenyl.

IgG as used herein refers to immunoglobulin G.

ADCP as used herein refers to antibody dependent cellular phagocytosis.

ADCC as used herein refers to antibody dependent cellular cytotoxicity.

BLI as used herein refers to biolayer interferometry.

FP as used herein refers to fluorescence polarization.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T.W. and Wuts, P.G.M., "Protective Groups in Organic Synthesis", John Wiley & Sons, 3$^{rd}$ Edition, 1999 and in Kocienski, P. Protecting Groups, 3$^{rd}$ Edition, 2003, Georg Thieme Verlag (The Americas).

The term "linker" or "linker group" as used herein refers to any molecular structure that joins two or more other molecular structures together and that is compatible with a biological environment.

The term "compatible with a biological environment" as used herein it is meant that the chemical group or molecule is stable in, and/or does not denature, other molecules present in biological systems.

The term "biological systems" as used herein means any of a wide variety of systems which comprise proteins, enzymes, organic compounds, inorganic compounds, other sensitive biopolymers including DNA and RNA, and includes complex systems such as whole or fragments of plant, animal and microbial cells.

The term "subject" as used herein includes all members of the animal kingdom including mammals, and suitably refers to humans. Thus the methods and uses of the present application are applicable to both human therapy and veterinary applications.

The term "pharmaceutically acceptable" means compatible with the treatment of subjects.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject.

The term "pharmaceutically acceptable salt" means either an acid addition salt or a base addition salt which is suitable for, or compatible with, the treatment of subjects.

An acid addition salt suitable for, or compatible with, the treatment of subjects is any non-toxic organic or inorganic acid addition salt of any basic compound.

A base addition salt suitable for, or compatible with, the treatment of subjects is any non-toxic organic or inorganic base addition salt of any acidic compound.

The term "solvate" as used herein means a compound, or a salt of a compound, wherein molecules of a suitable solvent are incorporated in the crystal lattice The term "prodrug" as used herein means a compound, or salt and/or solvate of a compound, that, after administration, is converted into an active drug.

The term "treating" or "treatment" as used herein and as is well understood in the art, means an approach for obtaining beneficial or desired results, including clinical results. Beneficial or desired clinical results include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. "Treating" and "treatment" as used herein also include prophylactic treatment. For example, a subject with early cancer can be treated to prevent progression, or alternatively a subject in remission can be treated with a compound or composition of the application to prevent recurrence. Treatment methods comprise administering to a subject a therapeutically effective amount of one or more of the compounds of the application and optionally consist of a single administration, or alternatively comprise a series of administrations.

"Palliating" a disease, disorder or condition means that the extent and/or undesirable clinical manifestations of a disease, disorder or condition are lessened and/or time course of the progression is slowed or lengthened, as compared to not treating the disorder.

The term "prevention" or "prophylaxis", or synonym thereto, as used herein refers to a reduction in the risk or probability of a subject becoming afflicted with a disease, disorder or condition or manifesting a symptom associated with a disease, disorder or condition.

The term "disease, disorder or condition" as used herein refers to a disease, disorder or condition treatable by immunotherapy, such as by one or more compounds of the application.

The term "immunotherapy" as used herein refers to the treatment of disease, disorder or condition by activating the immune system to produce or provoke an immune response.

The term "immune response" as used herein refers to the activation of immune cells.

The term "hapten" as used herein refers to a small molecule that can elicit an immune response only when attached to a large carrier such as a protein. The carrier may be one that also does not elicit an immune response by itself.

As used herein, the term "effective amount" or "therapeutically effective amount" means an amount of one or more compounds of the application that is effective, at dosages and for periods of time necessary to achieve the desired result. For example, in the context of treating a disease, disorder or condition mediated or treatable by immunotherapy, an effective amount is an amount that, for example, provoke an immune response compared to without administration of the one or more compounds.

The term "administered" as used herein means administration of a therapeutically effective amount of one or more compounds or compositions of the application to a cell, tissue, organ or subject.

The term "neoplastic disorder" as used herein refers to a disease, disorder or condition characterized by cells that have the capacity for autonomous growth or replication, e.g., an abnormal state or condition characterized by proliferative cell growth. The term "neoplasm" as used herein refers to a mass of tissue resulting from the abnormal growth and/or division of cells in a subject having a neoplastic disorder.

The term "cancer" as used herein refers to cellular-proliferative disease states.

II. Compounds and Compositions of the Application

Compounds containing (1) an antibody binding domain (ABD), (2) an antibody labelling domain (ALD), and (3) a target cell binding domain (TBD) or a detection moiety domain (DMD), have been prepared. The three highly tunable domains enable the compounds to form a selective covalent linkage proximal to the binding site on the antibody, equipping it with permanent cell targeting or detection functions. In one embodiment, the compounds display immune recognition of target cells by recruited labelled antibodies. In another embodiment, the compounds display fluorescence allowing them to be detected and used, for example, as a tool to study the kinetics or concentration of the labelled antibody. Specifically, exemplary compounds displayed selective affinity for recruiting and labelling the DNP binding site of anti-DNP IgGs. Further, the recruited labelled anti-DNPs display immune recognition via the TBD moiety to bind to cell surface proteins of the target cell, such as streptavidin or PSMA or fluorescence via the detection moiety to study, for example, labelling kinetics and/or antibody concentration. Accordingly, compounds of the application are effective tools for triggering a cytotoxic response in target cells or as research tools. Comparable compounds not comprising a reactive antibody labelling domain did not display the same immune recognition in the same target cell lines and under similar conditions, highlighting the beneficial results obtained with the compounds of the application.

Accordingly, the present application includes a compound of Formula I or a pharmaceutically acceptable salt and/or solvate thereof:

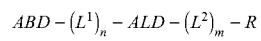

$$ABD-(L^1)_n-ALD-(L^2)_m-R \qquad \text{I}$$

wherein

ABD is an antibody binding domain comprising a hapten that binds to an antibody in a subject, the antibody comprising a hapten binding site;

ALD is an antibody labelling domain comprising a functional group that forms a covalent bond with an amino acid in the antibody that is proximal to the hapten binding site and the formation of the covalent bond results in elimination of the ABD;

$L^1$ and $L^2$ are, independently, linker groups;

n and m are, independently, 0 or 1; and

R is a target binding domain (TBD) or a detection moiety domain (DMD).

Antibody Binding Domains (ABD)

In an embodiment, the ABD comprises a hapten which binds to an antibody that is endogenous in the subject. In an embodiment, the antibody is present in the subject prior to treatment (i.e. the antibody levels do not have to be raised in the subject prior to treatment). In an embodiment, the antibody that is endogenous in the subject is an anti-dinitrophenyl (DNP) IgG. In an embodiment, the anti-DNP IgG is present in the subject's serum. In an embodiment, the ABD is a hapten comprising a DNP for binding the anti-DNP IgG.

In an embodiment, the hapten comprises an electron deficient aryl or a carbohydrate. In an embodiment, the electron deficient aryl group is di- or trinitro phenyl. In an embodiment the carbohydrate comprises digalactose.

In an embodiment, the ABD comprises any of the hapten groups described in U.S. Pat. No. 9,296,708. Accordingly, the ABD group may be one of the following groups:

(1) a di- or trinitrophenyl group having the following structure:

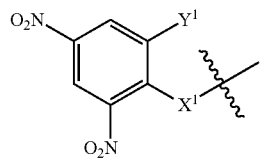

wherein $Y^1$ is H or $NO_2$;

$X^1$ is $NR^1$, O, $CH_2$, S(O), $SO_2$, $SO_2O$, $OSO_2$ or $OSO_2O$; and $R^1$ is H, $C_{1-4}$alkyl or $C(O)C_{1-4}$alkyl;

(2) a bicyclic nitro-substituted aromatic group having the following structure:

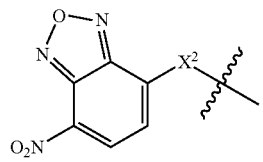

wherein $X^2$ is a bond, O, $CH_2$, $NR^2$ or S; and $R^2$ is H, $C_{1-4}$alkyl or $C(O)C_{1-4}$alkyl;

(3) a galactose-containing carbohydrate having the following structure:

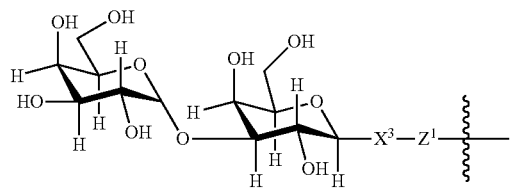

wherein $X^3$ is $CH_2$, O, $NR^3$ or S;

$R^3$ is H or $C_{1-4}$alkyl- and $Z^1$ is a bond, monosaccharide, disaccharide, oligosaccharide, glycoprotein or glycolipid; or (4) a group having the following structure:

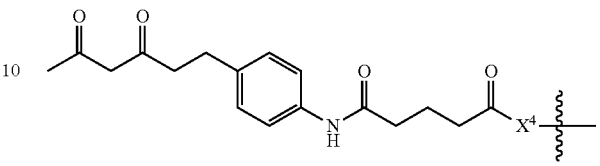

wherein $X^4$ is O, $CH_2$ or $NR^4$; and $R^4$ is H, $C_{1-4}$alkyl or $C(O)C_{1-4}$alkyl.

In an embodiment, $X^1$ is $NR^1$ and $R^1$ is H or $C_{1-3}$alkyl. In an embodiment $Y^1$ is H.

In an embodiment, $X^2$ is a bond or $NR^2$ and $R^2$ is H or $C_{1-3}$alkyl.

In an embodiment, $X^3$ is O or $NR^3$ and $R^3$ is H or $C_{1-3}$alkyl. In an embodiment, $Z^1$ is a bond. In an embodiment, $Z^1$ is a monosaccharide or a disaccharide. In an embodiment, the monosaccharide is an aldose such as aldotriose (D-glyceraldehye, among others), aldotetrose (D-erythrose and D-Threose, among others), aldopentose, (D-ribose, D-arabinose, D-xylose, D-lyxose, among others) or aldohexose (D-allose, D-altrose, D-Glucose, D-Mannose, D-gulose, D-idose, D-galactose and D-Talose, among others). In an embodiment, the monosaccharide is a ketose such as ketotriose (dihydroxyacetone, among others), ketotetrose (D-erythrulose, among others), ketopentose (D-ribulose and D-xylulose, among others) or ketohexose (D-Psicone, D-Fructose, D-Sorbose, D-Tagatose, among others). In an embodiment the monosaccharide is an aminosugar such as galactoseamine, sialic acid, N-acetylglucosamine, among others or a sulfosugar such as sulfoquinovose, among others. In an embodiment Z is a disaccharide such as sucrose (which may have the glucose optionally N-acetylated), lactose (which may have the galactose and/or the glucose optionally N-acetylated), maltose (which may have one or both of the glucose residues optionally N-acetylated), trehalose (which may have one or both of the glucose residues optionally N-acetylated), cellobiose (which may have one or both of the glucose residues optionally N-acetylated), kojibiose (which may have one or both of the glucose residues optionally N-acetylated), nigerose (which may have one or both of the glucose residues optionally N-acetylated), iso-maltose (which may have one or both of the glucose residues optionally N-acetylated), β,β-trehalose (which may have one or both of the glucose residues optionally N-acetylated), sophorose (which may have one or both of the glucose residues optionally N-acetylated), laminaribiose (which may have one or both of the glucose residues optionally N-acetylated), gentiobiose (which may have one or both of the glucose residues optionally N-acetylated), turanose (which may have the glucose residue optionally N-acetylated), maltulose (which may have the glucose residue optionally N-acetylated), palatinose (which may have the glucose residue optionally N-acetylated), gentiobiuose (which may have the glucose residue optionally N-acetylated), mannobiose, melibiose (which may have the glucose residue and/or the galactose residue optionally N-acetylated), melibiulose (which may have the galactose residue optionally N-acetylated), rutinose, (which may have the glucose residue optionally N-acetylated), rutinulose or xylobiose, among others. In an embodiment $Z^1$ is an oligosaccharide such as any sugar of three or more (up to about 100) individual sugar (saccharide) units as described above (i.e., any one or more saccharide units described above, in any order, especially including glucose and/or galactose units as set forth above), or for example, fructo-oligosaccharides, galactooligosaccharides or mannan-oligosaccharides ranging from three to about ten-fifteen sugar units in size. In an embodiment, $Z^1$ is a glycoprotein such as N-glycosylated or O-glycosylated glycoproteins, including the mucins, collagens, transferring, ceruloplasmin, major histocompatability complex proteins (MHC), enzymes, lectins, selectins, calnexin, calreticulin, or integrin glycoprotein IIb/IIa, among others. In an embodiment $Z^1$ is a glycolipid such as a glyceroglycolipid (galactolipids or sulfolipids) or a glycosphingolipid, such as cerebrosides, galactocerebrosides, glucocerebrosides (including glucobicaranateoets), gangliosides, globosides, sulfatides, glycophosphphingolipids or glycocalyx, among others.

In an embodiment, $Z^1$ is a bond or a glucose or glucosamine (such as N-acetylglucosamine). In an embodiment, $Z^1$ is linked to a galactose residue through a hydroxyl group or an amine group on the galactose of Gal-Gal, suitably a hydroxyl group.

In an embodiment, $X^4$ is $NR^4$ and $R^4$ is H or $C_{1-3}$alkyl.

In an embodiment, the ABD is:

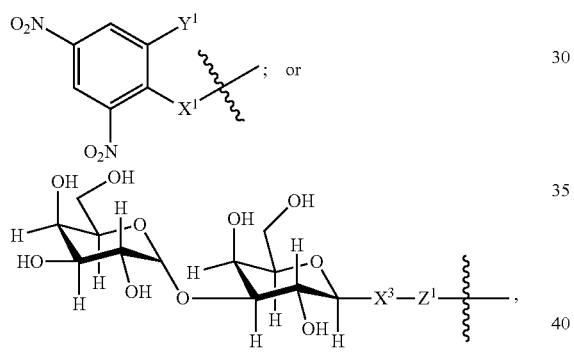

wherein
$Y^1$ is H or $NO_2$, suitably H;
$X^1$ is NH or O, suitably NH;
$X^3$ is O; and
$Z^1$ is a bond, a monosaccharide or a disaccharide, suitable a bond.

In an embodiment, the ABD is selected from a variety of monosaccharide or multivalent derivatives thereof recognized by several different serum carbohydrate specific antibodies such as anti-rhamnose and N-acetylglucosamine. In some embodiments, the ABD comprises synthetic ligands such as cyclic peptides that bind all serum IgG.

Target Cell Binding Domains (TBD)

Target cell binding domains comprise moieties which are taken up and retained in a particular site of a subject such as a biological structure for example an organ or tissue or a pathological structure for example a tumor, with little or no accumulation and/or retention in non-target sites over a particular time period. In an embodiment, the targeting moiety binds to a protein, for example a protein that is overexpressed in a disease, disorder or condition such as cancer. Targeting moieties are known and the selection of a suitable targeting moiety for a particular imaging or therapeutic use can be made by a person skilled in the art. Targeting moieties include, but are not limited to, small molecules such as protein binding compounds, enzyme inhibitors or pharmaceutical-like compounds.

In an embodiment, the TBD comprises a moiety that binds to antigens on the surface of a target cell. In an embodiment, the TDB is a glutamate urea ligand that binds to prostate specific membrane antigen (PSMA).

In an embodiment, the TBD comprises any of the target cell binding domain groups described in U.S. Pat. No. 9,296,708. Accordingly, the TBD group may be one of the following groups:

(1)

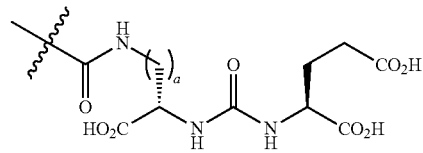

wherein a is an integer from 0 to 10, 1 to 15, 1 to 10, 1 to 8, or 1, 2, 3, 4, 5 or 6;

(2)

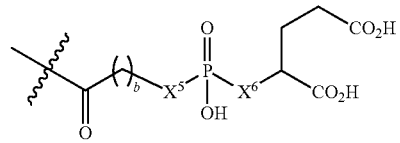

wherein $X^5$ and $X^6$ are independently $CH_2$, O, NH or S; and
b is an integer from 0 to 10, 1 to 15, 1 to 10, 1 to 8, or 1, 2, 3, 4, 5 or 6;

(3)

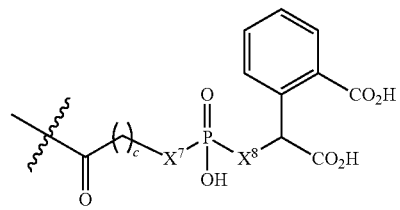

wherein $X^7$ and $X^8$ are independently $CH_2$, O, NH or S; and
c is an integer from 0 to 10, 1 to 15, 1 to 10, 1 to 8, or 1, 2, 3, 4, 5 or 6;

(4)

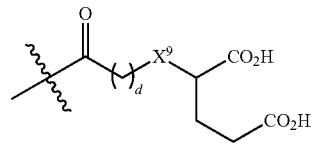

wherein $X^9$ is O, $CH_2$, $NR^5$, S(O), $SO_2$, $SO_2O$, $OSO_2$ or $OSO_2O$;
$R^5$ is H, $C_{1-4}$alkyl or $C(O)C_{1-4}$alkyl; and
d is an integer from 0 to 10, 1 to 15, 1 to 10, 1 to 8, or 1, 2, 3, 4, 5 or 6; or (5) biotin or a biotin analog such as:

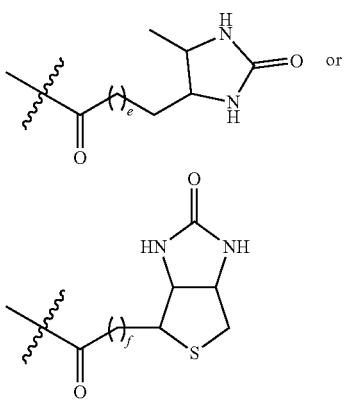

wherein e and f are, independently, an integer from 0 to 10, 1 to 15, 1 to 10, 1 to 8, or 1, 2, 3, 4, 5 or 6.

In an embodiment, a, b, c, d, e and f are independently 1, 2, 3, 4, 5 or 6, suitably 2, 3 or 4, more suitably 4.

In an embodiment, the TBD group is one of the following groups:

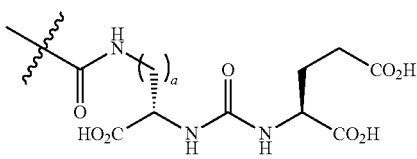

wherein a is 1, 2, 3, 4, 5 or 6; or

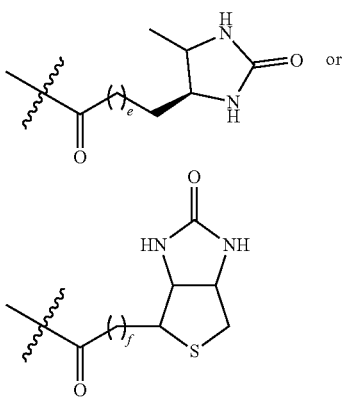

wherein e and f are, independently, 1, 2, 3, 4, 5 or 6.

In some embodiments, the TBD group comprises other tumor antigen binding ligands such as synthetic peptides against uPAR or HER2, or folate receptor binding molecules such as folate or methotrexate, or TLR agonists or PD-1/PD-L1 antagonists.

Detection Moiety Domain (DMD)

In an embodiment, the DMD is any group that is used for detection using methods known in the art and that is compatible with a biological environment. Different types of detection moieties are known in the art depending on the form of detection to be used. In some embodiments, the detection moiety is selected from a radiolabel, a fluorescent label, a fluorogenic group, a spin label, isotope label, a positron emission tomography (PET) and a single-photon emission computed tomography label.

In an embodiment, the detection method is fluorescence and the DMD comprises a fluorescent moiety. A person skilled in the art would appreciate that any fluorescent moiety known in the art that is compatible with biological systems may be used and that such groups are numerous. A fluorescent moiety comprises a fluorophore (or fluorochrome) which is a fluorescent chemical compound that can re-emit light upon light excitation. Fluorophores typically contain several combined aromatic groups, or planar or cyclic molecules with several pi bonds. Fluorophores may also comprise quantum dots, which are fluorescent semiconductor nanoparticles or a fluorescent protein, such as Green Fluorescent Protein (GFP). Examples of fluorophores include, but are not limited to, fluorescein and derivatives thereof, cyanine dyes, metal-based fluorophores, boron-dipyrromethene (BODIPY) dyes, sulforhodamine 101 acid chloride (Texas Red), Alexa Fluor™ dyes and rhodamine dyes.

In an embodiment, the DMD is

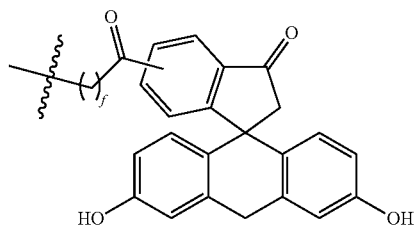

wherein f is an integer from 0 to 10, 1 to 15, 1 to 10, 1 to 8, or 0, 1, 2, 3, 4, 5 or 6. In an embodiment, f is 0.

In an embodiment, the detection method is radioactivity detection and the DMD comprises a radioactive label (radiolabel). Radiolabel form the basis of a variety of detection method, such as imaging using Positron Emission Tomography (PET), Single-Photon Emission Computed Tomography (SPECT) and technetium scanning.

Antibody Labelling Domains (ALD)

Figure 1B:
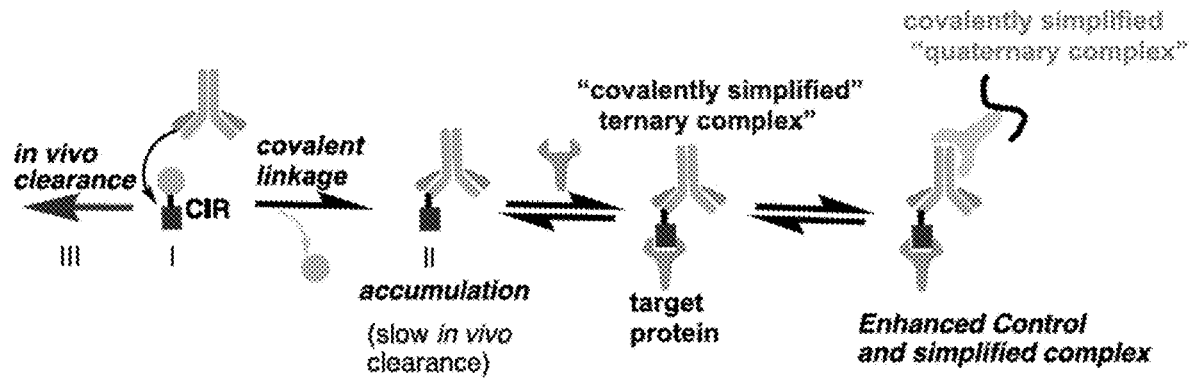

ALD is an antibody labelling domain comprising a functional group that forms a covalent bond with an amino acid in the antibody that is proximal to the hapten binding site and the formation of the covalent bond results in elimination of the ABD (See FIG. 1B).

In an embodiment, the ALD comprises a moiety that reacts with an amino acid in the antibody to form a covalent bond with the antibody and the reaction results in elimination (or displacement) of the ABD. The amino acid in the antibody is proximal to the binding site for the hapten in the ABD. By "proximal" it is meant that the amino acid is located in an area that, when the compound of Formula I is bound to the antibody via the ABD, the amino acid is in a spatial location to react with the ALD. For example, the distance between the amino acid and the ALD may be about 2 Å to about 10 Å.

In some embodiments, the ALD comprises an electrophilic functional group that reacts with an amino acid nucleophile in a nucleophilic substitution reaction. In an embodiment, the amino acid nucleophile is an amine ($NH_2$) or a thiol (SH). In an embodiment, the electrophilic functional group in the ALD comprises an imidazole group having the following structure:

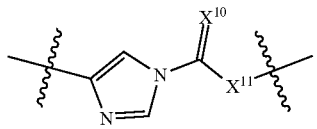

wherein
$X^{10}$ is S, O or $NR^6$;
$X^{11}$ is O or $NR^7$; and
$R^6$ and $R^7$ are independently H or $C_{1-4}$alkyl.
In an embodiment, $X^{10}$ and $X^{11}$ are both O.

A person skilled in the art would appreciate that there are many other functional groups that may be used in the ALD. Such group would be compatible with a biological environment and would react with a functional group on an amino acid in an antibody to form a covalent bond, wherein formation of the covalent bond results in elimination of the ABD.

Linker Groups

A person of skill in the art would appreciate that the linkers $L^1$ and $L^2$ should have a length and spatial orientation appropriate to link the ABD moiety with the ALD moiety and the ALD moiety with the TBD/DMD (R) moiety. In some embodiments, the linker rigidity and length is tuned to maximize labeling kinetics and further comprises rigidifying elements such as carbocycles, heterocycles, aromatics and/or heteroaromatics.

Linkers may be any molecular structure that joins two or more other molecular structures together and that is compatible with a biological environment. In an embodiment, the linker moiety comprises at least one ester, amide, ether, thioether, thioamide, thioester and/or amine.

In an embodiment, $L^1$ and $L^2$, are independently, $C_{1-20}$ alkylene, optionally interrupted by triazolyl and/or one or more heteromoieties such as O, S, S(O), $SO_2$, $OSO_2$, $SO_2O$, $OSO_2O$, $NR^8$, C(O), NHC(O), or C(O)NH, wherein $R^8$ is H or $C_{1-4}$alkyl. In an embodiment, $L^1$ and $L^2$ are independently, a group having the following structure:

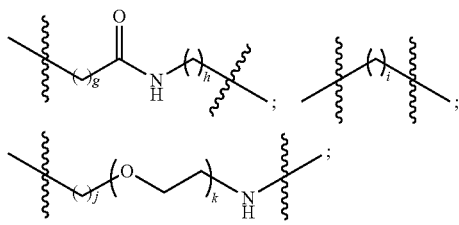

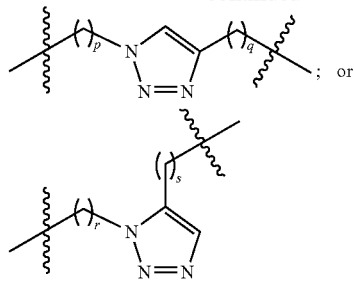

wherein, g, h, i, j, k, p, q, r and s are, independently, 1, 2, 3, 4, 5, 6, 7, 8, 9 or 10.

In an embodiment, j is 2 and k is 3. In an embodiment, g is 1 and h is 2. In an embodiment, i is 1, 2, 3, 4, 5, 6, 7, 8, 9 or 10. In an embodiment, p, q, r and s are, independently, 1, 2, 3 or 4.

In an embodiment, the linker groups are present, therefore n and m in the compounds of Formula I are both 1 and the compounds have the following structure:

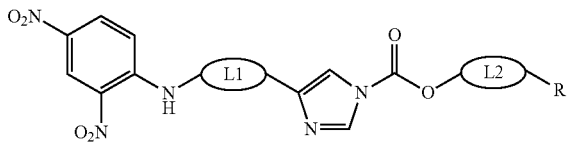

I wherein
R is TBD.
In an embodiment, R is

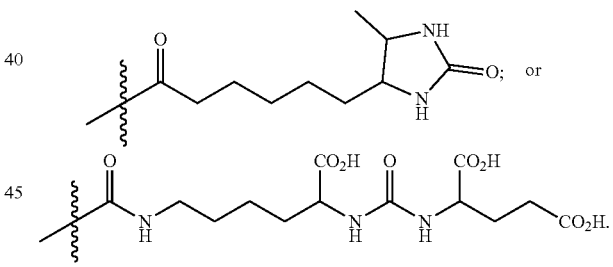

In an embodiment, the compound of Formula I is:

| Compound I.D. | Example # | Structure |
|---|---|---|
| 1-1 CIR 1 | 1 | ![structure] |

| Compound I.D. | Example # | Structure |
|---|---|---|
| 1-2 CIR 2 | 2 | 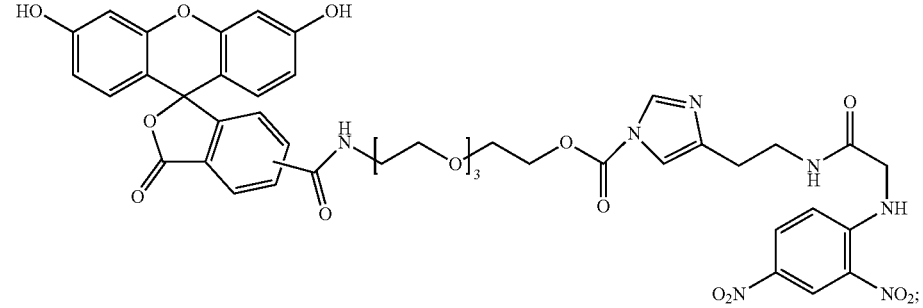 |
| 1-3 CIR 3 | 3 | 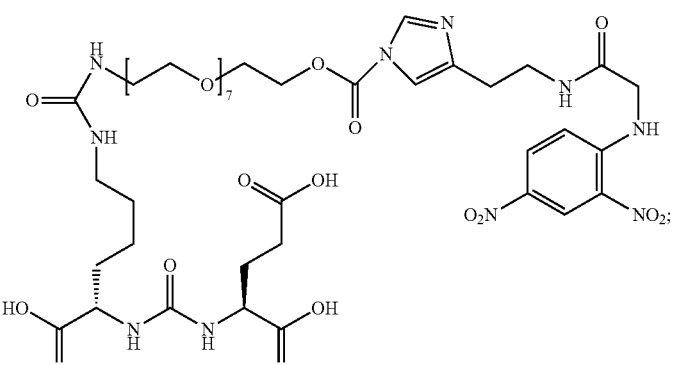 |
| 1-4 CIR 4 | 4 | 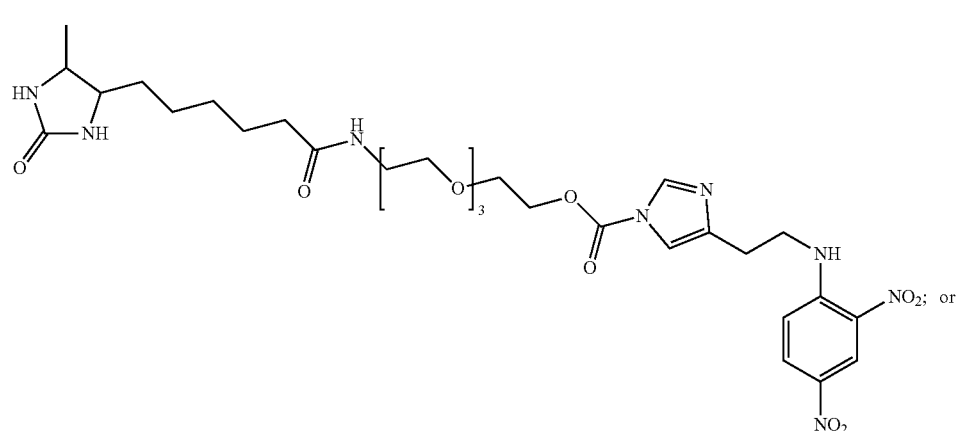 |
| 1-5 CIR 5 | 5 | 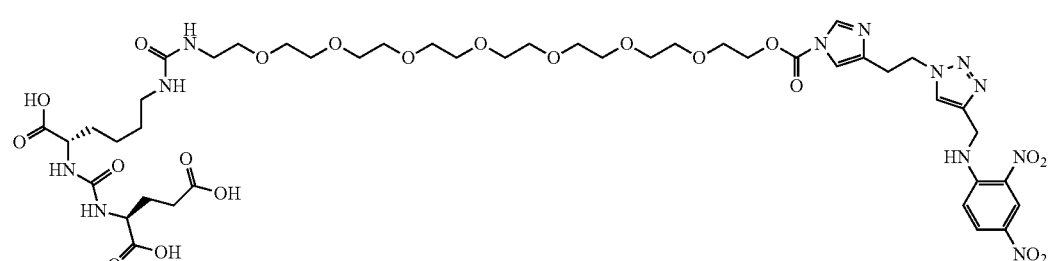 | or a pharmaceutically acceptable salt and/or solvate thereof.

In an embodiment the pharmaceutically acceptable salt is an acid addition salt or a base addition salt. The selection of a suitable salt may be made by a person skilled in the art (see, for example, S. M. Berge, et al., "Pharmaceutical Salts," J. Pharm. Sci. 1977, 66, 1-19).

An acid addition salt suitable for, or compatible with, the treatment of subjects is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. In an embodiment, the mono- or di-acid salts are formed, and such salts exist in either a hydrated, solvated or substantially anhydrous form. In general, acid addition salts are more soluble in water and various hydrophilic organic solvents, and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the application for laboratory use, or for subsequent conversion to a pharmaceutically acceptable acid addition salt.

A base addition salt suitable for, or compatible with, the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide as well as ammonia. Illustrative organic bases which form suitable salts include aliphatic, alicyclic or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. The selection of the appropriate salt may be useful, for example, so that an ester functionality, if any, elsewhere in a compound is not hydrolyzed. The selection criteria for the appropriate salt will be known to one skilled in the art.

Solvates of compounds of the application include, for example, those made with solvents that are pharmaceutically acceptable. Examples of such solvents include water (resulting solvate is called a hydrate) and ethanol and the like. Suitable solvents are physiologically tolerable at the dosage administered.

Compositions

The compounds of the present application are suitably formulated in a conventional manner into compositions using one or more carriers. Accordingly, the present application also includes a composition comprising one or more compounds of the application and a carrier. The compounds of the application are suitably formulated into pharmaceutical compositions for administration to subjects in a biologically compatible form suitable for administration in vivo. Accordingly, the present application further includes a pharmaceutical composition comprising one or more compounds of the application and a pharmaceutically acceptable carrier. In embodiments of the application the pharmaceutical compositions are used in the treatment of any of the diseases, disorders or conditions described herein.

The compounds of the application are administered to a subject in a variety of forms depending on the selected route of administration, as will be understood by those skilled in the art. For example, a compound of the application is administered by oral, inhalation, parenteral, buccal, sublingual, nasal, rectal, vaginal, patch, pump, topical or transdermal administration and the pharmaceutical compositions formulated accordingly. In some embodiments, administration is by means of a pump for periodic or continuous delivery. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

Parenteral administration includes systemic delivery routes other than the gastrointestinal (GI) tract, and includes, for example intravenous, intra-arterial, intraperitoneal, subcutaneous, intramuscular, transepithelial, nasal, intrapulmonary (for example, by use of an aerosol), intrathecal, rectal and topical (including the use of a patch or other transdermal delivery device) modes of administration. Parenteral administration may be by continuous infusion over a selected period of time.

In some embodiments, a compound of the application is orally administered, for example, with an inert diluent or with an assimilable edible carrier, or it is enclosed in hard or soft shell gelatin capsules, or it is compressed into tablets, or it is incorporated directly with the food of the diet. In some embodiments, the compound is incorporated with excipient and used in the form of ingestible tablets, buccal tablets, troches, capsules, caplets, pellets, granules, lozenges, chewing gum, powders, syrups, elixirs, wafers, aqueous solutions and suspensions, and the like. In the case of tablets, carriers that are used include lactose, corn starch, sodium citrate and salts of phosphoric acid. Pharmaceutically acceptable excipients include binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). In embodiments, the tablets are coated by methods well known in the art. In the case of tablets, capsules, caplets, pellets or granules for oral administration, pH sensitive enteric coatings, such as Eudragits™ designed to control the release of active ingredients are optionally used. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions are formulated, for example as liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. In some embodiments, liposomes are formed from a variety of phospholipids, such as cholesterol, stearylamine or phosphatidylcholines. For oral administration in a capsule form, useful carriers or diluents include lactose and dried corn starch.

In some embodiments, liquid preparations for oral administration take the form of, for example, solutions, syrups or suspensions, or they are suitably presented as a dry product for constitution with water or other suitable vehicle before use. When aqueous suspensions and/or emulsions are administered orally, the compound of the application is suitably suspended or dissolved in an oily phase that is combined with emulsifying and/or suspending agents. If desired, certain sweetening and/or flavoring and/or coloring agents are added. Such liquid preparations for oral administration are prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid). Useful diluents include lactose and high molecular weight polyethylene glycols.

It is also possible to freeze-dry the compounds of the application and use the lyophilizates obtained, for example, for the preparation of products for injection.

In some embodiments, a compound of the application is administered parenterally. For example, solutions of a compound of the application are prepared in water suitably mixed with a surfactant such as hydroxypropylcellulose. In some embodiments, dispersions are prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. For parenteral administration, sterile solutions of the compounds of the application are usually prepared, and the pH's of the solutions are suitably adjusted and buffered. For intravenous use, the total concentration of solutes should be controlled to render the preparation isotonic. For ocular administration, ointments or droppable liquids are delivered, for example, by ocular delivery systems known to the art such as applicators or eye droppers. In some embodiment, such compositions include mucomimetics such as hyaluronic acid, chondroitin sulfate, hydroxypropyl methylcellulose or polyvinyl alcohol, preservatives such as sorbic acid, EDTA or benzyl chromium chloride, and the usual quantities of diluents or carriers. For pulmonary administration, diluents or carriers will be selected to be appropriate to allow the formation of an aerosol.

In some embodiments, a compound of the application is formulated for parenteral administration by injection, including using conventional catheterization techniques or infusion. Formulations for injection are, for example, presented in unit dosage form, e.g., in ampoules or in multi-dose containers, with an added preservative. In some embodiments, the compositions take such forms as sterile suspensions, solutions or emulsions in oily or aqueous vehicles, and contain formulating agents such as suspending, stabilizing and/or dispersing agents. In all cases, the form must be sterile and must be fluid to the extent that easy syringability exists. Alternatively, the compounds of the application are suitably in a sterile powder form for reconstitution with a suitable vehicle, e.g., sterile pyrogen-free water, before use.

In some embodiments, compositions for nasal administration are conveniently formulated as aerosols, drops, gels and powders. For intranasal administration or administration by inhalation, the compounds of the application are conveniently delivered in the form of a solution, dry powder formulation or suspension from a pump spray container that is squeezed or pumped by the subject or as an aerosol spray presentation from a pressurized container or a nebulizer. Aerosol formulations typically comprise a solution or fine suspension of the active substance in a physiologically acceptable aqueous or non-aqueous solvent and are usually presented in single or multidose quantities in sterile form in a sealed container, which, for example, take the form of a cartridge or refill for use with an atomising device. Alternatively, the sealed container is a unitary dispensing device such as a single dose nasal inhaler or an aerosol dispenser fitted with a metering valve which is intended for disposal after use. Where the dosage form comprises an aerosol dispenser, it will contain a propellant which is, for example, a compressed gas such as compressed air or an organic propellant such as fluorochlorohydrocarbon. Suitable propellants include but are not limited to dichlorodifluoromethane, trichlorofluoromethane, dichlorotetrafluoroethane, heptafluoroalkanes, carbon dioxide or another suitable gas. In the case of a pressurized aerosol, the dosage unit is suitably determined by providing a valve to deliver a metered amount. In some embodiments, the pressurized container or nebulizer contains a solution or suspension of the active compound. Capsules and cartridges (made, for example, from gelatin) for use in an inhaler or insufflator are, for example, formulated containing a powder mix of a compound of the application and a suitable powder base such as lactose or starch. The aerosol dosage forms can also take the form of a pump-atomizer.

Compositions suitable for buccal or sublingual administration include tablets, lozenges, and pastilles, wherein a compound of the application is formulated with a carrier such as sugar, acacia, tragacanth, or gelatin and glycerine. Compositions for rectal administration are conveniently in the form of suppositories containing a conventional suppository base such as cocoa butter.

Suppository forms of the compounds of the application are useful for vaginal, urethral and rectal administrations. Such suppositories will generally be constructed of a mixture of substances that is solid at room temperature but melts at body temperature. The substances commonly used to create such vehicles include but are not limited to *theobroma* oil (also known as cocoa butter), glycerinated gelatin, other glycerides, hydrogenated vegetable oils, mixtures of polyethylene glycols of various molecular weights and fatty acid esters of polyethylene glycol. See, for example: Remington's Pharmaceutical Sciences, 16th Ed., Mack Publishing, Easton, P A, 1980, pp. 1530-1533 for further discussion of suppository dosage forms.

In some embodiments a compound of the application is coupled with soluble polymers as targetable drug carriers. Such polymers include, for example, polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, in some embodiments, a compound of the application is coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

A compound of the application including pharmaceutically acceptable salts and/or solvates thereof is suitably used on their own but will generally be administered in the form of a pharmaceutical composition in which the one or more compounds of the application (the active ingredient) is in association with a pharmaceutically acceptable carrier. Depending on the mode of administration, the pharmaceutical composition will comprise from about 0.05 wt % to about 99 wt % or about 0.10 wt % to about 70 wt %, of the active ingredient, and from about 1 wt % to about 99.95 wt % or about 30 wt % to about 99.90 wt % of a pharmaceutically acceptable carrier, all percentages by weight being based on the total composition.

III. Methods and Uses of the Application

The compounds of the application, herein defined as covalent immune recruiters (CIRs), have been shown to covalently bind to an antibody and thus irreversibly label the antibody and, in some embodiments, to target a cell.

Accordingly, in an embodiment, the present application includes a method for labelling an antibody for detection, either in a biological sample or in a subject, comprising administering an effective amount of one or more compounds of the application wherein R is a DMD, to the biological sample or subject. In an embodiment, the method for labelling an antibody for detection, allows the quantification of antibodies, such as endogenous antibodies directly in a subject's serum. The ability to detect and quantify antibodies in serum can, for example, be informative in assessing the efficacy of treatments that depend on the concentration of the antibody in the subject.

In an embodiment, the present application includes a use of one or more compounds of the application wherein R is a DMD, for labelling an antibody for detection.

In an embodiment, the compounds of the application bind to and recruit antibodies, such as endogenous antibodies, to the surface of target cells via a ternary complex comprising the antibody and the target binding domain (covalently bonded together) and the target cell. These ternary complexes bind activation receptors on immune cells (e.g. CD64 on monocytes, CD3 receptors on T-cells and CD16α receptors on NK cells) to form quaternary complexes. The result is the activation of endogenous T cell or NK cell cytotoxicity against the target cell. Accordingly, compounds of the application are also effective tools for triggering a cytotoxic response to target cells.

In an embodiment, the present application includes a method for recruiting an antibody for immunotherapy, either in a biological sample or in a subject, comprising administering an effective amount of one or more compounds of the application wherein R is a TBD, to the biological sample or subject.

In an embodiment, the present application includes a method for recruiting an antibody and targeting a cell for provoking an immune response to the cell, either in a biological sample or in a subject, comprising administering an effective amount of one or more compounds of the application wherein R is a TBD, to the biological sample or the subject.

In an embodiment, the present application includes a method for recruiting an antibody naturally present in a subject and targeting a cell, either in a biological sample or the subject, for provoking an immune response to the cell, comprising administering an effective amount of one or more compounds of the application wherein R is a TBD, to the biological sample or the subject.

The present application also includes a method for targeting a cell for provoking an immune response to the cell, either in a biological sample or in a subject, comprising administering an effective amount of one or more compounds of the application wherein R is a TBD, to the biological sample or the subject.

In an embodiment, the present application includes a method for binding tumor antigens in a cell, either in a biological sample or in a subject, comprising administering an effective amount of one or more compounds of the application wherein R is a TBD, to the biological sample or the subject.

In an embodiment, the present application includes a method for provoking cellular phagocytosis of a target cell, either in a biological sample or in a subject, comprising administering an effective amount of one or more compounds of the application wherein R is a TBD, to the biological sample or the subject.

In an embodiment, the present application includes a use of one or more compounds of the application wherein R is a TBD, for at least one of: recruiting an antibody for immunotherapy, recruiting an antibody and targeting a cell for provoking an immune response to the cell, recruiting an antibody naturally present in a subject and targeting a cell for provoking an immune response to the cell, targeting a cell for provoking an immune response to the cell, binding tumor antigens in a cell, and provoking cellular phagocytosis to a target cell.

In an embodiment, the application includes a use of one or more compounds of the application wherein R is a TBD, for the preparation of a medicament for the methods and uses of the present application.

In an embodiment, the present application includes a method of treating a disease, disorder or condition that is treatable by provoking an immune response, comprising administering a therapeutically effective amount of one or more compounds of the application wherein R is a TBD, to a subject in need thereof.

In an embodiment, the present application includes a use of one or more compounds of the application wherein R is a TBD, for treating a disease, disorder or condition treatable by immunotherapy. The application also includes use of one or more compounds of the application wherein R is a TBD, for the preparation of a medicament for treating of a disease, disorder or condition treatable by immunotherapy.

In an embodiment, the disease, disorder or condition treatable by immunotherapy is cancer, therefore the present application includes a method of treating cancer comprising administering a therapeutically effective amount of one or more compounds of the application wherein R is a TBD, to a subject in need thereof. The present application also includes a use of one or more compounds of the application wherein R is a TBD, for treatment of cancer as well as a use of one or more compounds of the application wherein R is a TBD, for the preparation of a medicament for treatment of cancer. The application further includes one or more compounds of the application wherein R is a TBD, for use in treating cancer. In an embodiment, the compound is administered for the prevention of cancer in a subject such as a mammal having a predisposition for cancer.

In an embodiment, the cancer is one that is impacted or treatable by immunotherapy. In an embodiment, the cancer is one that is impacted or treatable by activation of endogenous immune cells. In an embodiment, the cancer is one that is impacted or treatable by provoking an immune response to tumor cells. In an embodiment, the cancer is one that is impacted or treatable by provoking phagocytosis of tumor cells.

In an embodiment, the cancer is selected from, but not limited to: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Metastases of the aforementioned cancers can also be treated in accordance with the methods described herein.

In an embodiment, the cancer is selected from prostate cancer, breast cancer, ovarian cancer and glioblastoma. In an embodiment, the cancer is prostate cancer.

In further embodiments, the present application also includes a method of treating a disease, disorder or condition treatable by immunotherapy, comprising administering to a subject in need thereof a therapeutically effective amount of one or more compounds of the application wherein R is a TBD, in combination with another agent useful for treatment of the disease, disorder or condition treatable by immunotherapy. The present application also includes a use of one or more compounds of the application wherein R is a TBD, in combination with an agent useful for treatment of a disease, disorder or condition treatable by immunotherapy, for treatment of such disease, disorder or condition.

In a further embodiment, the disease, disorder or condition treatable by immunotherapy is cancer and the one or more compounds of the application wherein R is a TBD, are administered in combination with one or more additional cancer treatments. In another embodiment, the additional cancer treatment is selected from radiotherapy, chemotherapy, targeted therapies such as antibody therapies and small molecule therapies such as tyrosine-kinase and serine-threonine kinase inhibitors, immunotherapy, hormonal therapy and anti-angiogenic therapies.

In an embodiment, effective amounts vary according to factors such as the disease state, age, sex and/or weight of the subject. In a further embodiment, the amount of a given compound or compounds that will correspond to an effective amount will vary depending upon factors, such as the given drug(s) or compound(s), the pharmaceutical formulation, the route of administration, the type of condition, disease or disorder, the identity of the subject being treated, and the like, but can nevertheless be routinely determined by one skilled in the art.

In an embodiment, the compounds of the application wherein R is a TBD, are administered at least once a week. However, in another embodiment, the compounds are administered to the subject from about one time per two weeks, three weeks or one month. In another embodiment, the compounds are administered about one time per week to about once daily. In another embodiment, the compounds are administered 2, 3, 4, 5 or 6 times daily. The length of the treatment period depends on a variety of factors, such as the severity of the disease, disorder or condition, the age of the subject, the concentration and/or the activity of the compounds of the application, and/or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration is required. For example, the compounds are administered to the subject in an amount and for duration sufficient to treat the subject.

In an embodiment, the subject is a mammal. In another embodiment, the subject is human.

Compounds of the application wherein R is a TBD, are either used alone or in combination with other known agents useful for treating diseases, disorders or conditions as defined above, such as the compounds disclosed herein. When used in combination with other agents useful in treating such diseases, disorders or conditions, it is an embodiment that a compound of the application wherein R is a TBD, is administered contemporaneously with those agents. As used herein, "contemporaneous administration" of two substances to a subject means providing each of the two substances so that they are both active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion. In an embodiment, a compound of the present application is administered with another therapeutic agent simultaneously or sequentially in separate unit dosage forms or together in a single unit dosage form. Accordingly, the present application provides a single unit dosage form comprising one or more compounds of the application, an additional therapeutic agent, and a pharmaceutically acceptable carrier.

The dosage of a compound of the application wherein R is a TBD, varies depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. In some embodiments, a compound of the application wherein R is a TBD, is administered initially in a suitable dosage that is adjusted as required, depending on the clinical response. Dosages will generally be selected to maintain a serum level of the compound of the application wherein R is a TBD, from about 0.01 µg/cc to about 1000 µg/cc, or about 0.1 µg/cc to about 100 µg/cc. As a representative example, oral dosages of one or more compounds of the application wherein R is a TBD, will range between about 1 mg per day to about 1000 mg per day for an adult, suitably about 1 mg per day to about 500 mg per day, more suitably about 1 mg per day to about 200 mg per day. For parenteral administration, a representative amount is from about 0.001 mg/kg to about 10 mg/kg, about 0.01 mg/kg to about 10 mg/kg, about 0.01 mg/kg to about 1 mg/kg or about 0.1 mg/kg to about 1 mg/kg will be administered. For oral administration, a representative amount is from about 0.001 mg/kg to about 10 mg/kg, about 0.1 mg/kg to about 10 mg/kg, about 0.01 mg/kg to about 1 mg/kg or about 0.1 mg/kg to about 1 mg/kg. For administration in suppository form, a representative amount is from about 0.1 mg/kg to about 10 mg/kg or about 0.1 mg/kg to about 1 mg/kg.

IV. Methods of Preparing the Compounds of the Application

Compounds of the present application can be prepared by various synthetic processes. The choice of particular structural features and/or substituents may influence the selection of one process over another. The selection of a particular process to prepare a given compound of Formula I is within the purview of the person of skill in the art. Some starting materials for preparing compounds of the present application are available from commercial chemical sources. Other starting materials, for example as described below, are readily prepared from available precursors using straightforward transformations that are well known in the art. In the descriptions below showing the preparation of compounds of the application, all variables are as defined in Formula I, unless otherwise stated, In an embodiment, the compounds of the invention may be synthesized using standard chemical connectivity between the linkers (if present), the antibody binding domain (ABD), the antibody labelling domain (ALD) and the target binding domain (TBD)/detection moiety domain (DMD), along with appropriate protecting groups when necessary. In one embodiment, the approach uses standard functional group chemistry in order to link the ABD to the ALD, optionally through a linker, to provide ABD -$(L^1)_n$-ALD, which in turn is linked, optionally through a linker, using standard functional group chemistry to the TBD or DMD to provide compounds of Formula I. Alternatively, in another embodiment, the TBD or DMD groups are first linked, optionally through a linker, using standard functional group chemistry to the ALD to provide ALD-$(L^2)_m$-R (R=TBD or DMD), which is in turn linked, optionally though a linker, using standard functional group chemistry to the ABD to provide compounds of Formula I.

Standard functional group chemistries, that may be used in the preparation of compounds of the application, include, for example, coupling a carboxylic acid to either an amine or an alcohol to generate esters or amides through standard carbodiimide conditions (e.g. DCC, EDCl, DIC) along with base and catalytic amine (e.g. DMAP, imidazole), or by conversion to the acid chloride through oxalyl chloride or thionyl chloride etc., followed by addition of amine/alcohol.

The preparation of the compounds of the application may also include "click" chemistry processes. Click chemistry is used in the art to describe a class of reactions which are often used for attaching a probe or substrate of interest to a specific biomolecule in a process called bioconjugation. This class of biocompatible small molecule reactions may include, for example, [3+2] cycloadditions such as the Huisgen 1,3-dipolar cycloaddition, thiol-ene reactions, Diels-Alder reactions and inverse electron demand Diels-Alder reactions, [4+1] cycloadditions between isonitriles (isocyanides) and tetrazines, nucleophilic substitutions especially to small strained rings like epoxy and aziridines, carbonyl-chemistry-like formation of ureas, addition reactions to carbon-carbon double bonds like dihydroxylation or the alkynes in the thiol-yne reaction. Use of suitable click chemistry would be well within the purview of a person skilled in the art. In some embodiments, the click chemistry is a copper catalyzed reaction of an azide and an alkyne to form a triazole. In some embodiments, the click chemistry is used in the formation of the linker groups $L^1$ and/or $L^2$.

Additionally, for example, an amine or an alcohol may be coupled to an isocyanate or an isothiocyanate to generate ureas, thioureas, or the corresponding carbonates or thiocarbonates.

Still, in a further approach, for example, a heterolinker can be made through treating a nucleophile with the appropriate leaving group. Some leaving groups could be halogens, such as bromine, or sulfonates, such as triflates or tosylates.

The formation of a desired compound salt is achieved using standard techniques. For example, the neutral compound is treated with an acid or base in a suitable solvent and the formed salt is isolated by filtration, extraction or any other suitable method.

The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art. Examples of suitable solvents are ethanol, water and the like. When water is the solvent, the molecule is referred to as a "hydrate". The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

Throughout the processes described herein it is to be understood that, where appropriate, suitable protecting groups will be added to, and subsequently removed from, the various reactants and intermediates in a manner that will be readily understood by one skilled in the art. Conventional procedures for using such protecting groups as well as examples of suitable protecting groups are described, for example, in "*Protective Groups in Organic Synthesis*", T.W. Green, P.G.M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to one skilled in the art. Examples of transformations are given herein, and it is to be understood that the described transformations are not limited only to the generic groups or substituents for which the transformations are exemplified. References and descriptions of other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "*Advanced Organic Chemistry*", March, 4th ed. McGraw Hill (1992) or, "*Organic Synthesis*", Smith, McGraw Hill, (1994). Techniques for purification of intermediates and final products include, for example, straight and reversed phase chromatography on column or rotating plate, recrystallisation, distillation and liquid-liquid or solid-liquid extraction, which will be readily understood by one skilled in the art.

EXAMPLES

The following non-limiting examples are illustrative of the present application.

General Methods for Chemical Synthesis

All chemical reagents and solvents were obtained from commercial suppliers (Sigma Aldrich, Broadpharm, and ThermoFischer) and used without further purification. Thin layer chromatography (TLC) was performed on silica gel precoated aluminium sheets (Silicycle) and visualized by fluorescence quenching, ninhydrin, and potassium permanganate staining. All column chromatography purification was conducted using an rf+ Combi flash ISCO purification system using normal phase silica gel (Silicycle) or reverse phase C18 columns (Teledyne ISCO). 1H, C13, and COSY nuclear magnetic resonance (NMR) spectra were all recorded in deuterated Dimethyl Sulfoxide (DMSO-$d_6$) or deuterated chloroform (CDCl$_3$) on Bruker 600 and 700 (600 and 700 MHz) spectrometers. Chemical shifts were reported in ppm relative to the residual CDCl$_3$ (G 7.26 ppm 1H) or $d_6$-DMSO (G 2.50 ppm $^1$H). NMR chemical shifts were expressed in ppm relative to internal solvent peaks, and coupling constants were measured in Hz. Data are reported as follows: chemical shifts (δ), multiplicity (br=broad, s=singlet, d=doublet, t=triplet, q=quartet, m=multiplet); coupling constant(s) (J) in Hz; integration. Unless otherwise noted, NMR data were collected at 25° C. Electrospray ionization quadrupole Fourier transform mass spectroscopy (ESI-MS) data was obtained using a Waters QUATTRO™ mass spectrometer, while liquid chromatography/mass spectrometry (LCMS) data was obtained on a Agilent-Sciex QTRAP™ system or a LTQ Orbitrap™ XL system using a mobile phase gradient of 95:5 to 5:95 water:ACN over 15 minutes. High resolution electrospray ionization mass spectrometry (HRMS-ESI) was obtained with a BRUKER MicroTOF II mass spectrometer. [M+H] refers to the protonated molecular ion of the chemical species.

Exemplary compounds were prepared using one or more of the synthetic methods outlined in Schemes 1 to 5:

In an embodiment, the compounds of Formula I are prepared as shown in Scheme 1. Therefore, a compound of Formula 8 is obtained from coupling 1-Chloro-2,4-Dinitrobenzene with tertbutyl-Glycine, which is deprotected to produce intermediate 9. Intermediate 9 is reacted with histamine dihydrochloride as shown to lead to intermediate 10. A compound of Formula 11 is produced as shown by coupling Boc-amino-peg 4-alcohol with N,N'-succinimidyl carbonate, and reacted with previously obtained intermediate 10 to lead to intermediate 12. Intermediate 12 may be reacted as shown, with desthiobiotin to produce compound of Formula I CIR 1 (Example 1), or with carboxyfluorescein NHS to produce compound of Formula I CIR 2 (Example 2).

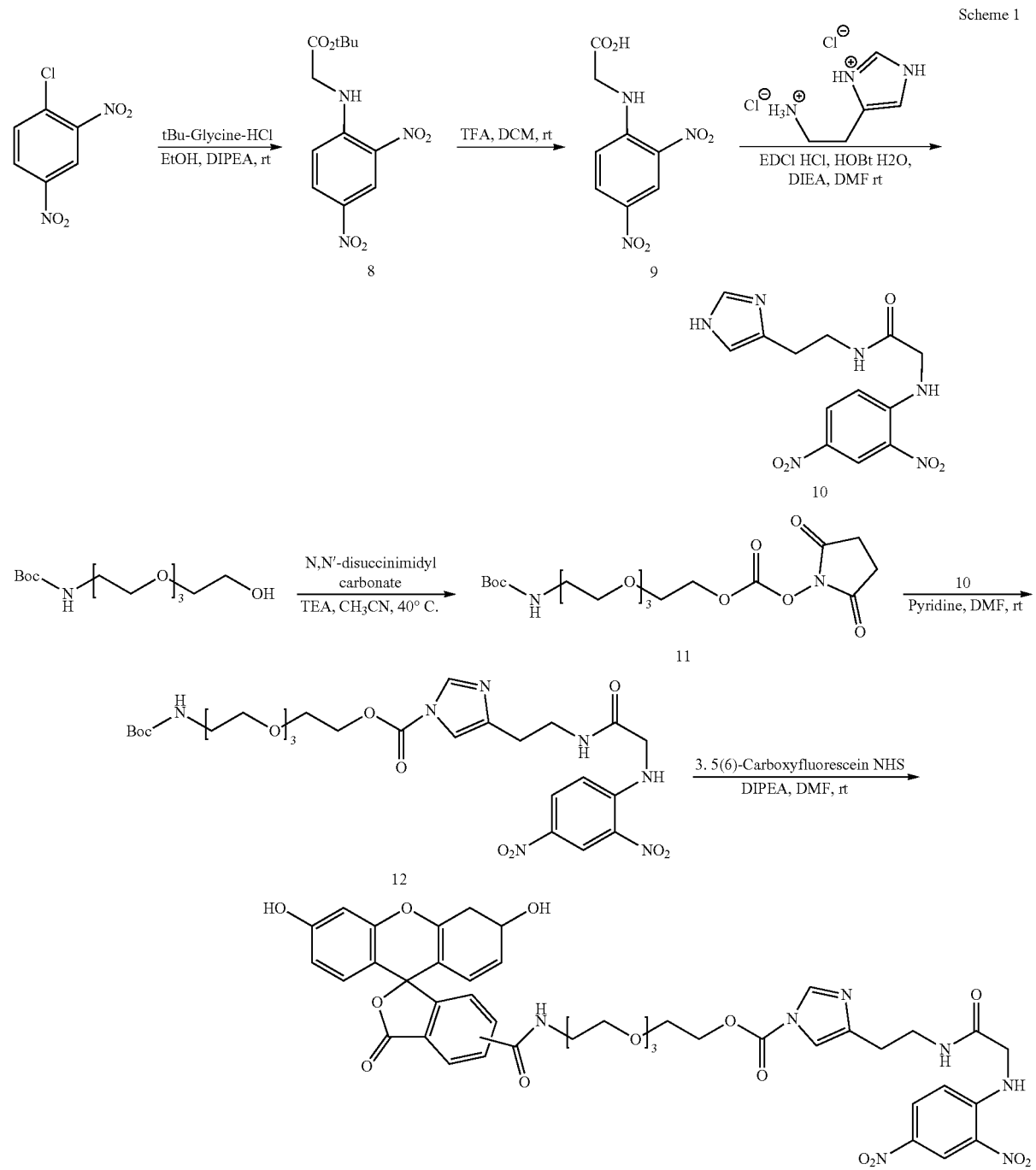

In an embodiment, compounds of Formula I are prepared as shown in Scheme 2. Therefore, an appropriate intermediate 13 is produced by coupling glutamic acid di-tertbutyl ester with N,N'-succinimidyl carbonate. Intermediate 13 is reacted with H-Lys(z)-Otertbutyl hydrochloride to lead to intermediate 14, which is deprotected to give intermediate 15. A succinimidyl leaving group is introduced to give intermediate 16, which is coupled with a polyethylene glycol chain to lead to intermediate 17. Intermediate 17 is coupled to previously obtained intermediate 10 via the introduction of a succinimidyl leaving group to lead to intermediate 18. Finally, in the embodiment shown in Scheme 2, the compound of Formula I CIR 3 (Example 3) is obtained from deprotection of intermediate 18.

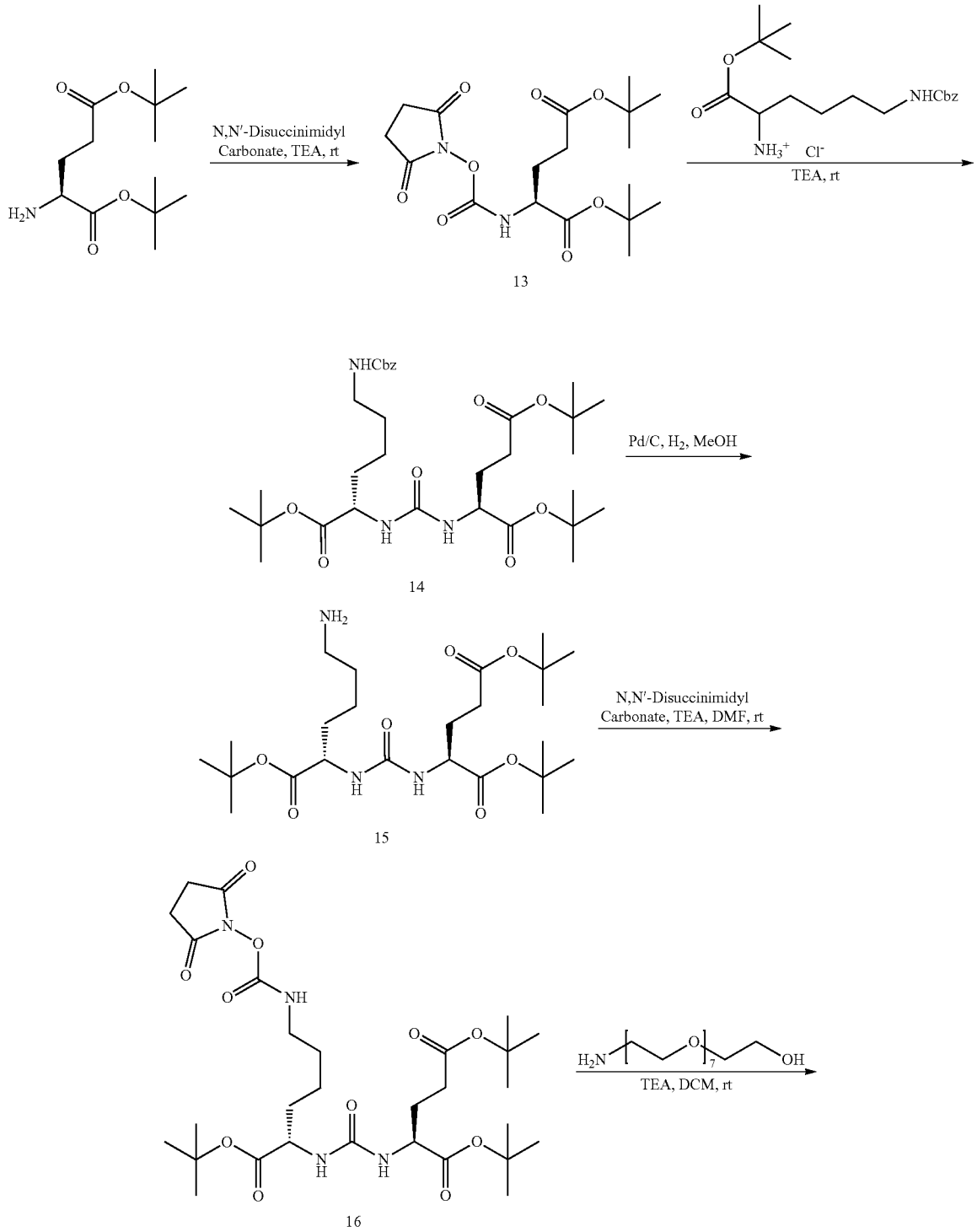

Scheme 2

-continued
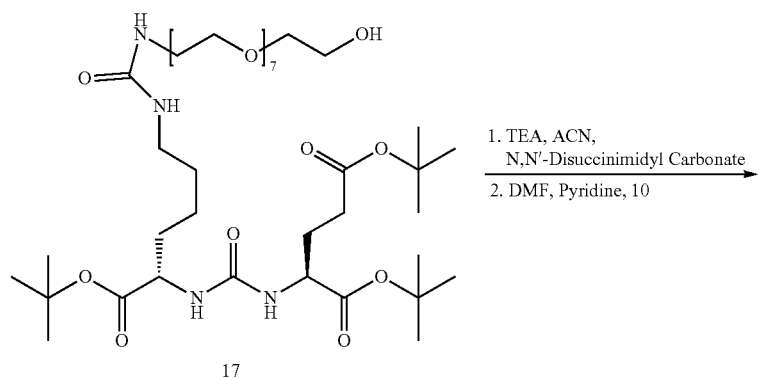
17
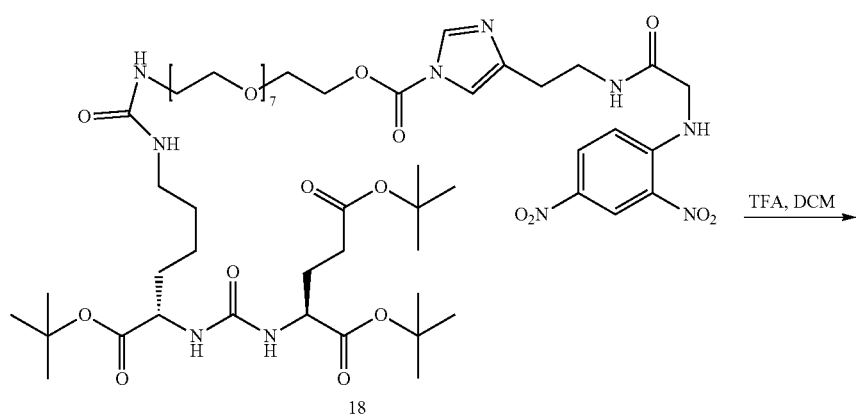
18
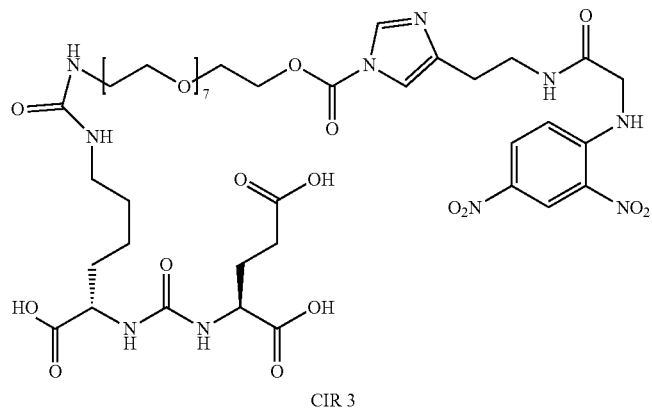
CIR 3
In an embodiment, compounds of Formula I are prepared as shown in Scheme 3. Therefore, intermediates 10 and 11 previously obtained as shown in Scheme 1 are coupled to give intermediate 19. Intermediate 19 is reacted with desthiobiotin to give the compound of Formula I CIR 4 (Example 4).

Scheme 3

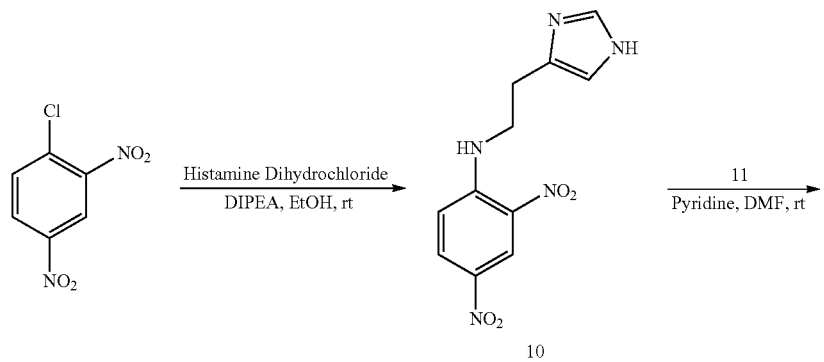

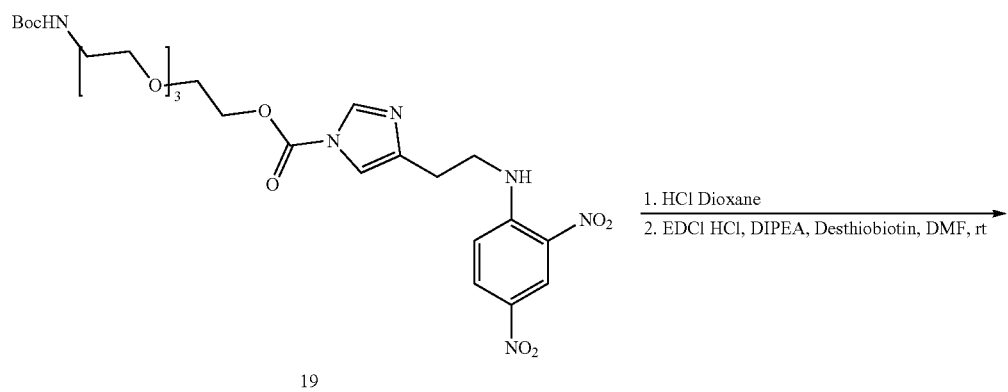

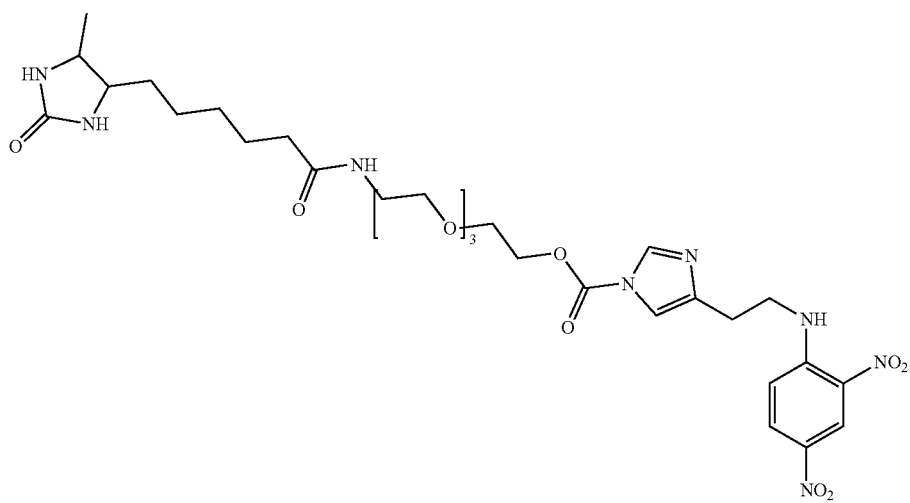

CIR 4

In an embodiment, compounds of Formula I are prepared as shown in Scheme 4 such that ABD, TBD, and ALD domains are modularly assembled via click chemistry in the presence of the labile acylimidazole. Therefore, a succinimidyl leaving group is introduced to 17 from Example 3 to give intermediate 20. Separately, intermediate 22 is produced then combined with 20, followed by 21 to give intermediate 23. In the embodiment shown in Scheme 4, the compound of Formula I CIR 5 (Example 5) is obtained by adding dioxane·HCl to dried intermediate 23.

Scheme 4
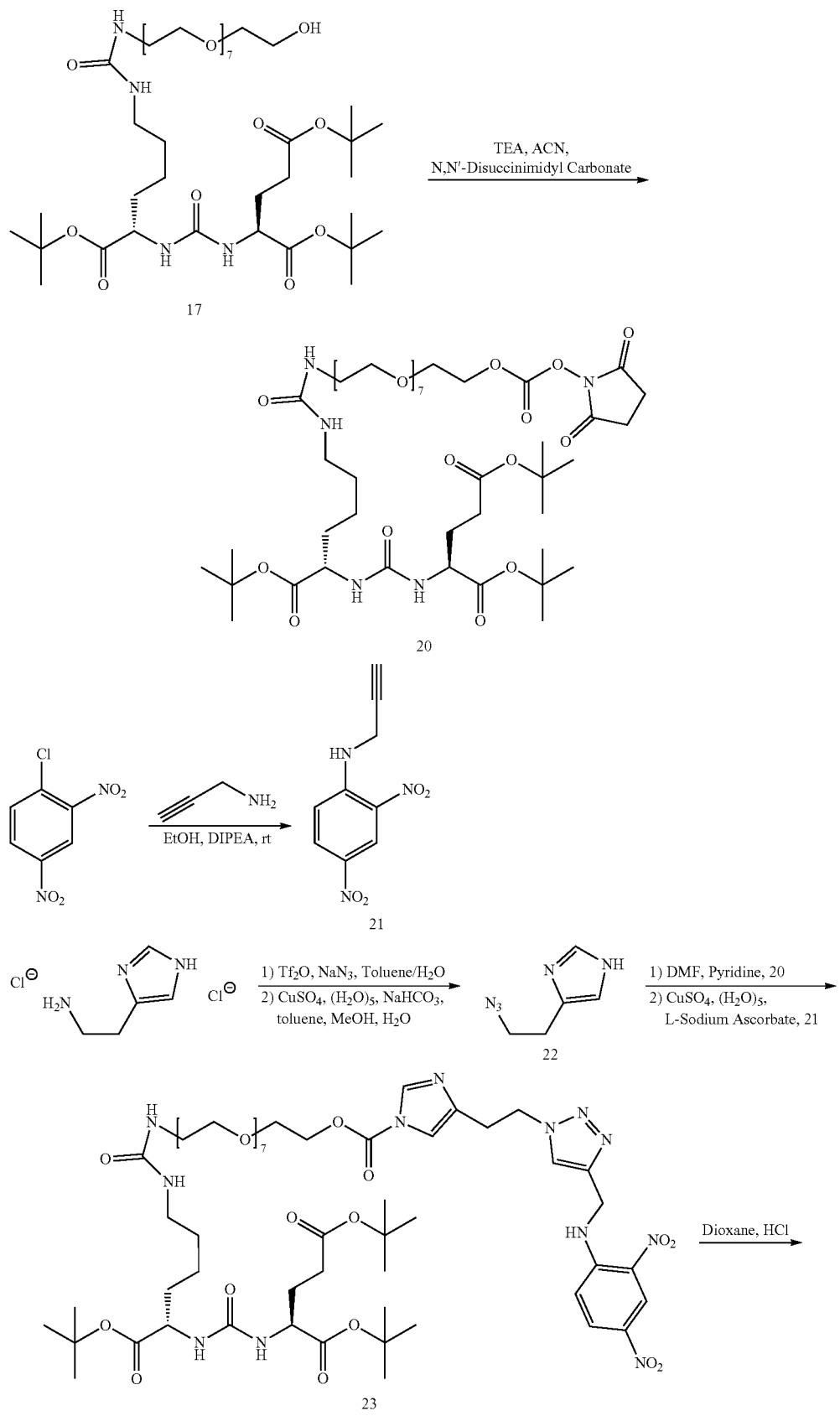

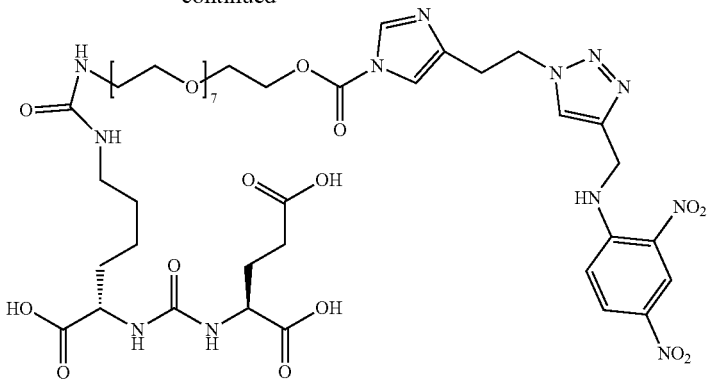
CIR 5
In an embodiment, compounds with non-reactive moiety in place of the antibody labelling domain (ALB), defined as NCIRs, were prepared as Comparative Examples (Scheme 5).
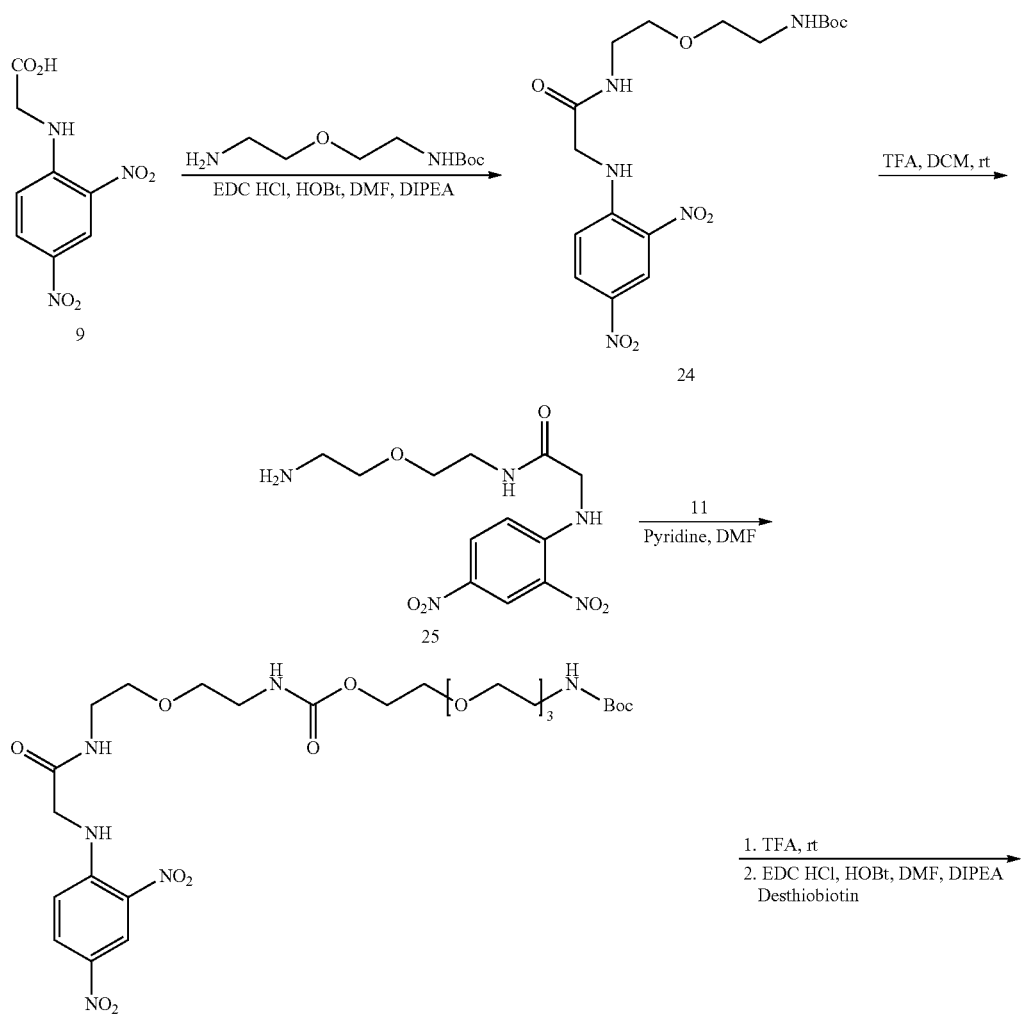

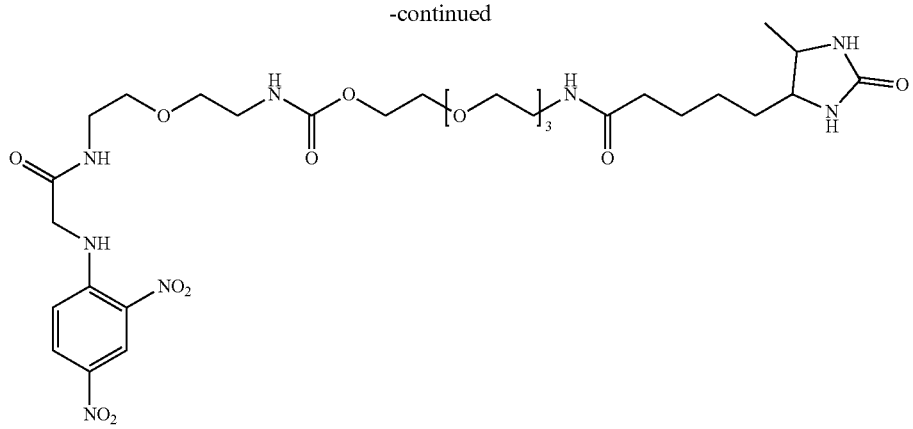
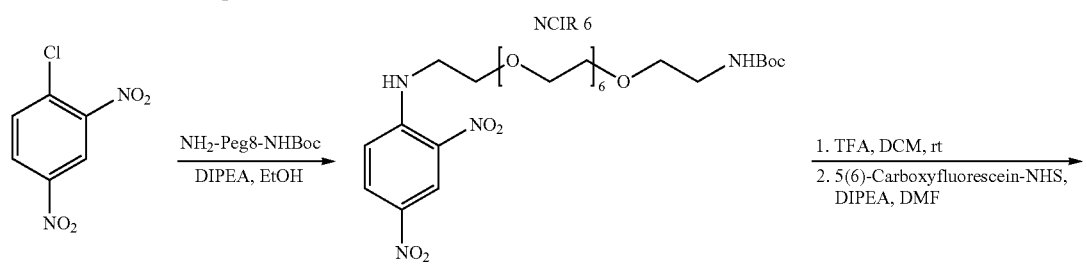
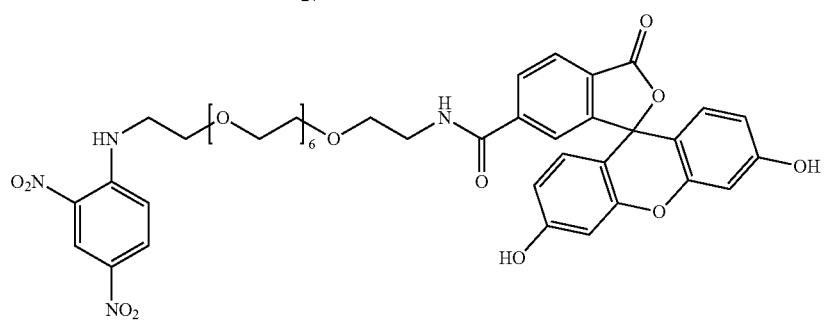
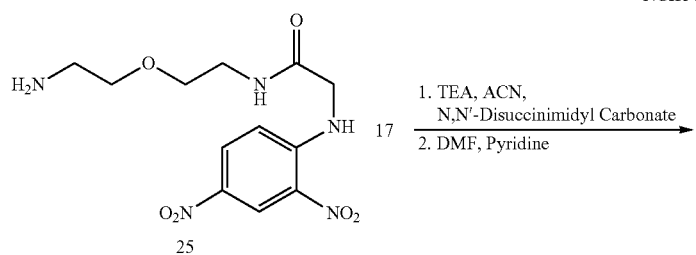
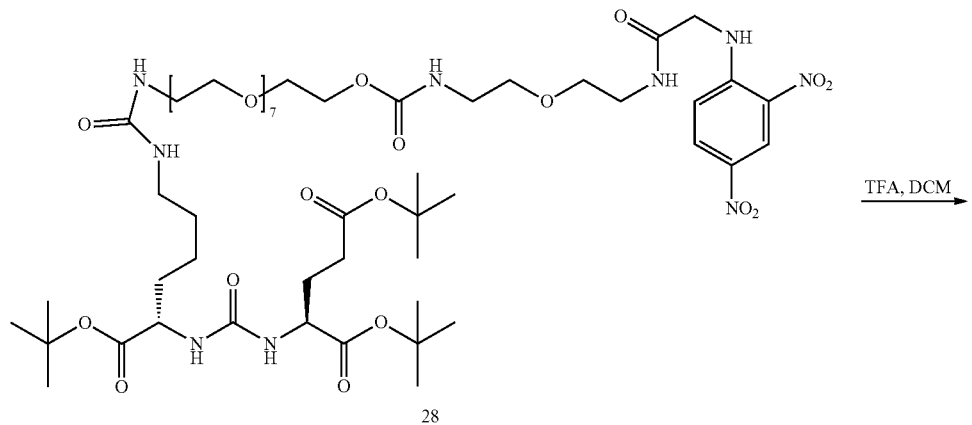

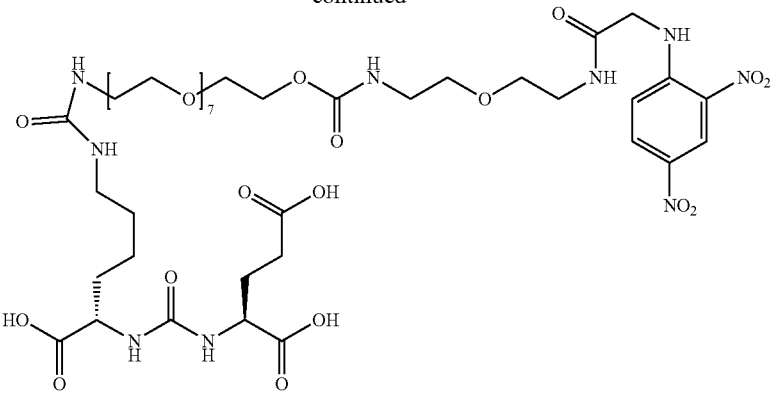

NCIR 8

Example 1: CIR 1 (I-1)

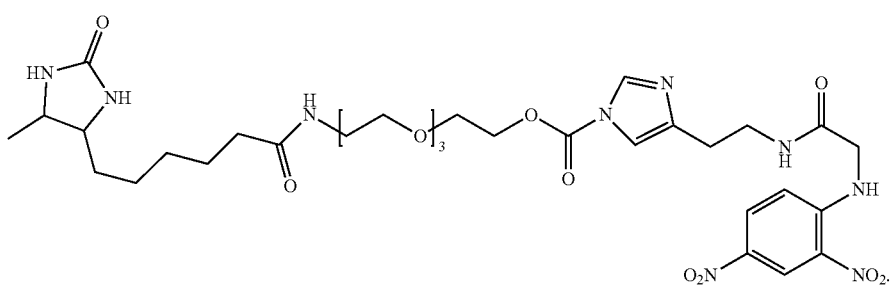

Step 1: Tert-Butyl Ester Derivative (8)

Step 2. Carboxylic Acid Derivative (9)

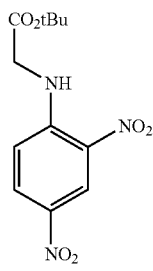 [SMILES: CC(C)(C)OC(=O)CNc1ccc([N+](=O)[O-])cc1[N+](=O)[O-]]

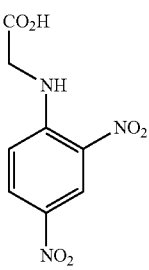 [SMILES: O=C(O)CNc1ccc([N+](=O)[O-])cc1[N+](=O)[O-]]

A solution of 1-Chloro-2,4-Dinitrobenzene (104.4 mg, 0.515 mmol), tButyl-Glycine·HCl (170.2 mg, 1.015 mmol), and N,N-Diisopropylethylamine (382.9 mg, 2.962 mmol) in ethanol (5 mL) was stirred for 20 hours at room temperature. The opaque yellow solution was vacuum filtered, washing with cold ethanol. The filter paper was rinsed with DCM and the resulting product was concentrated in vacuo to yield 8 (121 mg, 78% yield) as a yellow powder. $^1$H NMR (700 MHz, DMSO) δ 8.98 (t, J=5.5 Hz, 1H), 8.88 (d, J=2.7 Hz, 1H), 8.28 (dd, J=4.0 Hz, 1H), 7.09 (d, J=9.6 Hz, 1H), 4.31 (d, J=5.7 Hz, 2H), 1.45 (s, 9H). $^{13}$C NMR (176 MHz, DMSO) δ 168.48, 148.35, 135.94, 130.39, 123.87, 116.41, 82.49, 45.63, 28.17 ppm.

Compound 8 was dissolved in 3 mL DCM and 3 mL TFA and left to stir at room temperature overnight. The DCM/TFA was blown off under a nitrogen stream. The resulting yellow powder was resuspended in 10 mL DCM which was again blown off under nitrogen. The yellow powder was again resuspended in DCM and dried under vacuum to yield 9 (91.7 mg, 93% yield) as a yellow powder. $^1$H NMR (700 MHz, DMSO) δ 9.00 (t, J=5.3 Hz, 1H), 8.87 (d, J=2.7 Hz, 1H), 8.27 (dd, J=4.0 Hz, 1H), 7.10 (d, J=9.5 Hz, 1H), 4.30 (d, J=5.5 Hz, 2H). $^{13}$C NMR (176 MHz, DMSO) δ 170.73, 148.32, 135.85, 130.39, 123.89, 116.53, 45.07 ppm.

Step 3: Imidazole Derivative (10)

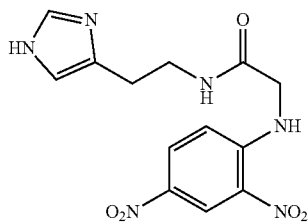 [SMILES: O=C(CNc1ccc([N+](=O)[O-])cc1[N+](=O)[O-])NCCc1c[nH]cn1]

A solution of intermediate 9 (100 mg, 0.494 mmol), Histamine dihydrochloride (183 mg, 0.994 mmol), and DIPEA (1.97 mmol) were combined and stirred at room temperature for 18 hours in 5 ml of ethanol. The material was then concentrated through rotary evaporation giving a yellow solid. This solid was dissolved in about 2 ml of DMF and added dropwise to cold diethyl ether followed by centrifugation to give a yellow/orange oil pellet. This oil was then dissolved in a small amount of DCM:MeOH and loaded onto a silica loading cartridge. This sample was run on a 12 g Telendyne ISCO flash silica column with a gradient increasing from 95:5 to 80:20 DCM:MeOH over 10 minutes and held at this mobile phase composition for another 10 minutes. The pure fractions were pooled and concentrated to yield 10 (59.3 mg, 43% yield) as a pure yellow/orange solid product. $^1$H-NMR (600 MHz, DMSO) δ 8.94 (t, J=5.9 Hz, 1H), 8.85 (d, J=2.7 Hz, 1H), 8.54 (s, 1H), 8.23 (q, J=4.1 Hz, 1H), 7.32 (d, J=9.5 Hz, 1H), 7.32 (s, 1H), 3.79 (q, J=6.6 Hz, 2H), 2.97 (t, J=6.8 Hz, 2H).

Step 4: Carbonate Derivative (11)

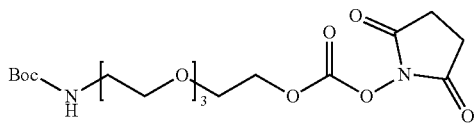

A solution of Boc-Amino-Peg 4-alcohol (200 mg, 0.682 mmol), N,N'-disuccinimidyl carbonate (349 mg, 0.136 mmol), and triethylamine (TEA) (0.19 ml, 0.136 mmol) in 5 ml of ACN was stirred for 2.5 hours at 40° C. The solution was concentrated through rotary evaporation, redissolved in EtOAc and extracted against a solution of saturated sodium bicarbonate, dried over MgSO$_4$, and concentrated via rotary evaporation to yield 11 (198 mg, 67% yield) as a clear colourless oil with minor impurities and used directly in the next step. $^1$H-NMR (600 MHz, DMSO) δ 6.74 (t, J=5.2 Hz, 1H), 4.45 (m, 2H), 3.70 (m, 2H), 3.51 (m, 10H), 3.37 (m, J=6.1 Hz, 2H), 2.81 (s, 4H), 1.37 (s, 9H).

Step 5: Acyl Imidazole Intermediate (12)

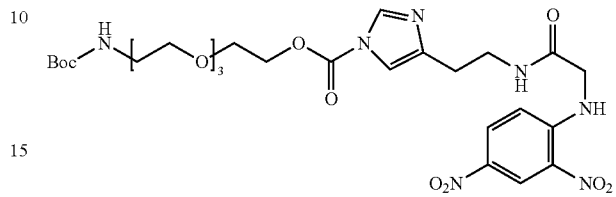

A solution of compound 10 (65 mg, 0.195 mmol), compound 11 (120 mg, 0.276 mmol), and pyridine (0.05 ml, 0.621 mmol) were stirred at room temperature for 18 hours. The reaction mixture was then concentrated in vacuo to yield an orange/yellow oil. A small amount of DCM and a drop of methanol (2-3 ml total) was added to re-solubilize the oil and the solution was loaded onto a 12 g Telendyne ISCO silica flash column. The column was run with a gradient of 95:5 to 80:20 DCM:MeOH over a 20 minute period. The UV positive product fractions were combined and concentrated through rotary evaporation to yield a yellow oil (116.5 mg, 91% yield). This sample was then dissolved in ACN and frozen at −80° C. to prevent any product degradation. $^1$H-NMR (600 MHz, DMSO) δ 9.09 (t, J=5.5 Hz, 1H), 8.87 (d, J=2.7 Hz, 1H), 8.26 (dd, J=4.1 Hz, 1H), 8.24 (t, J=4.4 Hz, 1H), 8.14 (d, J=1.1 Hz, 1H), 7.33 (d, J=1.0 Hz, 1H), 6.91 (d, J=9.7 Hz, 1H), 6.73 (t, J=5.3 Hz, 1H), 4.47 (t, J=4.6 Hz, 2H), 4.18 (t, J=4.6 Hz, 2H), 4.13 (d, J=5.8 Hz, 2H), 3.75 (t, J=4.5 Hz, 2H), 3.51 (m, 12H), 3.04 (q, J=6.8 Hz, 2H), 2.65 (t, J=7.0 Hz, 2H), 1.36 (d, J=6.8 Hz, 9H). $^{13}$C NMR (151 MHz, DMSO) δ 172.78, 167.09, 155.53, 147.77, 140.96, 136.75, 135.19, 129.86, 123.26, 115.63, 113.59, 77.54, 69.77, 69.70, 69.45, 69.13, 67.83, 67.03, 48.57, 45.73, 38.02, 28.18, 27.62, 25.19 ppm.

Step 6

CIR compound 1

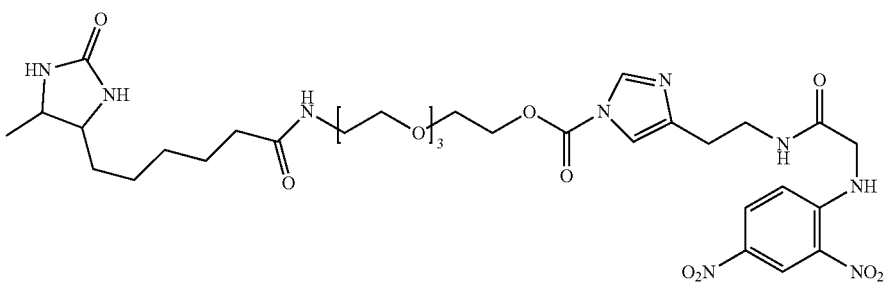

Compound 12 was deprotected immediately before use by dissolving in 5 ml of 4.0 M HCl in dioxane with stirring for 3 hours. After 3 hours most of the product had precipitated out of the HCl dioxane solution, and the remaining product was precipitated out by adding the solution to cold diethyl ether dropwise. The precipitate was collected as a pellet after centrifugation and combined with the precipitate in the reaction vessel to be used directly as crude starting material for the final amide coupling step with desthiobiotin or fluorescein. Crude deprotected compound 12 (61 mg, 0.110 mmol), EDCl HCl (32 mg, 0.167 mmol), DIPEA (0.05 ml, 0.288 mmol), and Desthiobiotin (DTB) (24 mg, 0.112 mmol) were stirred in 5 ml DMF for 15 hours at room temperature. After 15 hours the DMF was removed in vacuo to yield an orange oil. The oil was then dissolved in a small amount of 95:5 DCM:MeOH and loaded onto a Telendyne ISCO silica load cartridge. The product was run on a 12 g Telendyne ISCO silica flash column with a gradient of 95:5 to 80:20 DCM:MeOH over 20 minutes. All the fractions containing product were collected and concentrated to be repurified. A second column was then run. The material was dissolved in water with a small amount of DMSO and loaded onto a Telendyne ISCO Celite™ loading cartridge. The material was run through a 5.5 g reverse phase Telendyne ISCO C18 column with a gradient of 95:5 to 0:100 water: ACN over 15 minutes leading to the successful isolation of pure fractions that were pooled and lyophilized to yield CIR 1 (3.3 mg, 4.4% yield over 2 steps) as a pure yellow solid product. $^1$H-$^1$H COSY was also used to aid in peak assignments. $^1$H NMR (600 MHz, DMSO) δ 9.11 (t, J=5.9 Hz, 1H), 8.88 (d, 2.7 Hz, 1H), 8.27 (dd, J=6.7 Hz, 2H), 8.16 (s, 1H), 7.83 (t, J=5.6 Hz, 1H), 7.34 (s, 1H), 6.92 (d, J=9.5 Hz, 1H), 6.31 (s, 1H), 6.13 (s, 1H), 4.47 (m, 2H), 4.14 (m, 2H), 3.76 (m, 2H), 3.58 (m, 12H) 3.17 (q, J=5.7 Hz, 2H), 2.65 (t, J=7.2 Hz, 2H), 2.04 (t, J=7.3 Hz, 2H), 1.46 (m, 2H), 1.24 (m, 6H), 0.95 (d, J=6.4 Hz, 9H). $C_{32}H_{47}N_9O_{12}$, Expected Exact Mass=749.33442, Calculated [M+H]$^+$=750.39728.

Example 2: CIR 2 (1-2)

Step 1: 5(6)-Carboxyfluorescein N-hydroxysuccinimide Ester

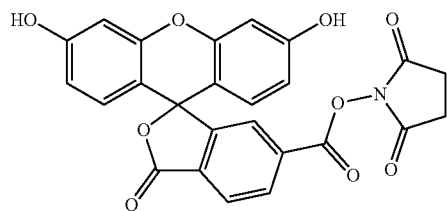 [SMILES: O=C(ON1C(=O)CCC1=O)c1ccc2c(c1)C1(OC2=O)c2ccc(O)cc2Oc2cc(O)ccc21]

As a reactant to be used in step 2, 5/6 carboxy fluorescein NHS was prepared. 5/6 Carboxy fluorescein (1.0 g, 2.66 mmol) was dissolved in 10 mL anhydrous DMF followed by the addition of EDC·HCl (662.2 mg, 3.45 mmol) and N-hydroxysuccinimide (366.9 mg, 3.19 mmol) in a nitrogen atmosphere. After 24 hours stirring, the solution was diluted with 40 mL acetone and 50 mL phosphate buffer (0.05M, pH 5.96). This was then washed with diethyl ether:Ethyl Acetate (2:1). The organic layer was then washed with water followed by brine. The organic layer was then dried over anhydrous magnesium sulphate. The solvent was removed under vacuum to yield 1.0724 g crude product. 87.8 mg was removed and purified by flash silica column chromatography (100% DCM—80% DCM/20% MeOH) to yield crude product (67.0 mg, 65.1% yield) as a red powder. $^1$H NMR (600 MHz, DMSO) δ 10.19 (s, 2H), 8.54 (s, 0.5H), 8.41 (d, J=3.2 Hz, 0.5H), 8.37 (dd, J=3.1 Hz, 0.5H), 8.24 (d, J=8.1 Hz, 0.5H), 7.90 (s, 0.5H), 7.55 (d, J=8.0 Hz, 0.5H), 6.68 (m, J=4.9 Hz, 6H), 4.08 (q, J=5.3 Hz, 1H), 3.16 (d, J=5.3 Hz, 2H), 2.89 (d, J=36.2 Hz, 4H).

Step 2: CIR 2

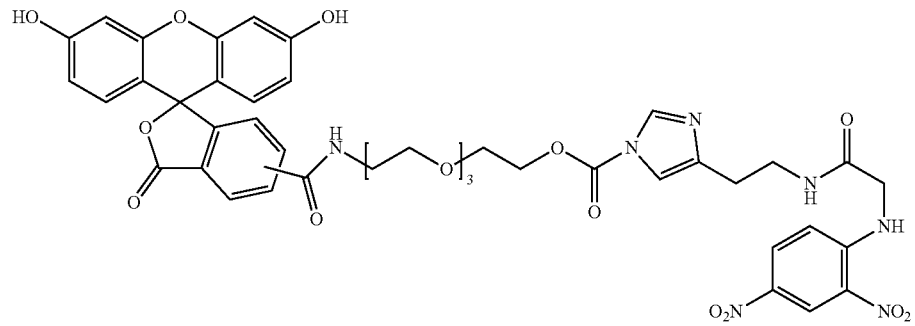

Compound 12 was deprotected according to a procedure similar to step 6 of Example 1. A solution of deprotected compound 12 (25 mg, 0.0452 mmol), DIPEA (12 uL, 0.0688 mmol), and 5(6)-Carboxyfluorescein N-hydroxysuccinimide ester obtained in step 1 (32 mg, 0.0676 mmol) were combined in 3 mL of DMF, and stirred at room temperature for 18 hours while covered from light. Next 2×1.5 ml of the reaction solution was added dropwise to 2×40 ml of cold diethyl ether, resulting in the separation of a yellow/orange oil. The samples were centrifuged and the resulting oil layer isolated and combined. The oil was dissolved in minimal ACN to which water was added prior to loading on a Telendyne ISCO Celite load cartridge and purification using a 5.5 g Telendyne ISCO C18 column with a gradient of 90:10 to 0:100 water:ACN over 30 min. The product containing yellow coloured fractions confirmed by LC-MS, were pooled and dried via rotary evaporation yielding pure CIR 2 as a yellow-orange oil, in low (mg) quantities sufficient for subsequent antibody labeling studies. $^1$H-NMR (600 MHz, DMSO) δ 9.09 (t, J=5.3 Hz, 1H), 8.87 (d, J=2.8 Hz, 2H), 8.45 (s, 1H), 8.39 (s, 2H), 8.28 (s, 1H) 8.24 (dd, J=4.1 Hz, 1H), 8.21 (d, J=8.7 Hz, 1H), 8.14 (d, J=1.1 Hz, 1H), 7.35 (d, J=7.9 Hz, 1H), 7.32 (s, 1H), 6.90 (d, J=9.4 Hz, 1H), 6.59 (d, J=8.6 Hz, 2H), 6.53 (dd, J=8.4 Hz, 2H), 6.28 (s, 2H), 4.45 (m, 2H), 4.12 (d, J=5.5 Hz, 2H), 3.73 (m, 2H), 3.52 (m, 16H), 2.64 (t, J=6.9 Hz, 2H). $C_{43}H_{41}N_7O_{16}$, Expected Exact Mass=911.26098, Calculated [M+2H]$^{2+}$=456.65454.

Example 3: CIR 3 (I-3)

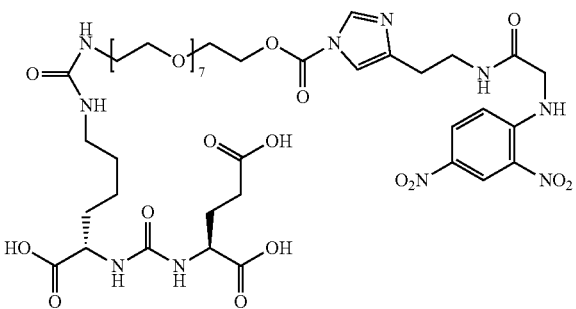

Step 1: Carbamate Derivative 13

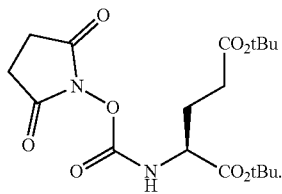 [SMILES: CC(C)(C)OC(=O)CC[C@H](NC(=O)ON1C(=O)CCC1=O)C(=O)OC(C)(C)C]

L-Glutamic acid di-t-Butyl ester (400 mg, 1.352 mmol) was dissolved in acetonitrile (5.3 mL). N,N'-Disuccinimidyl carbonate (416 mg, 1.623 mmol) was added to this mixture followed by triethylamine (226 uL, 1.623 mmol). After 9 hours of stirring the solvent was removed under vacuum, and the crude mixture was redissolved in EtOAc. The supernatant was washed with a 10% citric acid solution followed by brine. The organic layer was dried over anhydrous $Mg_2SO_4$ and concentrated under vacuum to yield 13 (443.6 mg, 81.9% yield) as a clear oil. $^1$H NMR (600 MHz, $CDCl_3$) δ 6.04 (d, J=7.4 Hz, 1H), 4.23 (m, J=4.1 Hz, 1H), 2.33 (m, J=6.4 Hz, 3H), 2.15 (m, J=5.7 Hz, 1H), 2.00 (m, J=7.2 Hz, 1H), 1.48 (s, 9H), 1.45 (s, 9H). $^{13}$C NMR (151 MHz, $CDCl_3$) δ 171.97, 169.60, 150.98, 83.21, 81.01, 54.78, 31.12, 27.87, 25.47 ppm.

Step 2: Cbz Protected Intermediate 14

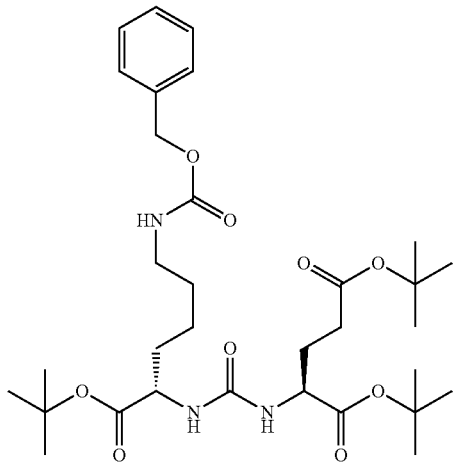 [SMILES: CC(C)(C)OC(=O)CC[C@H](NC(=O)N[C@@H](CCCCNC(=O)OCc1ccccc1)C(=O)OC(C)(C)C)C(=O)OC(C)(C)C]

Compound 13 (430 mg, 1.074 mmol) was dissolved in DCM (9 mL). H-Lys(z)-OtButyl Hydrochloride (450 mg, 1.21 mmol) was added followed by triethylamine (309 uL, 2.22 mmol). After stirring overnight the solvent was removed under vacuum and the resulting crude mix was purified by flash silica column chromatography (100% DCM—80% DCM/20% MeOH) to yield 14 (443.2 mg, 64.3% yield) as a clear oil. $^1$H NMR (700 MHz, $CDCl_3$) δ 7.35 (d, J=2.7 Hz, 5H), 5.08 (m, J=12.0 Hz, 5H), 4.33 (q, J=4.3 Hz, 2H), 3.18 (t, J=6.5 Hz, 2H), 2.29 (m, J=6.0 Hz, 2H), 2.06 (m, J=5.7 Hz, 1H), 1.84 (m, J=6.7 Hz, 1H), 1.76 (m, J=4.4 Hz, 1H), 1.63 (m, 1H), 1.52 (m, J=5.7 Hz, 2H), 1.44 (t, J=7.4 Hz, 27H), 1.36 (m, J=39.6 Hz, 2H). $^{13}$C NMR (176 MHz, $CDCl_3$) δ 172.35, 156.70, 136.70, 128.26, 81.95, 80.54, 66.57, 53.16, 40.63, 32.65, 31.59, 29.35, 28.36, 28.05, 22.20 ppm.

Step 3: Amine Intermediate 15

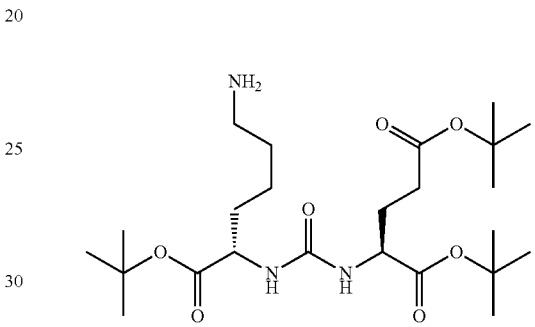

Compound 14 (220 mg, 0.353 mmol) was dissolved in 3 mL of MeOH and stirred with 20 mg Pd/C under $H_2$ atmosphere overnight. The reaction was filtered through Celite and concentrated under vacuum. This product was then purified via Telendyne ISCO flash C18 column chromatography to yield 15 (154.5 mg, 89.8% yield) as a clear oil. $^1$H NMR (600 MHz, $CDCl_3$) δ 4.94 (t, J=6.6 Hz, 2H), 4.33 (m, J=4.2 Hz, 3H), 2.67 (t, J=6.8 Hz, 2H), 2.29 (m, J=6.4 Hz, 2H), 2.06 (m, J=4.7 Hz, 1H), 1.86 (m, J=4.9 Hz, 1H), 1.77 (m, J=4.7 Hz, 1H), 1.62 (m, J=4.3 Hz, 2H), 1.46 (s, 18H), 1.43 (s, 9H), 1.33 (m, J=7.0 Hz, 2H).

Step 4: Carbamate Intermediate 16

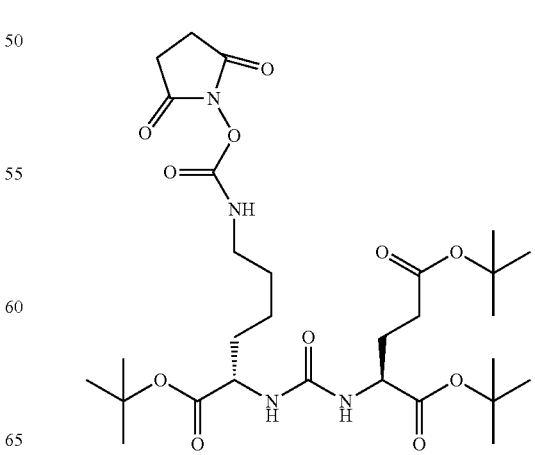

Compound 15 (154.5 mg, 0.317 mmol) was dissolved in 2 mL of toluene and dried under vacuum, backfilled with nitrogen, and re-dissolved in 14.3 mL anhydrous DMF. Next, N,N'-Disuccinimidyl Carbonate (90 mg, 0.349 mmol) was added followed by TEA (55 uL, 0.317 mmol) and the solution was left stirring overnight. The reaction solution was then diluted with 50 mL EtOAc and washed with a 10% citric acid solution followed by brine. The organic layer was dried over anhydrous $Mg_2SO_4$ and concentrated under vacuum. The crude product was purified via flash silica gel column chromatography (3:1 EtOAc/Hexanes) to yield 16 (53.2 mg, 26.7% yield) as a clear oil. $^1$H NMR (700 MHz, $CDCl_3$) δ 6.62 (s, 1H), 5.55 (d, J=8.0 Hz, 2H), 5.46 (d, J=8.3 Hz, 2H), 4.31 (m, J=4.1 Hz, 2H), 3.24 (m, J=7.6 Hz, 2H), 2.83 (s, 4H), 2.28 (m, J=5.4 Hz, 2H), 2.02 (s, 1H), 1.80 (m, J=4.6 Hz, 1H), 1.74 (m, J=4.8 Hz, 1H), 1.60 (m, J=4.6 Hz, 1H), 1.54 (m, J=7.0 Hz, 1H), 1.43 (s, 9H), 1.43 (s, 9H), 1.41 (s, 9H), 1.35 (m, J=6.1 Hz, 1H). $^{13}$C NMR (176 MHz, $CDCl_3$) δ 172.45, 157.33, 151.87, 81.99, 81.42, 80.44, 60.40, 53.08, 42.71, 41.46, 31.79, 28.50, 25.53, 21.76, 21.05, 14.19 ppm.

Step 5: Alcohol Derivative 17

Step 6: Acyl Imidazole Intermediate 18

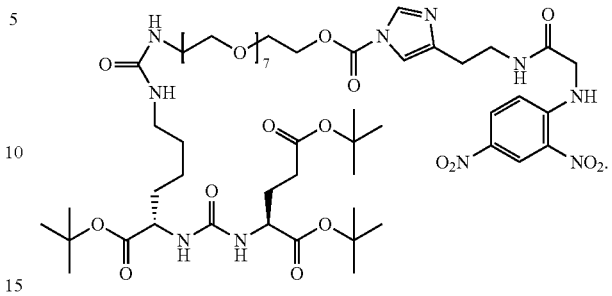

Compound 17 (37 mg, 0.043 mmol) and N,N'-Disuccinimidyl Carbonate (22 mg, 0.085 mmol) were mixed and dissolved in 2 mL of toluene then concentrated to dryness under vacuum and backfilled with nitrogen. The residue was then resuspended in 1.7 mL anhydrous ACN followed by the addition of TEA (12 uL, 0.085 mmol). After 3 hours of stirring, the solution was diluted with EtOAc (50 mL) and washed with sat. $NaHCO_3$(aq). The organic layer was dried

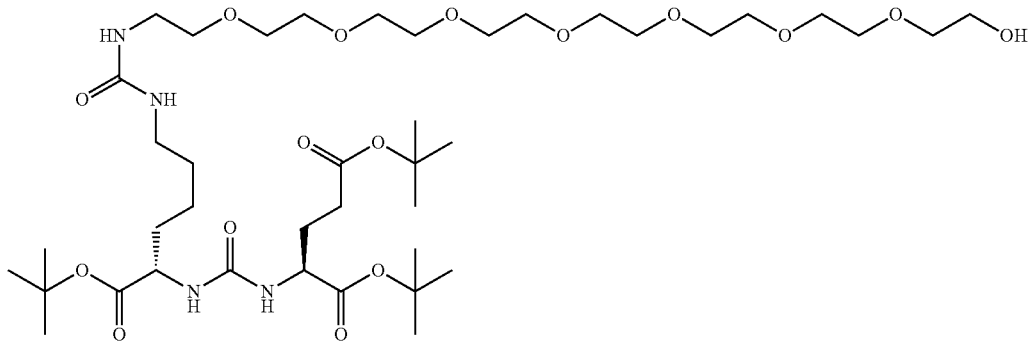 [SMILES: CC(C)(C)OC(=O)CC[C@H](NC(=O)N[C@@H](CCCCNC(=O)NCCOCCOCCOCCOCCOCCOCCOCCO)C(=O)OC(C)(C)C)C(=O)OC(C)(C)C]

Compound 16 (38 mg, 0.06 mmol) was dissolved in 2 mL of toluene and dried under vacuum then backfilled with a nitrogen environment. In parallel, Hydroxy-PEG8-Amine (35 mg, 0.09 mmol) was dissolved in 2 mL of toluene and dried under vacuum then backfilled with nitrogen. Compound 16 was then dissolved in 1 mL anhydrous DCM and added to the Hydroxy-PEG8-Amine followed by TEA (13 uL, 0.07 mmol). After overnight stirring the solution was diluted with DCM (20 mL) and washed with brine. The organic layer was dried over anhydrous $Mg_2SO_4$ and concentrated under vacuum to yield crude 17 (37.2 mg, 69.1% yield) as a clear oil. $^1$H NMR (700 MHz, $CDCl_3$) δ 5.72 (d, J=7.6 Hz, 1H), 5.60 (d, J=8.1 Hz, 1H), 5.54 (t, J=5.3 Hz, 1H), 5.39 (s, 1H), 4.31 (m, J=4.3 Hz, 1H), 4.22 (m, J=4.0 Hz, 1H), 3.71 (s, 2H), 3.63 (m, J=3.8 Hz, 60H), 3.53 (m, J=4.4 Hz, 2H), 3.34 (t, J=5.0 Hz, 2H), 3.20 (m, J=6.7 Hz, 2H), 3.10 (m, J=6.2 Hz, 2H), 2.29 (m, J=5.4 Hz, 4H), 2.04 (m, J=4.3 Hz, 1H), 1.82 (m, J=4.0 Hz, 1H), 1.73 (m, J=4.1 Hz, 1H), 1.62 (m, J=4.1 Hz, 1H), 1.44 (s, 9H), 1.43 (s, 9H), 1.42 (s, 9H), 1.35 (m, J=4.2 Hz, 2H), 1.24 (s, 2H).

under vacuum then resuspended in 2 mL toluene, concentrated to dryness and the flask backfilled with nitrogen. In parallel, Compound 10 (35 mg, 0.105 mmol) was toluene dried and backfilled with nitrogen. Compound 10 was then dissolved in 1.7 mL anhydrous DMF and added to Compound 17. Pyridine (20 uL, 0.249 mmol) was then added to this solution. After overnight stirring the solution was diluted with EtOAc (10 mL) and washed with brine. The organic layer was dried over anhydrous $Mg_2SO_4$ and concentrated under vacuum. This crude product was further purified via Telendyne ISCO flash C18 column chromatography and product extracted from aqueous fraction using EtOAc, with organic layers concentrated to dryness to yield Compound 18 (37.2 mg, 69.1% yield) as a clear oil. $^1$H NMR (700 MHz, DMSO) δ 9.09 (t, J=5.5 Hz, 1H), 8.87 (d, J=2.7 Hz, 1H), 8.25 (m, J=4.7 Hz, 2H), 8.14 (d, J=1.2 Hz, 1H), 7.32 (d, J=1.0 Hz, 1H), 6.91 (d, J=9.6 Hz, 1H), 6.27 (dd, J=9.8 Hz, 2H), 5.89 (t, J=5.6 Hz, 1H), 5.78 (t, J=5.7 Hz, 1H), 4.46 (m, J=2.3 Hz, 2H), 4.13 (d, J=5.6 Hz, 2H), 4.03 (m, J=4.4 Hz, 1H), 3.94 (m, J=4.3 Hz, 1H), 3.74 (m, J=2.3 Hz, 2H), 3.57 (m, J=3.2 Hz, 2H), 3.49 (m, J=3.4 Hz, 22H), 3.36 (m, J=4.4 Hz, 4H), 3.11 (q, J=5.8 Hz, 2H), 2.94 (m, J=4.9 Hz, 2H), 2.64 (t, J=7.0 Hz, 2H), 2.21 (m, J=5.7 Hz, 2H), 1.86 (m, J=6.7 Hz, 1H), 1.65 (m, J=8.1 Hz, 1H), 1.58 (m, J=8.0 Hz, 1H), 1.49 (m, J=7.1 Hz, 2H), 1.39 (s, 9H), 1.38

(s, 9H), 1.38 (s, 9H), 1.33 (m, J=3.5 Hz, 2H), 1.24 (m, J=8.1 Hz, 2H). $^{13}$C NMR (176 MHz, DMSO) δ 172.72, 172.35, 171.88, 167.59, 158.41, 157.56, 148.70, 148.27, 141.46, 137.24, 135.68, 130.36, 123.76, 116.13, 114.08, 81.06, 80.74, 80.21, 68.31, 67.53, 53.55, 52.60, 46.22, 38.52, 32.26, 31.33, 30.23, 28.19, 22.97 ppm.

Step 7: CIR 3

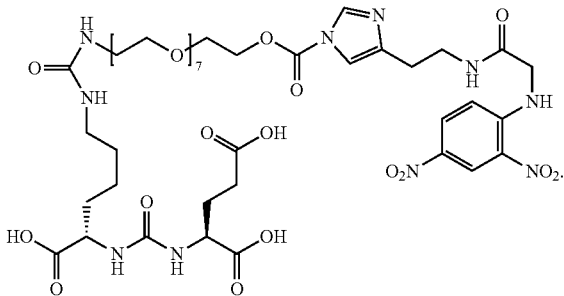

Acyl imidazole intermediate 18 (30 mg) was dissolved in 3 mL Dioxane:HCl (4M) under argon and spun for 4 hours. The solution was then diluted with DCM and dried under vacuum. This was then purified by HPLC to yield CIR 3 as a clear oil in analytical quantities sufficient for preparation of mM stock solutions for in vitro assays. $^1$H NMR (700 MHz, DMSO) δ 9.11 (s, 1H), 8.88 (d, J=2.7 Hz, 1H), 8.29 (m, J=9.7 Hz, 3H), 8.15 (s, 1H), 7.34 (s, 1H), 6.93 (d, J=9.6 Hz, 1H), 6.57 (s, 3H), 6.42 (s, 1H), 6.19 (s, 1H), 5.93 (d, J=33.0 Hz, 2H), 4.47 (d, J=4.6 Hz, 2H), 4.15 (d, J=5.5 Hz, 2H), 3.97 (s, 2H), 3.75 (d, J=4.5 Hz, 2H), 3.58 (d, J=5.2 Hz, 2H), 3.50 (t, J=4.7 Hz, 24H), 3.13 (t, J=5.7 Hz, 2H), 2.94 (d, J=6.0 Hz, 2H), 2.66 (t, J=7.0 Hz, 2H), 2.29 (m, 2H), 2.14 (d, J=13.4 Hz, 2H), 1.85 (s, 1H), 1.61 (s, 2H), 1.47 (s, 1H), 1.32 (t, J=7.0 Hz, 2H), 1.25 (d, J=15.4 Hz, 2H).

Example 4. CIR 4 (I-4)

Step 1: Acyl Imidazole Intermediate 19

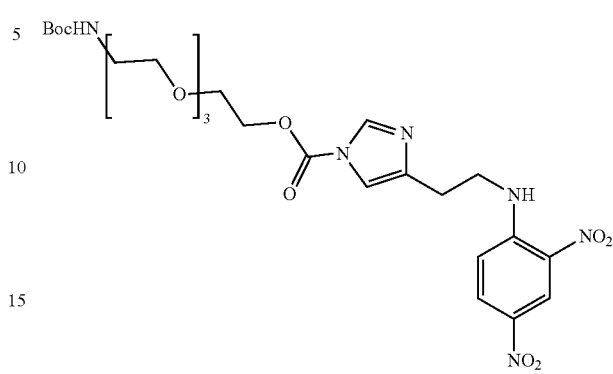

Compounds 10 and 11 were obtained from a procedure similar to Example 1, Steps 3 and 4, respectively. A solution of compound 10 (55 mg, 0.198 mmol), pyridine (52 uL, 0.646 mmol), and compound 11 (100 mg, 0.230 mmol) were stirred in 3 ml of DMF for 15 hours. The DMF was then removed on a high-pressure vacuum producing a yellow/orange oil. This was then dissolved in a small amount of DCM:MeOH and loaded onto a silica load cartridge. A 12 g Telendyne ISCO silica flash column was used to purify the crude product using a gradient of 95:5 to 80:20 DCM:MeOH over 10 minutes. The fractions containing yellow product were combined and validated via LC-MS indicating compound 11 impurity was still present. Impure compound 19 was concentrated by rotary evaporation and the resulting yellow oil was dissolved in a small amount of 70:30 water:ACN mixture. The product solution was purified on a 5.5 g Telendyne ISCO reverse phase C18 column using a gradient of 65:35 to 0:100 water:ACN over 16 minutes. The fractions containing yellow product were collected and analyzed by LCMS to confirm pure product. The fractions were concentrated using rotary evaporation yielding compound 19 (24 mg, 20.2% yield) as a yellow oil.

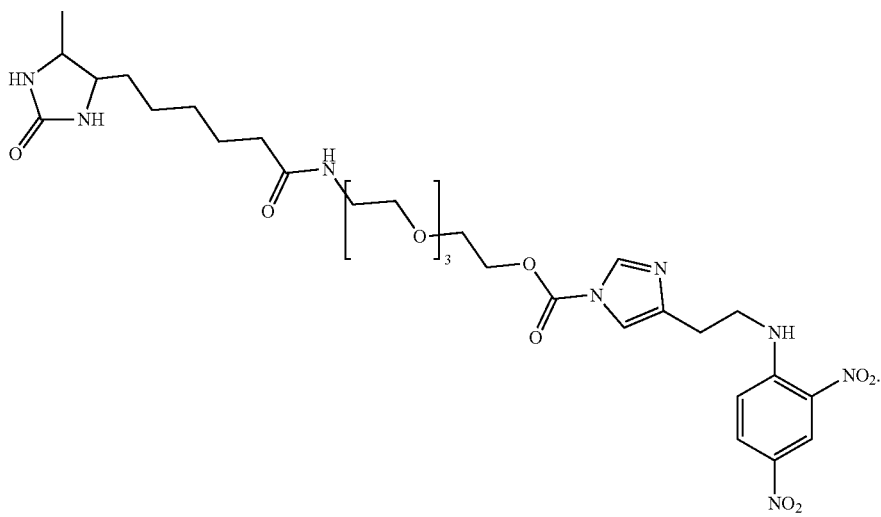

Step 2: CIR 4

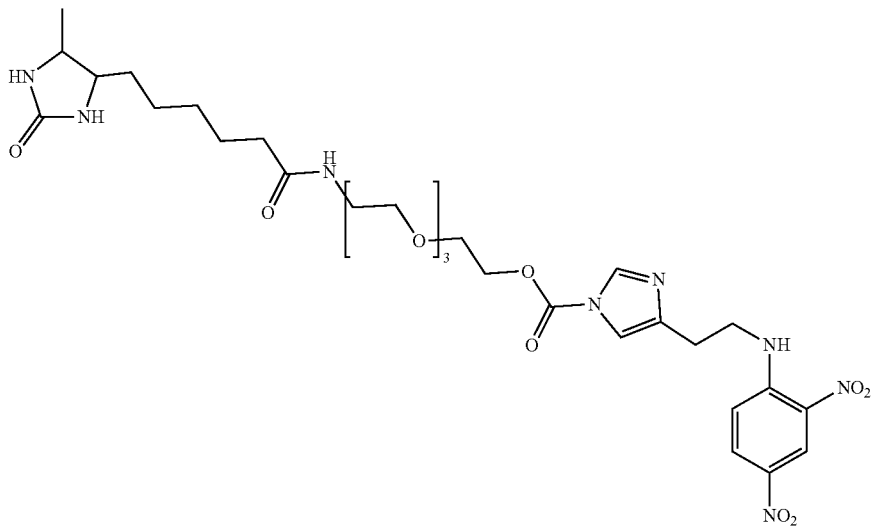

Intermediate 19 (24 mg, 0.04 mmol) was stirred in 3 mL of 4.0M HCl in dioxane at room temperature for 1 hour. The yellow oil product precipitated out of the solution with remaining product precipitated from solution when adding dropwise to cold diethyl ether. The oil fractions were then combined and dried under vacuum for 10 minutes before use in the final dimerizer synthesis. Deprotected crude intermediate 19 (20 mg, 0.04 mmol), EDCl HCl (14 mg, 0.07 mmol), DIPEA (22 uL, 0.01 mmol), and DTB (11 mg, 0.051 mmol) were stirred for 15 hours at room temperature in 3 mL of DMF. The DMF was then removed using a high-pressure vacuum, giving rise to a yellow/orange oil. This was then dissolved in a small amount of ACN followed by water to reach a final loading volume of 3 ml which was added to a 5.5 g Telendyne ISCO C18 flash column and run using a gradient of 85:15 to 0:100 water:ACN over 20 minutes. The product fractions were confirmed via LC-MS, pooled and lyophilized to give 9.3 mg of CIR 4 (33.3% yield). $^1$H-NMR (600 MHz, DMSO) δ 8.96 (t, J=5.8 Hz, 1H), 8.85 (d, J=2.7 Hz, 1H), 8.26 (q, J=4.0 Hz, 1H), 8.22 (d, J=1.3 Hz, 1H), 7.80 (t, J=5.7 Hz, 1H), 7.51 (d, J=1.0 Hz, 1H), 7.26 (d, J=9.7 Hz, 1H), 6.28 (s, 1H), 6.11 (s, 1H), 4.48 (t, J=4.5 Hz, 2H), 3.75 (s, 4H), 3.58 (m, 14H) 3.16 (q, J=5.8 Hz, 2H), 2.89 (t, J=6.9 Hz, 2H), 2.03 (t, J=7.4 Hz, 2H), 1.45 (m, 2H), 1.31 (m, 7H), 0.94 (d, J=6.2 Hz, 3H). $C_{30}H_{44}N_8O_{11}$, Expected Exact Mass=692.31295, Calculated [M+H]$^+$=693.34489.

Example 5: CIR 5 (I-5)

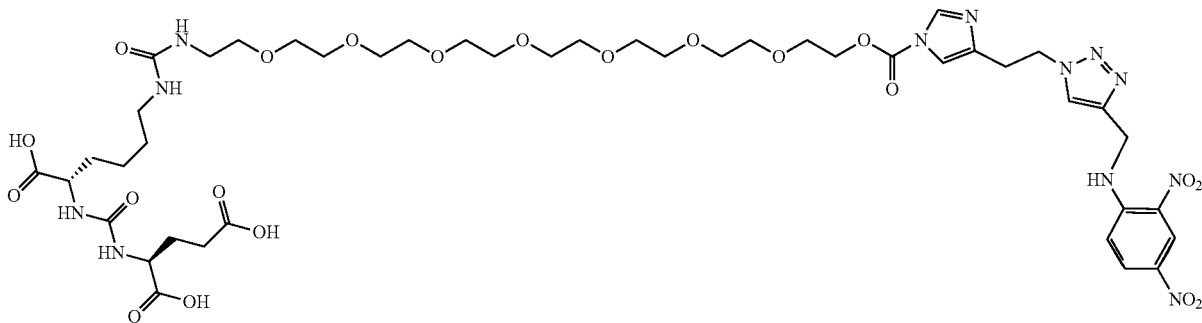

Step 1: Carbonate Intermediate 20

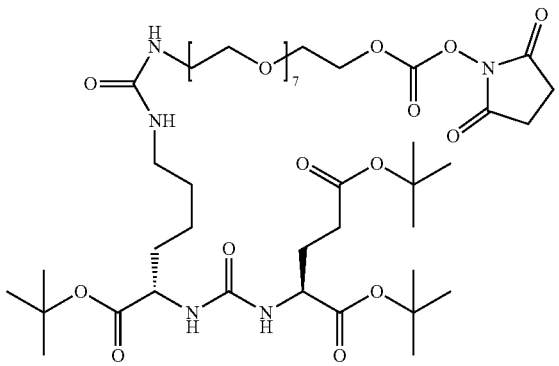

Compound 17 (232.9 mg, 0.264 mmol) and N,N'-Disuccinimidyl Carbonate (101 mg, 0.394 mmol) were dissolved in 2 mL of acetonitrile. Triethylamine (55 uL, 0.394 mmol) was then added, and the mix was stirred for 2.5 hours. This mix was injected on a 40 g flash $C_{18}$ column, pure fractions were collected and acetonitrile was removed under vacuum. The product was extracted into EtOAc, dried over anhydrous $Mg_2SO_4$ and concentrated under vacuum to yield semi-crude 20 (164.2 mg, 60.7% yield) as a clear oil. $^1$H NMR (700 MHz, CDCl$_3$) δ 5.63 (s, 1H), 5.51 (s, 1H), 5.45 (s, 1H), 5.35 (s, 1H), 4.45 (m, 2H), 4.31 (m, 1H), 4.22 (m, 1H), 3.78 (m, 2H), 3.64 (m, 24H), 3.55 (m, 2H), 3.36 (m, 2H), 3.16 (m, 2H), 2.84 (s, 4H), 2.31 (m, 2H), 1.93 (m, 2H), 1.68 (m, 2H), 1.42 (m, 29H), 1.35 (m, 2H). $^{13}$C NMR (176 MHz, CDCl$_3$) δ 172.7, 172.6, 172.5, 168.7, 159.2, 157.4, 151.7, 82.0, 81.4, 80.5, 68.4, 53.59, 53.56, 53.0, 40.4, 39.2, 31.8, 31.7, 29.8, 28.5, 28.2, 28.1, 25.6, 22.1. LCMS confirmed correct expected mass of product. MS-ESI [M+H]$^+$ m/z calc for [$C_{46}H_{82}N_5O_{20}$] 1024.55, found 1024.5426.

Step 2: Dinitrophenol-propargyl Intermediate 21

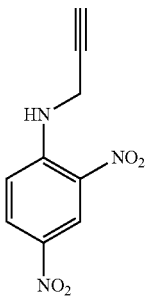

To a solution of 1-Chloro-2,4-Dinitrobenzene (318 mg, 1.57 mmol) and propargylamine (193.5 uL, 3.02 mmol) in ethanol (15 mL), DIPEA (526 uL, 3.02 mmol) was added. This solution was mixed overnight and dried under air stream. This crude product was purified on a 12 g buchi flashpure silica column with a gradient increasing from 75:25 to 0:100 Hex:DCM. Product fractions were collected and dried, then resuspended in DCM and crashed out in hexanes. The precipitate was collected via centrifugation, and dried to find pure 21 (152.7 mg, 44% yield) as a yellow solid. $^1$H NMR (700 MHz, (CD$_3$)$_2$SO) δ 9.05 (s, 1H), 8.88 (d, J=2.7 Hz, 1H), 8.38 (dd, J=2.7, 9.6 Hz, 1H), 7.25 (d, J=9.6 Hz, 1H), 4.35 (s, 2H), 3.31 (s, 1H). $^{13}$C NMR (176 MHz, (CD$_3$)$_2$SO) δ 147.2, 135.5, 130.4, 129.9, 123.3, 115.6, 79.3, 74.7, 32.3.

Step 3: Intermediate 22

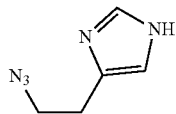

Sodium azide (554.6 mg, 8.532 mmol) was dissolved in 1.37 mL water followed by 1.37 mL toluene. This mix was cooled to 0° C. Triflic anhydride (896 uL, 5.326 mmol) was added to stirring mixture dropwise, and allowed to mix for 30 minutes (on ice). The mix was stirred further for 2 hours at 10° C. This was a biphasic solution with top translucent colourless, and bottom clear colourless layers. To this 6 mL of saturated sodium bicarbonate was added and stirred until bubbling stopped (about 10 minutes). This solution was washed 2× with 1.37 mL toluene. The organic layers were pooled (about 3.9 mL) and added to a separately prepared solution of histamine dihydrochloride (226.6 mg, 1.215 mmol), sodium bicarb (512.6 mg, 6.102 mmol), and copper sulfate pentahydrate (11 mg, 0.044 mmol) in 1.5 mL water. To this new mix, 9.9 mL MeOH was added for a homogenous mixture. This reaction was left to stir overnight. This mixture was dried under reduced pressure (keeping temperature strictly below 25° C.), and resuspended in 3 mL of 20:80 MeOH:DCM. This was pelleted, and supernatant purified on a 12 g buchi flashpure silica column. Product fractions were pooled and dried under vacuum to yield 22 (124.9 mg, 75% yield) as a yellow oil. $^1$H NMR (700 MHz, (CD$_3$)$_2$SO) δ 7.58 (s, 1H), 6.88 (s, 1H), 3.52 (t, J=6.9 Hz, 2H), 2.76 (t, J=6.9 Hz, 2H). $^{13}$C NMR (176 MHz, (CD$_3$)$_2$SO) δ 135.9, 134.1, 120.5, 50.2, 26.6.

Step 4: Intermediate 23

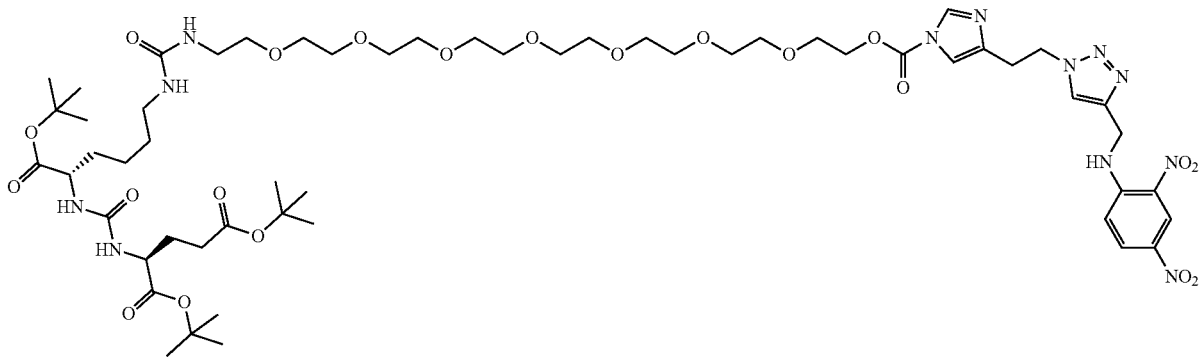 [SMILES: CC(C)(C)OC(=O)CC[C@H](NC(=O)N[C@@H](CCCCNC(=O)NCCOCCOCCOCCOCCOCCOCCOCCOC(=O)n1cnc(CCn2cc(CNc3ccc([N+](=O)[O-])cc3[N+](=O)[O-])nn2)c1)C(=O)OC(C)(C)C)C(=O)OC(C)(C)C]

Compound 20 (102.2 mg, 0.1 mmol) was resuspended in toluene and dried under vacuum. Separately intermediate 22 (16.4 mg, 0.12 mmol) was resuspended in toluene and dried under vacuum. Intermediate 22 was dissolved in anhydrous DMF (2 mL) and added to 20 under an argon atmosphere. Pyridine (24 uL, 0.298 mmol) was then added, and the solution was mixed for 3 hours. To this crude mix, intermediate 21 (53 mg, 0.24 mmol), L-sodium ascorbate (59.3 mg, 0.299 mmol), and copper sulfate pentahydrate (15 mg, 0.06 mmol) were added with additional anhydrous DMF (1 mL). This mixture was mixed for 1.5 hours then pelleted. The supernatant was purified via HPLC for pure 23 (73.4 mg, 58% yield). $^1$H NMR (700 MHz, (CD$_3$)$_2$SO) δ 9.26 (t, J=5.9 Hz, 1H), 8.86 (d, J=2.8 Hz, 1H), 8.25 (dd, J=2.8, 9.6 Hz, 1H), 8.15 (d, J=1.2 Hz, 1H), 8.00 (s, 1H), 7.28 (d, J=0.9 Hz, 1H), 7.25 (d, J=9.6 Hz, 1H), 6.28 (m, 2H), 5.91 (t, J=5.6 Hz, 1H), 5.79 (t, J=5.7 Hz, 1H), 4.76 (d, J=6.0 Hz, 2H), 4.61 (t, J=7.1 Hz, 2H), 4.45 (m, 2H), 4.03 (m, 1H), 3.95 (m, 1H), 3.73 (m, 2H), 3.56 (m, 2H), 3.48 (m, 22H), 3.32 (t, J=5.8 Hz, 2H), 3.12 (m, 2H), 3.05 (t, J=7.1 Hz, 2H), 2.94 (m, 2H), 2.21 (m, 2H), 1.76 (m, 2H), 1.53 (m, 2H), 1.38 (m, 27H), 1.33 (m, 2H), 1.24 (m, 2H). $^{13}$C NMR (176 MHz, (CD$_3$)$_2$SO) δ 172.2, 171.8, 171.4, 157.9, 157.0, 148.1, 147.8, 142.9, 139.4, 136.9, 135.1, 130.0, 129.8, 123.4, 123.1, 115.6, 114.1, 80.5, 80.2, 79.7, 70.1, 69.7, 69.5, 67.8, 67.1, 53.0, 52.1, 48.4, 38.4, 31.7, 30.8, 29.7, 28.3, 27.7, 27.6, 22.4. MS-ESI [M+H]$^+$ m/z calc for [C$_{56}$H$_{90}$N$_{12}$O$_{21}$] 1267.63, found 1267.4462.

Step 5: CIR 5

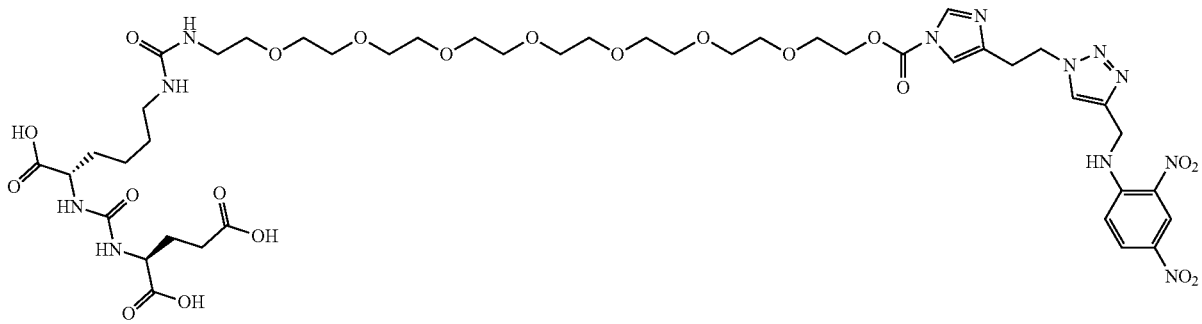 [SMILES: O=C(O)CC[C@H](NC(=O)N[C@@H](CCCCNC(=O)NCCOCCOCCOCCOCCOCCOCCOCCOC(=O)n1cnc(CCn2cc(CNc3ccc([N+](=O)[O-])cc3[N+](=O)[O-])nn2)c1)C(=O)O)C(=O)O]

Intermediate 23 was dried extensively under reduced pressure, and backfilled with an argon atmosphere. Dioxane·HCl (2 mL, 4M) was added, and stirred for 2 hours. Dioxane·HCl was removed under vacuum to yield CIR 5. Final product was immediately resuspended in DMSO and aliquoted for use in biological assays. Compound instability made HNMR preparation difficult. (100% yield) HRMS-ESI [M+H]$^+$ m/z calc for [C$_{44}$H$_{67}$N$_{12}$O$_{21}$] 1099.45, found 1099.57113.

Comparative Examples—Non-Reactive Covalent Immune Recruiters

Example 6: NCIR 6

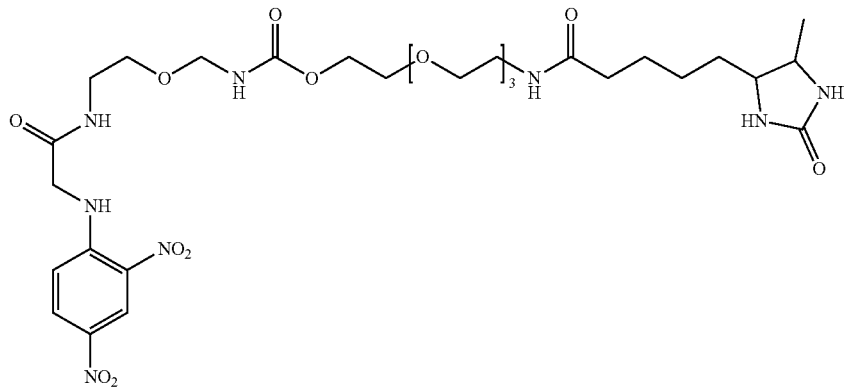

Step 1: Intermediate 24

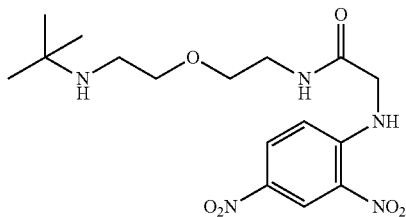 [SMILES: CC(C)(C)NCCOCCNC(=O)CNc1ccc([N+](=O)[O-])cc1[N+](=O)[O-]]

Intermediate 9 was prepared following a procedure similar to Example 1, step 2. Intermediate 9 (22 mg, 0.091 mmol) was dissolved in dimethylformamide 2 mL and added to t-butyl-amine PEG1 amine (22 mg, 0.108 mmol). Hydroxybenzotriazole Hydrate (18.3 mg, 0.135 mmol) followed by (3-Dimethylaminopropyl)-N'-ethylcarbodiimide hydrochloride (26 mg, 0.135 mmol) was then added to this solution. N,N-Diisopropylethylamine (47 uL, 0.271 mmol) was then added to the mixture. After stirring overnight, the mix was diluted with EtOAc and washed with sat. NaHCO$_3$ (aq) and brine. The organic layer was dried over anhydrous Mg$_2$SO$_4$ and concentrated under vacuum to yield 24 (28.1 mg, 80.5% yield) as a yellow powder. $^1$H NMR (700 MHz, DMSO) δ 9.11 (s, 1H), 8.88 (d, J=2.7 Hz, 1H), 8.30 (m, J=4.1 Hz, 2H), 6.94 (d, J=9.6 Hz, 1H), 6.76 (t, J=5.3 Hz, 1H), 4.17 (s, 2H), 3.42 (d, J=11.4 Hz, 2H), 3.36 (d, J=12.1 Hz, 2H), 3.27 (q, J=5.6 Hz, 2H), 3.06 (q, J=5.9 Hz, 2H), 1.37 (s, 9H). $^{13}$C NMR (176 MHz, DMSO) δ 167.70, 148.27, 135.69, 130.53, 123.81, 116.19, 78.12, 69.29, 46.10, 28.69 ppm.

Step 2: Intermediate 25

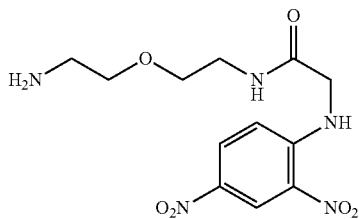 [SMILES: NCCOCCNC(=O)CNc1ccc([N+](=O)[O-])cc1[N+](=O)[O-]]

Intermediate 24 was dissolved in 3 mL DCM and 3 mL TFA and left to stir at room temperature overnight. The DCM/TFA was blown off under a nitrogen stream. The resulting yellow powder was resuspended in 10 mL DCM which was again blown off under nitrogen. The yellow powder was again resuspended in DCM and dried under vacuum to yield 25 as a TFA salt (30.8 mg, 128.3% yield) as a yellow oil. $^1$H NMR (700 MHz, DMSO) δ 9.10 (t, J=5.3 Hz, 1H), 8.89 (d, J=2.7 Hz, 1H), 8.32 (dd, J=4.1 Hz, 1H), 8.25 (t, J=5.6 Hz, 1H), 7.73 (s, 4H), 6.95 (d, J=9.6 Hz, 1H), 4.18 (d, J=5.4 Hz, 2H), 3.56 (t, J=5.2 Hz, 2H), 3.47 (t, J=5.9 Hz, 2H), 2.97 (m, J=5.1 Hz, 2H), 3.33 (m, 2H), 2.97 (m, J=5.1 Hz, 2H). $^{13}$C NMR (176 MHz, DMSO) δ 167.85, 148.24, 135.75, 130.57, 123.86, 116.20, 69.22, 66.77, 46.11 ppm.

Step 3: Intermediate 26

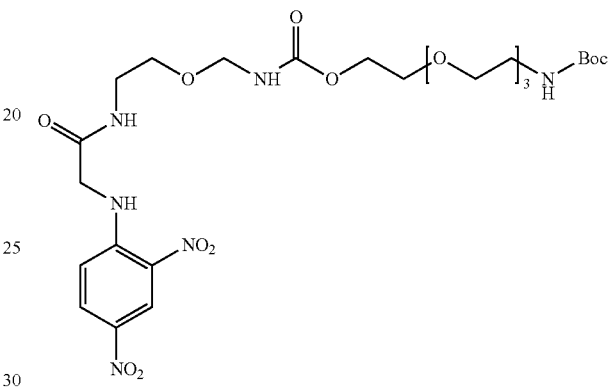

Intermediate 25 (78.1 mg, 0.239 mmol), intermediate 11 obtained from a procedure similar to Example 1, step 4 (103.66 mg, 0.239 mmol), and DIPEA (0.33 mL, 1.91 mmol) were mixed in 3 mL of dry DMF and stirred for 19 hours at room temperature. The reaction mixture was then added to ethyl acetate and this solution was extracted 3 times with saturated sodium bicarbonate. The organic layer was then concentrated to quantitatively yield crude compound 26 for direct use in the next step. $^1$H NMR (600 MHz, DMSO) δ 9.10 (t, J=5.3 Hz, 1H), 8.88 (d, J=2.7 Hz, 1H), 8.31 (dd, J=4.4 Hz, 1H), 8.28 (t, J=5.6 Hz, 1H), 7.19 (t, J=5.5 Hz, 1H), 6.95 (d, J=9.5 Hz, 1H), 6.74 (t, J=6.5 Hz, 1H), 4.45 (t, J=4.5 Hz, 2H), 4.17 (d, J=6.8 Hz, 2H), 4.04 (t, J=4.6 Hz, 2H), 3.69-3.04 (m, 20H), 1.37 (s, 9H).

Step 4: NCIR 6

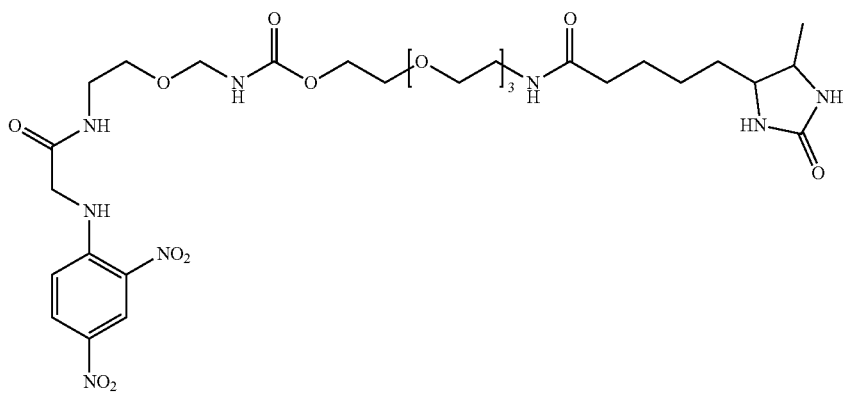

Intermediate 26 from the previous reaction was first deprotected with TFA for 3 hours and then dried. Deprotected intermediate 23 (38.6 mg, 0.0706 mmol), desthiobiotin (15.13 mg, 0.0706 mmol), EDC-HCl (16.4 mg, 0.106 mmol), HoBt-H₂O (14.3 mg, 0.106 mmol), and DIPEA (0.037 mL, 0.212 mmol) were stirred at room temperature for 24 hours in 3 mL of dry DMF. The reaction mixture was then concentrated down and dissolved in a small amount of DMSO. This was then loaded onto a celite solid loading cartridge followed by subsequent C18 flash column purification. The reaction mixture was run on a 4 g C18 column with a 15 minute gradient of 95:5 to 5:95 Water:ACN. The product fractions were then collected and lyophilized to give pure NCIR 6 in analytical quantities sufficient for in vitro assay analysis. ¹H NMR (600 MHz, DMSO) δ 9.10 (t, J=5.4 Hz, 1H), 8.88 (d, J=3.4 Hz, 1H), 8.30 (dd, J=4.1 Hz, 1H), 8.28 (t, J=5.6 Hz, 1H), 7.95 (s, 1H), 7.80 (t, J=5.5 Hz, 1H), 7.19 (t, J=6.1 Hz, 1H), 6.95 (d, J=9.6 Hz, 1H), 6.28 (s, 1H), 6.11 (s, 1H), 4.17 (d, J=5.4 Hz, 2H), 4.04 (t, J=4.6 Hz, 2H), 3.42 (m, 18H), 3.27 (q, J=5.6 Hz, 2H), 3.17 (q, J=5.9 Hz, 2H), 3.11 (q, J=5.8 Hz, 2H), 2.04 (t, J=7.4 Hz, 2H), 1.46 (m, J=7.4 Hz, 2H), 1.24 (m, 7H), 0.95 (d, J=6.4 Hz, 3H).

Example 7: NCIR 7

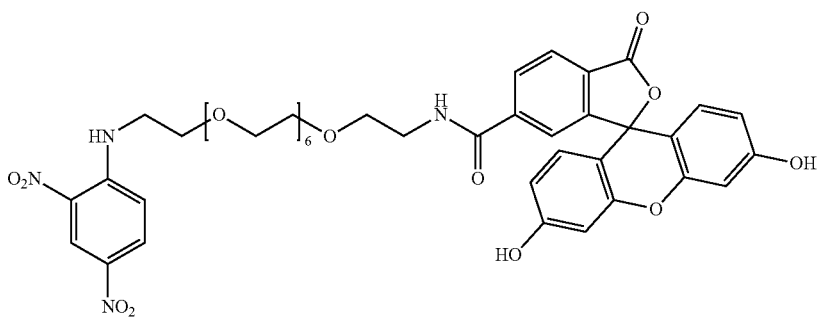

Step 1: Intermediate 27

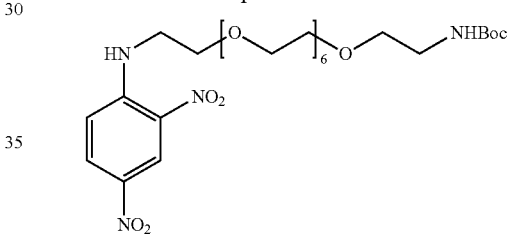

1-Chloro-2,4-Dinitrobenzene (50 mg, 0.247 mmol), NBoc-Peg7-NH₂ (127.23 mg, 0.271 mmol), and DIPEA (129 uL, 0.741 mmol) were combined in 1.5 mL of EtOH and stirred overnight. The reaction mixture was then concentrated down and dissolved in DCM. The material was then run on silica flash column with an isocratic DCM gradient. The crude product fractions were concentrated and then treated with 1 mL of TFA while stirring overnight. This crude reaction was then concentrated and co-evaporated with both toluene and DCM three times. From this 50 mg (38% crude yield) of 27 was used directly in the next step.

Step 2: NCIR 7

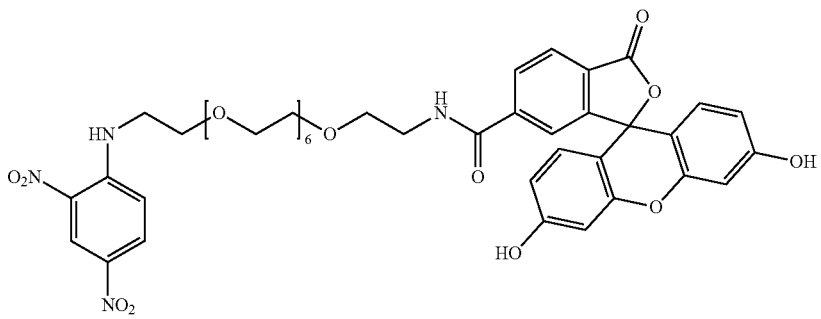

Intermediate 27 (50 mg, 0.0935 mmol) was dissolved in 1 mL of DMF. To this was added Fluorescein NHS as obtained in Example 2, step 1 (48.19 mg, 0.1122 mmol) and DIPEA (50 uL, 0.2805 mmol). This reaction mixture was allowed to stir overnight while being covered from light. The reaction mixture was then concentrated and redissolved in 1 mL of water (0.1% Formic acid) and ACN was added dropwise until all material was dissolved. This was then liquid loaded onto a reverse phase C18 column and run with a gradient of 95:5 to 5:95 Water:ACN. From this product fractions were pooled and concentrated while covered from light to give NCIR 7 (47 mg, 62% yield) of yellow product. $^1$H NMR (700 MHz, DMSO) δ 8.86 (d, J=2.7 Hz, 1H), 8.85 (t, J=5.6 Hz, 1H), 8.45-7.68 (s, 1H), 8.25 (dd, J=4.0 Hz, 1H), 8.22-7.36 (d, J=8.2 Hz, 1H), 8.15-8.06 (d, J=8.2 Hz, 1H), 7.27 (d, J=9.6 Hz, 1H), 6.67 (s, 2H), 6.59 (m, 2H), 6.54 (t, J=6.5 Hz, 2H), 3.57 (m, 24H).

Example 8: NCIR 8

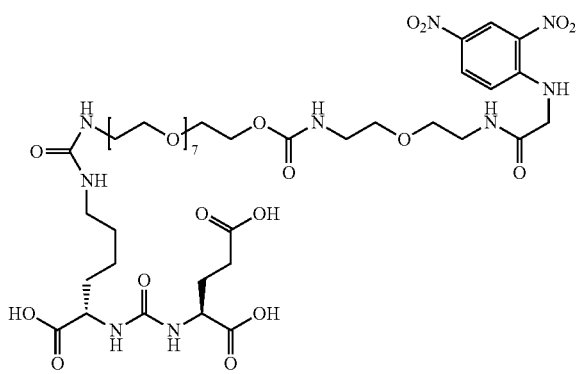

Step 1: Intermediate 28

Alcohol derivative 17 was obtained in accordance to Example 3, step 5. Alcohol derivative 17 (60 mg, 0.0679 mmol) and N,N'-Disuccinimidyl Carbonate (37.1 mg, 0.1148 mmol) were mixed and dissolved in 2 mL of toluene then concentrated to dryness under vacuum and backfilled with nitrogen. The residue was then resuspended in 3 mL anhydrous ACN followed by the addition of TEA (80 uL, 0.5736 mmol). After 3 hours of stirring, the solution was diluted with EtOAc (50 mL) and washed with sat. NaHCO$_3$ (aq). The organic layer was dried under vacuum then resuspended in 2 mL toluene, concentrated to dryness and the flask backfilled with nitrogen. In parallel, Compound 25 obtained from the procedure similar to Example 6, step 2 (53.76 mg, 0.1643 mmol) was toluene dried and backfilled with nitrogen. Compound 25 was then dissolved in 3 mL anhydrous DMF and pooled with the washed mix. Pyridine (20 uL, 0.2486 mmol) was then added to this solution. After overnight stirring the solution was diluted with EtOAc (10 mL) and washed with brine. The organic layer was dried over anhydrous Mg$_2$SO$_4$ and concentrated under vacuum. This crude product was further purified via Telendyne ISCO flash C18 column chromatography and concentrated to dryness to yield Compound 28 (26.5 mg, 31.5% yield) as a yellow oil. $^1$H NMR (600 MHz, DMSO) δ 9.10 (s, 1H), 8.87 (s, 1H), 8.29 (t, J=12.1 Hz, 2H), 7.19 (s, 1H), 6.94 (d, J=9.4 Hz, 1H), 6.26 (dd, J=8.7 Hz, 2H), 5.89 (s, 1H), 5.78 (s, 1H), 4.16 (d, J=5.4 Hz, 2H), 4.03 (s, 3H), 3.94 (d, J=6.5 Hz, 1H), 3.54 (s, 2H), 3.49 (s, 24H), 3.41 (s, 2H), 3.38 (s, 2H), 3.35 (s, 2H), 3.26 (s, 2H), 3.11 (d, J=5.9 Hz, 4H), 2.93 (d, J=5.7 Hz, 2H), 2.20 (d, J=26.6 Hz, 2H), 1.85 (t, J=6.9 Hz, 1H), 1.65 (t, J=7.2 Hz, 1H), 1.57 (t, J=7.2 Hz, 1H), 1.49 (d, J=6.8 Hz, 1H), 1.38 (d, J=6.3 Hz, 27H), 1.32 (d, J=7.0 Hz, 2H), 1.22 (s, 5H).

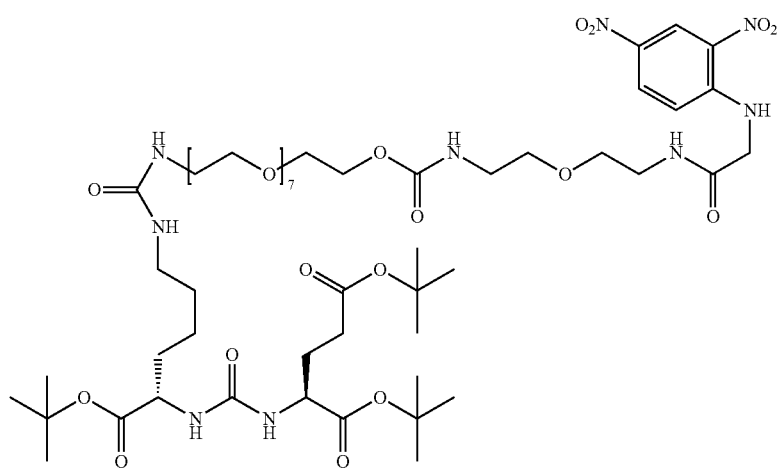

Step 2: NCIR 8

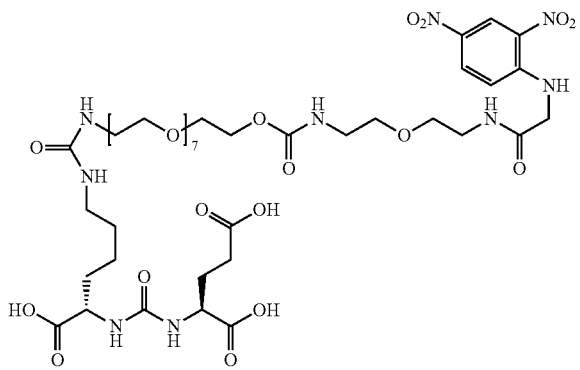

Intermediate 28 (26.5 mg, 0.0214 mmol) was dissolved in 3 mL Dioxane:HCl (4M) under argon and spun overnight. The solution was then diluted with DCM and dried under vacuum. This was then purified by HPLC to yield NCIR 8 (5 mg, 21.8% yield) as a yellow oil. $^1$H NMR (700 MHz, DMSO) δ 12.56 (s, 3H), 9.10 (s, 1H), 8.88 (d, J=2.7 Hz, 1H), 8.30 (dd, J=4.1 Hz, 1H), 8.28 (s, 1H), 7.20 (s, 1H), 6.94 (d, J=9.6 Hz, 1H), 6.30 (d, J=8.2 Hz, 2H), 5.91 (s, 1H), 5.80 (s, 1H), 4.17 (d, J=5.5 Hz, 2H), 4.05 (m, J=8.4 Hz, 4H), 3.55 (s, 2H), 3.50 (t, J=1.7 Hz, 24H), 3.42 (s, 2H), 3.38 (s, 2H), 3.35 (s, 2H), 3.27 (s, 2H), 3.12 (t, J=2.9 Hz, 4H), 2.94 (d, J=6.0 Hz, 2H), 2.23 (d, J=8.6 Hz, 2H), 1.87 (d, J=7.1 Hz, 1H), 1.72 (s, 1H), 1.62 (d, J=8.0 Hz, 1H), 1.50 (s, 1H), 1.33 (s, 2H), 1.26 (d, J=7.5 Hz, 2H). $^{13}$C NMR (176 MHz, DMSO) δ 175.02, 174.65, 174.26, 167.71, 163.56, 158.44, 157.73, 156.71, 148.29, 135.69, 130.54, 129.37, 128.68, 125.79, 123.83, 116.21, 70.60, 69.40, 69.30, 69.08, 63.64, 52.79, 52.22, 46.09, 32.33, 31.17, 30.24, 23.10 ppm. HRMS-ESI [M+H]$^+$ m/z calc for [C$_{42}$H$_{67}$N$_9$O$_{23}$]$^{2-}$ 1066.04, found 1066.488761.

Example 9: Docking Studies

Figure 2:
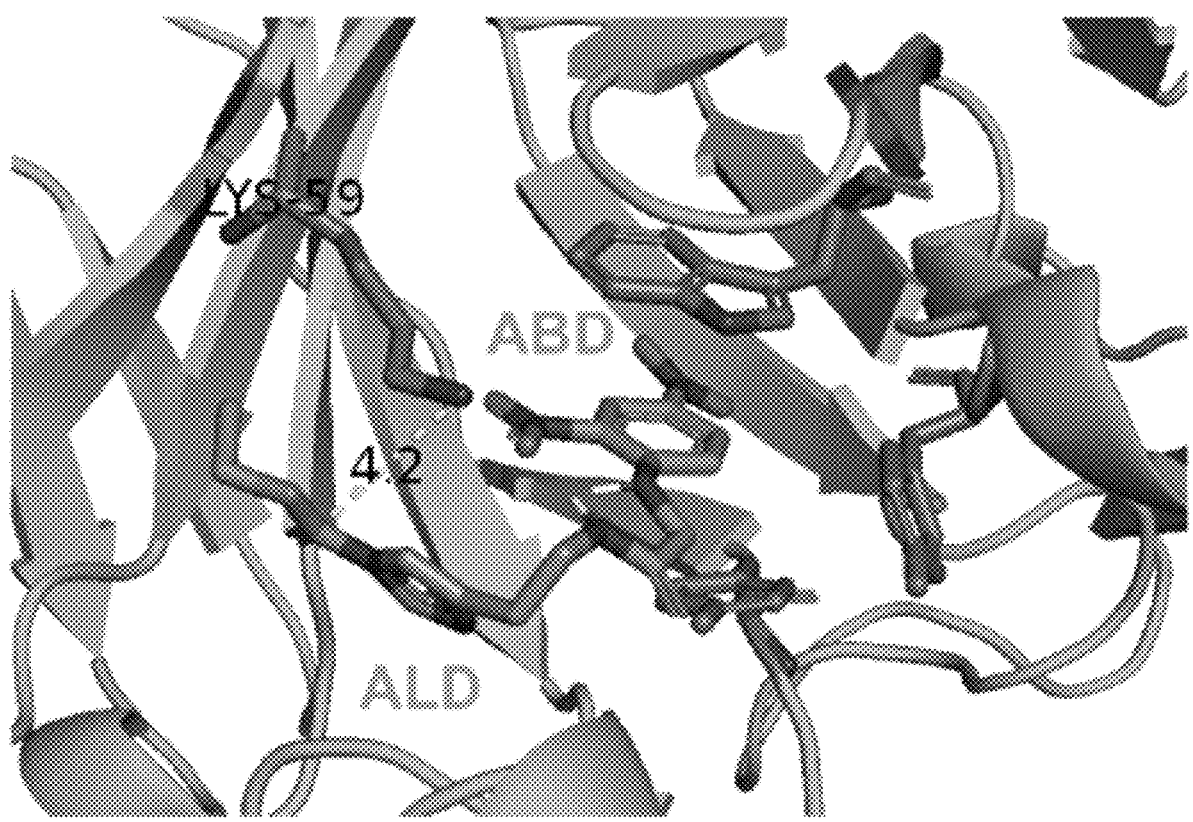
FIG. 2 is an illustrative 3D representation (PyMOL image) showing an antibody complexed to an exemplary compound of the application lacking the TBD, according to an embodiment of the application.

Docking studies using available anti-DNP crystal structures (PDB 1OAQ), guided CIR design with the goal of functionalizing a DNP containing ABD, with a lysine reactive acyl imidazole (Antibody Labeling Domain—ALD) for labelling the DNP binding site (FIG. 2). FIG. 2 is a pymol image of anti-DNP SPE7 (PDB 1OAQ) complexed to a model CIR fragment lacking the TBD, using autodock. CIR fragment backbone is in the center and key proximal lysine and aromatic residue sidechains are labelled. The ALD is in close proximity to lysine 59 (4.2 Å hashed line) poised for acylation.

Example 10: Aqueous CIR Stability Tests

Stability studies were conducted on a Sciex 4000 QTRAP, ESI-LCMS Triple Quadrupole Mass Spectrometer connected to an Agilent 1200 HPLC. All molecules were diluted 100× in PBS from a stable frozen DMSO stock solution reaching a final concentration of ≈10 μM in 1% DMSO/PBS and incubated for different amounts of time at room temperature, prior to LC-MS injection using a gradient of 95:5 to 5:95 (0.1% Formic Acid (aq)) water: ACN over 15 minutes. The integrations of the Absorbance values at 355-365 nm, were determined corresponding to the DNP moiety. The absorbance values corresponding to intact CIR were divided by the sum of intact and hydrolyzed CIR (the imidazole-DNP fragment) to determine fraction CIR intact changing with time. The fraction of intact CIR versus time was plotted on GraphPad Prism 8 using a "Dissociation—One Phase Decay" to extract the half life.

LC-MS analysis of the hydrolytic stability of CIRs 1, 3, and 4 in PBS was performed. The curve fit was done using a monoexponential decay which represents intact CIR plotted as a function of peak integration (corresponding to DNP absorbance) overtime. CIR1 was most stable with a $t_{1/2}$ of about 28 hours. CIR3 had a $t_{1/2}$ of about 12 hours and CIR4 had a $t_{1/2}$ of about 11 hours.

Example 11: Octet Binding and Kinetics Assays
(FIG. 4)

All the Anti-DNP Ab used in these experiments was Rabbit KLH Anti-DNP IgG Antibody with a stock concentration of 13.3 μM (Fischer Scientific Catalog #A-6430). The Isotype antibody used in experiments was 76.67 μM polyclonal human IgG (Jackson ImmunoResearch Catalog #009-000-003). Streptavidin coated biosensor probes from ForteBio were placed in 250 μl solutions of Kinetics Buffer (1×PBS, 0.01% BSA, 0.01% Kathon™, 0.002% Tween20™) spiked with 1% (v/v) DMSO for 20 minutes in an Octet Red96 for wetting at an RPM of 1000, temperature of 30° C., using an acquisition rate of 5 Hz. After baselining the signal, the probes were placed in a 200 nM solution of the CIR or NCIR of interest in Kinetics Buffer (1×) spiked with 1% (v/v) DMSO for 5 minutes to load the molecule onto the probe. This was followed by placing the streptavidin probes in a 5% (w/v) Milk quench solution in Kinetics Buffer (1×) spiked with 1% (v/v) DMSO, to block nonspecific binding for 140 seconds. To re-establish baseline, the streptavidin probes were placed back in the baseline (kinetics buffer) solution for 3 minutes. Next the streptavidin probes (loaded with CIR or NCIR of interest) were placed in a solution of kinetics buffer spiked with 1% (v/v) DMSO that also contained 500 nM rabbit polyclonal anti-DNP IgG KLH (Ab) in the presence or absence of 1 mM DNP-Glycine competitor, or 10 μM IgG isotype control antibody. Each replicate of each time point (0-15 hr) represents a single probe incubated in one of these assay condition solutions to monitor association. Next each probe was placed in kinetics buffer solution with or without 1 mM DNP-Glycine (dissociation buffer), for 50 minutes to monitor dissociation. To measure antibody labeling rate constants, the fraction reaction conversion was calculated at each time point by measuring the dissociation signal at t=0 (CIR$_{IT}$, NCIR$_{IT}$) and t=50 min (CIR$_{FT}$, NCIR$_{FT}$) for each CIR and for NCIR 6. Fraction conversion (CIR$_{FT}$–NCIR$_{FT}$)/(CIR$_{IT}$–NCIRF$_T$) was plotted versus the on probe association/reaction time, and fit using GraphPad Prism 8 employing a "One-Phase Association" equation to determine $k_{obs}$.

Assuming a pre-equilibrium kinetic model, the relationship between $k_{obs}$ and the pseudointramolecular labelling rate constant k, is described by the following equation:

$$k_{obs}=k\{[CIR:Ab]/[CIR]_t\}, \quad \text{Equation 1:}$$

therefore $k_{obs}$=k=1.486 h$^{-1}$ when CIR is saturated with anti-DNP which is the case on probes where $K_d$<<[Ab] but not in solution.

To estimate the true monomeric $K_d$ for CIR/NCIR binding to rabbit polyclonal anti-DNP IgG which is reported to bind DNP with higher affinity ($K_d$≈80 nM) compared to human polyclonal IgG,[1] $k_{on}$ and $k_{off}$ were calculated from octet association and dissociation experiments using NCIR 6 as described above. Dissociation experiments were conducted in the presence of 1 mM competitor DNP-Glycine to prevent antibody rebinding due to avidity. Using GraphPad Prism 8 equation "One-Phase dissociation", the $k_{off}$ was determined to be 0.001543 s$^{-1}$. Using GraphPad Prism 8 equation One-Phase "association" the $k_{obs}$ was determined to be 0.000970 s$^{-1}$ which was divided by [Ab] to yield a $k_{on}$=2.4× 10$^5$ M$^{-1}$ s$^{-1}$. The one phase association equation could be employed and a pseudo first order association process assumed, because antibody binding to NCIR 6 immobilized on the probe is essentially irreversible due to avidity and therefore association kinetics do not incorporate an antibody dissociation term.

The following equation could be used to estimate $K_d$ for NCIR binding to rabbit polyclonal anti-DNP IgG KLH, in close agreement with literature ($K_d$≈80 nM)·[2]

$$K_d = k_{off}/k_{on} = 63.6 \text{ nM} \quad \text{Equation 2:}$$

As a note, rabbit anti-DNP is a commonly used surrogate to model antibody recruitment of bonafide human polyclonal anti-DNP due to its high predicted structural homology and established ability to activate a subset of human immune effector cells.

To determine the kinetics of CIR 3 covalent labelling of anti-DNP IgG, a modified octet protocol was developed to accommodate the weaker binding affinity of glutamate urea on CIR 3 for biotinylated PSMA, which was loaded onto streptavidin coated octet probes in these experiments. First, streptavidin probes from ForteBio were placed in wells each containing 250 µl solutions composed of 100 nM biotinylated PSMA in kinetics Buffer (1×) spiked with 1% (v/v) DMSO for 20 minutes in an Octet Red96 instrument. The RPM was 1000, the temperature was held at 30° C., and the acquisition rate was 5 Hz. Following washing and baseline steps described above, the probes were then placed in a solution containing 200 nM CIR 3+100 nM anti-DNP IgG (Ab) that already had been allowed to react for varying amounts of time away from the octet instrument to form CIR 3-Ab, followed by quenching with 1 mM DNP-Glycine competitor to disrupt non covalent complex [CIR 3:Ab]. The association of CIR 3-Ab (already formed in solution) with PSMA coated probe was monitored, and the initial rates and final signal plateau measured as a function of the concentration of CIR 3-Ab formed with incubation time away from the octet instrument in solution. Following association experiments, probes could be re-generated for use to measure different assay conditions i.e. reaction time points, by placing each probe in a 10 mM Glycine-HCl pH 2.2 solution for 5 seconds followed by a PBS Solution for 5 seconds repeated three times to remove probe bound CIR 3-Ab via PSMA unfolding/refolding. The initial slope of the association curve for each reaction time point was divided by the initial slope of the association curve for the longest reaction time point*100, to calculate the % reaction with time. A plot of % reaction with time could be fit using a first order exponential equation using Graph Pad Prism to extract $k_{obs}$=. Based on the estimated $K_d$ for binding anti-DNP and fraction CIR 3 bound to 100 nM anti-DNP at equilibrium (≈0.5), the pseudo intramolecular complex labelling rate constant k=$k_{obs}$/0.5=0.51 h$^{-1}$ was calculated.

Example 12: SDS-PAGE and in Serum Labelling Assays

All Anti-DNP Ab used in these experiments was Rabbit KLH Anti-DNP IgG Antibody with a stock concentration of 13.3 µM (Fischer Scientific Catalog #A-6430). The Isotype antibody used in experiments was 76.67 µM polyclonal human IgG (Jackson ImmunoResearch Catalog #009-000-003). The ladder used in each gel was 10 µL of Bio-Rad Precision Plus Protein Unstained Standard (Catalog #161-0363). For each gel using 10% serum only 5 µL of sample was added per gel lane to avoid overloading the gel with protein. All gels were made with a 4% stacking gel and either a 10% or 12.5% resolving gel. All samples were mixed with BioRad 4× Laemmli sample buffer (Catalog #161-0747) and heated at 95° C. for 2 minutes prior to loading on the gel. All gels were run in an Invitrogen mini gel tank at 90 V for the length of the stacking gel and 120 V for the length of the resolving gel. Visualization of the gels for fluorescence was done on the GE Typhoon using the CY-2 laser. Once stained with EZ-Blue™ Gel Staining solution (Sigma) the protein contents were visualized using the 700 nM laser on the Odyssey™ CLX imager. For Densitometry analysis ImageJ software was used. Each lane was analyzed individually.

Figure 5A:
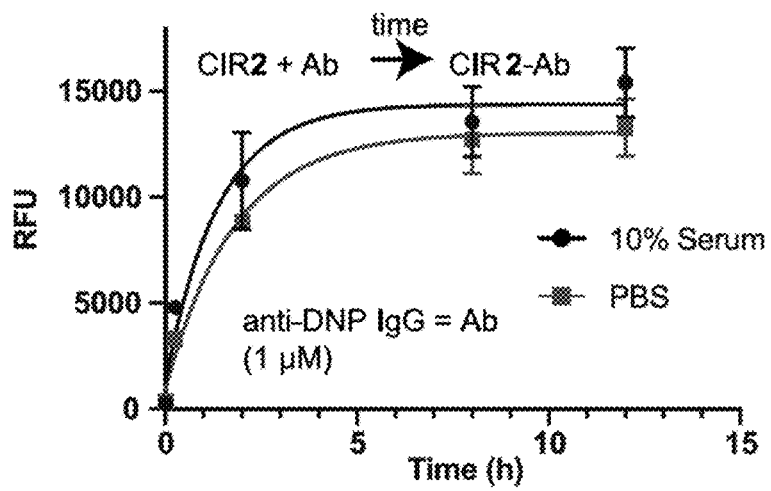
FIGS. 5A to 5D are fluorescence and densitometry imaging and analysis of an exemplary compound of the application.
Figure 5A:
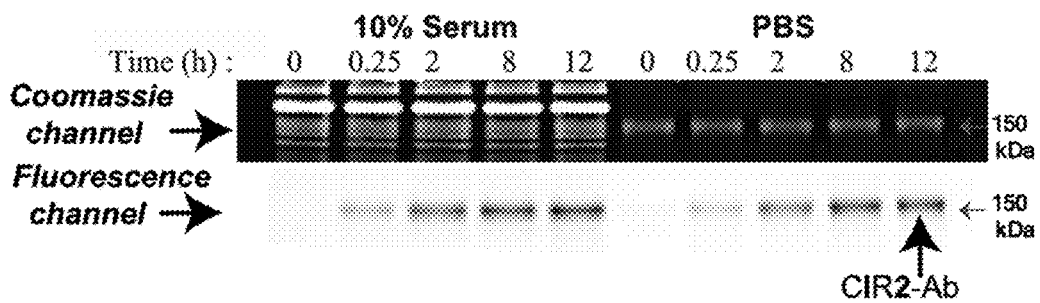

Example 13: Validation of CIR2-Ab Formation and CIR Labeling Selectivity in PBS Via SDS-PAGE (FIG. 5A)

All assay experimental and control conditions were incubated in PBS for 20 hours at room temperature covered from light. Antibody used for each condition was incubated at a concentration of 1 µM, with CIR/NCIR at a concentration of 2 µM assuming each CIR can bind to two Fab domains on an IgG antibody. After 20 hours 4× Laemmli sample buffer was added to each incubation. Each sample was then heated at 95° C. for 2 minutes and then loaded onto an SDS-PAGE gel with a 4% stacking gel and a 10% resolving gel.

Example 14: Determining the Kinetics of CIR 2-Ab Formation (FIG. 5A)

10 different conditions differing in reaction time were each run in duplicate on a single gel to enable for comparative densitometry analysis. Each incubation was done using an antibody concentration of 1.0 µM and a CIR 2 concentration of 2 µM (2:1 CIR to Ab). The incubation times varied at 0, 0.25, 2, 8, and 12 hours in both PBS, and 10% human serum that was diluted in PBS. Each reaction time point was quenched with excess DNP-Gly competitor prior to addition of 4× Laemmli sample buffer to each assay condition. Each sample was then heated at 95° C. for 2 minutes and then loaded onto an SDS-PAGE gel with a 4% stacking gel and a 10% resolving gel. The Fluorescence Intensity vs. time was plotted on GraphPad Prism 8, and a 'one-phase association curve' equation was used to extract the rate constant describing the pseudo intramolecular labelling of anti-DNP IgG with CIR 2=8.1×10$^{-4}$ s$^{-1}$.

Figure 5B:
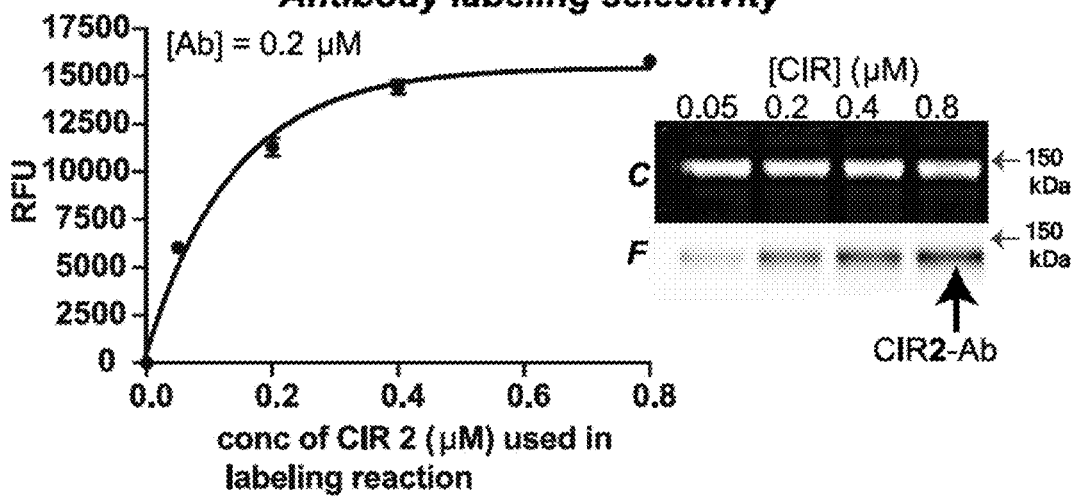

Example 15: Determination of CIRx-Aby Labeling Stoichiometry and Validation of CIR Ability to Stoichiometrically Label all Available Anti-DNP Antibody at Sub-Saturating (200 nM) and Approaching Saturating (1 µM) Concentrations (FIG. 5B)

In these experiments, four different conditions of varying CIR 2 concentrations were run in duplicate. The polyclonal anti-DNP IgG antibody concentration used for each condition was 200 nM while the CIR concentrations were 50 nM, 200 nM, 400 nM and 800 nM (0.25-4 equivalents). The solutions were allowed to incubate in PBS for 12 hours and then 4× Laemmli sample buffer was added to each incubation. Each sample was then heated at 95° C. for 2 minutes and then loaded on an SDS-PAGE gel with a 4% stacking gel and a 10% resolving gel. This experiment was repeated at higher antibody concentrations of 1 μM approaching saturation binding conditions ([Ab]>>$K_d$) The following CIR concentrations were incubated with antibody 1 μM, 2 μM, 3.5 μM, 5 μM and 10 μM (1-10 equivalents). The solutions were allowed to incubate in PBS for 20 hours and then 4× Laemmli sample buffer was added to each incubation. Each sample was then heated at 95° C. for 2 minutes and then loaded on an SDS-PAGE gel with a 4% stacking gel and a 10% resolving gel.

Figure 5C:
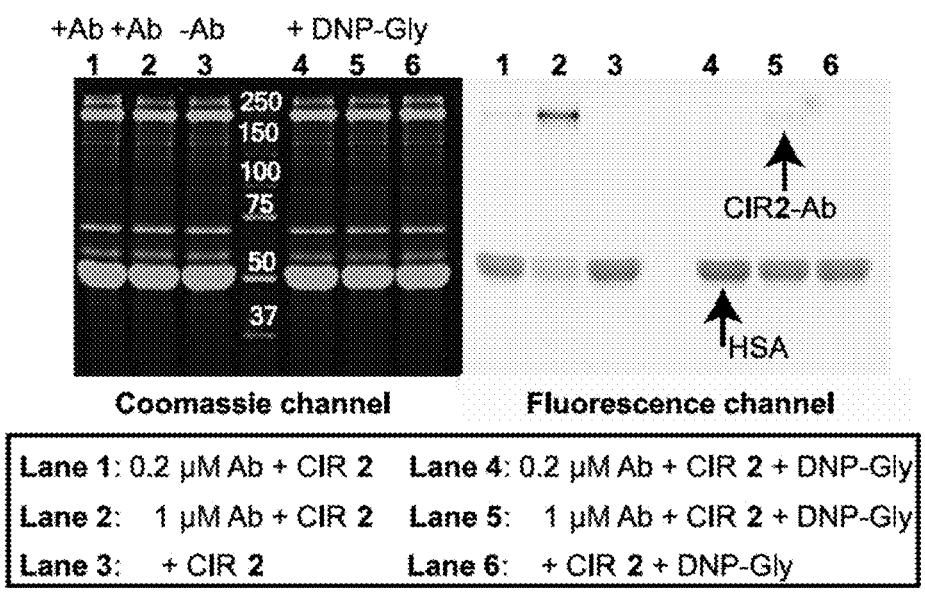

Example 16: Using CIR 2 as a Tool to Evaluate Endogenous Levels of Anti-DNP IgG (Ab) in 100% Pooled Human Serum (FIG. 5C)

In these assays, pooled human serum was incubated directly with 1 μM CIR 2 alone or spiked with sub-saturating (200 nM) or near saturating (1 μM) concentrations of anti-DNP IgG. For conditions involving spiked anti-DNP IgG, the effects of 1 mM DNP-Gly competitor on antibody covalent modification was also assessed. Each assay condition was carried out directly in 100% human serum for 24 hours, followed by dilution of each sample to yield 10% human serum which was mixed with 4× Laemmli sample buffer. Each sample was then heated at 95° C. for 2 minutes and then loaded onto an SDS-PAGE gel with a 4% stacking gel and a 10% resolving gel. The dilution of human serum was required due to the high total protein content in 100% human serum not compatible with SDS-PAGE.

Figure 6:
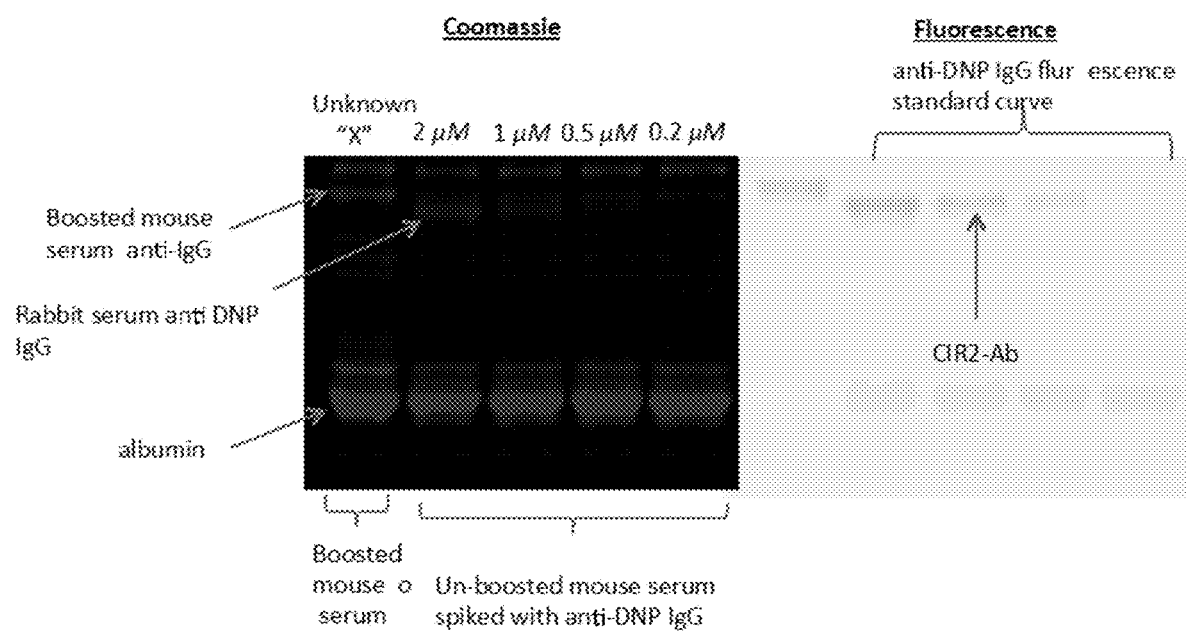
FIG. 6 shows the results from assays using exemplary compound CIR2 to quantify anti-DNP IgG serum concentrations in DNP immunized (boosted) mice via fluorescence SDS page.

Example 17: Using CIR 2 as a Tool to Quantify Boosted Levels of Mouse Anti-DNP IgG (Ab) in Serum from DNP Vaccinated (Boosted) Mice. (FIG. 6)

Known concentrations of commercially available rabbit polyclonal anti-DNP IgG (generated via DNP hapten rabbit immunization with adjuvant) were spiked into 5% unboosted balb-c mouse serum and incubated with excess (20 μM) CIR 2 for 5 h to ensure reaction completion. Each serum sample was analyzed by SDS-PAGE and used to generate a fluorescence standard curve to solve for the unknown anti-DNP IgG concentration present in the serum (5%) of boosted mice (generated in house via a DNP hapten immunization protocol with adjuvant). The unknown anti-DNP IgG antibody concentration "X" in 5% boosted mouse serum was estimated using the standard curve and calculated densitometry measurement for the only fluorescence band observed in boosted mouse serum incubated with CIR 2, which also migrated in the range expected for IgG antibody. In the corresponding Coomassie stain, this was the only major new protein band to emerge in boosted mouse serum compared to un-boosted however this band may represent all IgG induced via vaccination and not only anti-DNP IgG. The extracted concentration of ≈1.2 μM anti-DNP IgG in 5% boosted serum was used to back calculate what was present in 100% boosted mouse serum≈23.64 μM. Of note, CIR 2 labelling for both boosted and un-boosted mouse serum was done in 5% serum to reduce compound hydrolysis and off-target labeling which could obscure the accuracy of measurement as the analysis depends on CIR 2 labelling anti-DNP IgG in both boosted and un-boosted serum to the same extent with the same stoichiometry.

Example 18: Flow Cytometry ADCP and ADCC Assays (FIG. 7)

General: All flow cytometry experiments were run on a BD LSRII Flow Cytometer. The anti-DNP rabbit polyclonal KLH IgG was purchased from Fischer Scientific (A6430). The Isotype control used was Rabbit IgG control antibody purchased from Fischer Scientific (026102). PSMA loading/expression was confirmed with an anti-PSMA antibody Alexa 647 conjugate (Novus Biologicals, Catalog #FAB4234R). For PSMA competition controls, PMPA was purchased from Sigma (SML1612). Hek-293T (PSMA+/−) cell lines and biotinylated PSMA were generously given by Dr. Cyril Barinka (Institute of Biotechnology CAS, Czech Republic). U937 cells were generously given by Dr. John Valliant (McMaster University, Canada). IFN-γ was purchased from Fischer Scientific (PHC4031). Ultra low IgG FBS was purchased from Fischer Scientific (A3381901). RPMI-1640 was purchased as a powder from Fischer Scientific (31800089) and resuspended. DiD cell dye was purchased from Fischer Scientific (V22887). DiO cell dye was purchased from Fischer Scientific (V22886). TRYPLE Express was purchased from Fischer Scientific (12604013). Evaluation of CIR 3 Covalent Antibody Recruitment Kinetics in ADCP Flow Cytometry Assays Using PSMA Coated Beads 24 hours prior to inducing phagocytosis, 6 million U937 monocytes were seeded at 500,000 cells/mL and activated with IFN-γ (0.1 mg/mL). These cells were then counted and washed twice with serum free assay media (neat RPMI). Cells were then suspended to a concentration of 1 million cells/mL and stained with 1.9 μM Vybrant™ DiD Cell-Labelling Solution for 30 minutes (37° C., 5% $CO_2$). Cells were then washed 3× with warm assay media (AM, 10% Ultra Low IgG FBS in RPMI) and resuspended to a concentration of 1.5 million cells/mL for use.

5.6 million YG strep beads were washed 3× with PBS and resuspended in 150 μL of a saturating concentration of biotinylated-PSMA solution. This was allowed to incubate at 4° C. for 1 hour and then washed 3× with serum free AM. The beads were resuspended with AM to a concentration of 15 million beads/mL for use.

All stocks were made in AM. The initial anti-DNP antibody stock solution was made (320 μL of 200 nM). 75 μL of this was removed and 0.4 μL of PMPA solution was added (250 mM in DMSO). To the remaining antibody stock 1.2 μL of DMSO was added. The isotype antibody stock was then created (400 μL of 200 nM) and DMSO concentration made equivalent to other stocks. Separately, a stock solution of CIR 3 was made (320 μL of 400 nM). 70 μL of the CIR 3 stock and 70 μL of anti-DNP antibody stock were mixed for conditions: PMPA competition, Isotype control, experimental no Q, and 24Q. After 16, 20, 22, and 23 hours, 160 μL of 200 nM Anti-DNP antibody and 160 μL of 400 nM CIR 3 stock solutions were made, and 70 μL of each were mixed twice in separate vials (one to be later quenched and one not). After 24 hours 240 μL of 200 nM Anti-DNP antibody and 160 μL of 400 nM CIR 3 were created and the final conditions were mixed keeping DMSO concentrations at 0.43%. All conditions were then immediately quenched with 0.4 μL of DNP-glycine (100 mM stock in DMSO) or 0.4 μL of DMSO. This was allowed to incubate for 30 minutes. In this time 10 μL of prepared beads (150,000 prepared beads, see above) were added to a 96-well U-bottom plate. After the 30 minute quench, 60 μL of all conditions were then added to the beads in duplicate. Beads/conditions incubated for 20 minutes and pelleted (5 minute spin at 1400 rpm). Beads were then resuspended with 100 μL of U937 monocytes (150,000 cells, see above). This plate was softly pelleted for 2 minutes at 880 rpm and incubated for 1 hour (37° C., 5% $CO_2$). Conditions were then placed directly on ice and diluted with 100 μL of cold AM. All conditions were then run on flow cytometry to determine ADCP. Beads were detected in the PE-Cy7 channel, monocytes were detected in the APC Cy7 channel, PSMA loading was confirmed with the Alexa 647 channel. The following voltages were used: FSC-430, SSC-290, PE-Cy7-590, APC Cy7-380, A647-480. ADCP was determined by plotting monocyte stain against bead stain, and was quantified as % Target Phagocytosis=(Double Positive Events)/PSMA Bead Target Events+Double Positive Events×100. This was normalized to the unmodified anti-DNP antibody control.

Evaluation of CIR 3 Modulation of Immune Cell Activation Via Covalent Antibody Recruitment in ADCP Flow Cytometry Cell Assays 24 hours prior to inducing phagocytosis, 6 million U937 monocytes were seeded at 500,000 cells/mL and activated with IFN-γ (0.1 mg/mL). These cells were then counted and washed twice with serum free assay media (neat RPMI). Cells were then suspended to a concentration of 1 million cells/mL and stained with 1.9 μM Vybrant DiD Cell-Labelling Solution for 30 minutes (37° C., 5% $CO_2$). Cells were then washed 3× with warm assay media (AM, 14% Ultra Low IgG FBS in RPMI) and resuspended to a concentration of 3 million cells/mL for use.

Prior to phagocytosis, target cell lines (HEK PSMA+/−) were suspended with TrypLE™ Express and counted. These cells were then counted and washed twice with serum free assay media (neat RPMI). Cells were then suspended to a concentration of 1 million cells/mL and stained with 5.7 μM Vybrant DiO Cell-Labelling Solution for 30 minutes (37° C., 5% $CO_2$). Cells were then washed 3× with warm assay media (AM, 10% Ultra Low IgG FBS in RPMI) and resuspended to a concentration of 6 million cells/mL for use.

Antibody and CIR 3 stock solutions were created. An anti-DNP antibody solution with CIR 3 was created (160 μL, 2 μM antibody, 4 μM CIR 3) in PBS. An equivalent solution was created with isotype antibody. A stock with CIR 3 only and anti-DNP antibody only were also made with appropriate concentrations and with % DMSO adjusted. After incubation for 5 hours, a dilution series was created from the anti-DNP antibody and CIR 3 stock to allow for the dose response concentrations. In parallel, 25 μL of target cells (150,000 cells, see above) were added to a 96-well U-bottom plate. Here anti-PSMA A647 antibody and PMPA were added to cells in appropriate wells. The stock solutions of antibody and/or CIR 3 were then added to appropriate wells and allowed to incubate for 20 minutes with target cells. Next, 50 μL of monocytes (150,000 cells, see above) were added to the wells. This plate was softly pelleted for 2 minutes at 880 rpm and incubated for 1 hour (37° C., 5% $CO_2$). Conditions were then placed directly on ice. All conditions were then run on flow cytometry to determine ADCP. Target cells were detected in the Alexa 488 channel, monocytes were detected in the APC Cy7 channel, PSMA expression was confirmed with the Alexa 647 channel. The following voltages were used: FSC-430, SSC-290, A488-250 (Hek PSMA+) or 270 (Hek PSMA−), APC Cy7-420, A647-490. ADCP was determined by plotting monocyte stain against target stain, and was quantified as % Target Phagocytosis=(Double Positive Events)/PSMA Bead Target Events+Double Positive Events×100. This was normalized to the unmodified anti-DNP antibody control.

Discussion

Figure 3A:
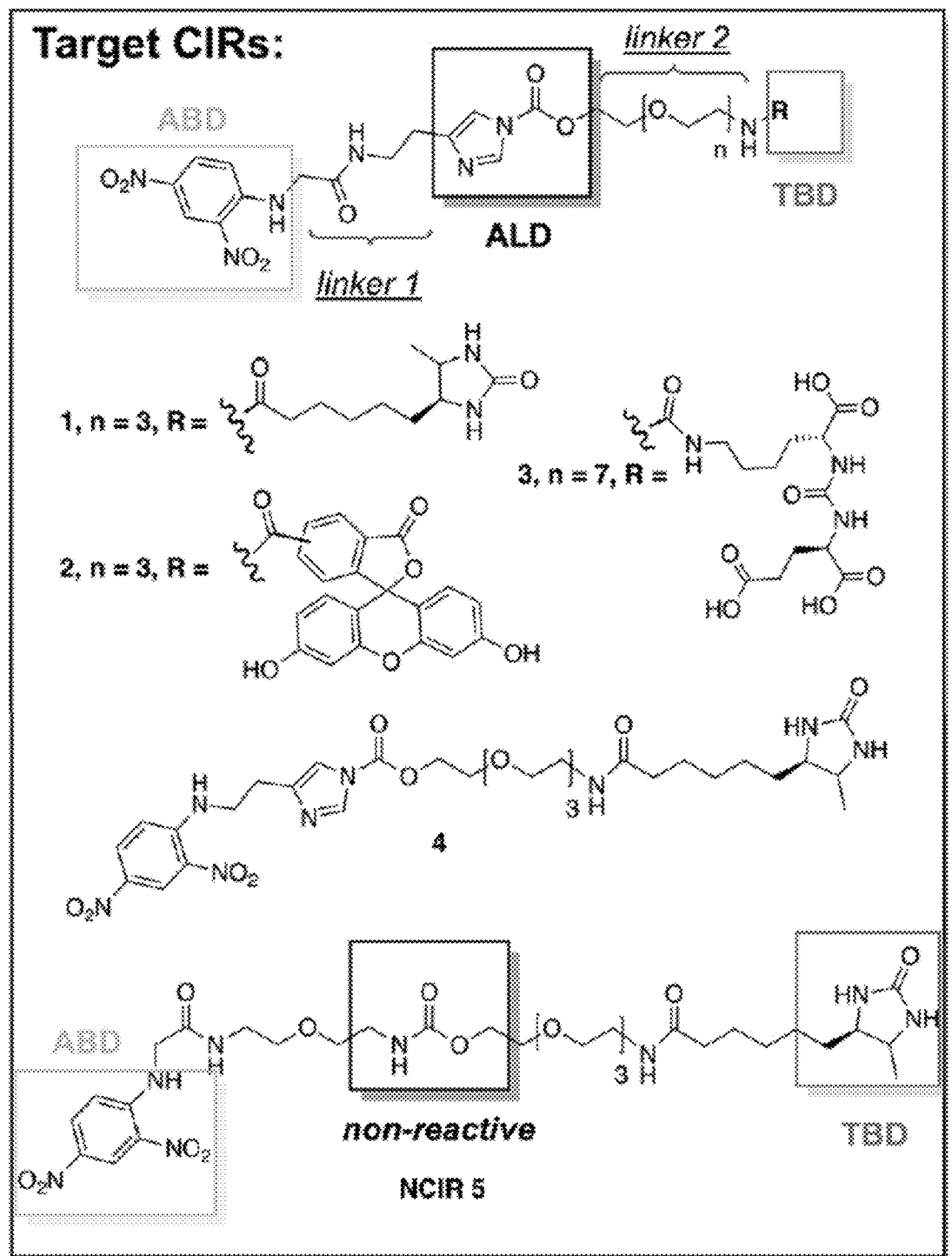
FIGS. 3A and 3B are schematic illustrations of embodiments of the application.
Figure 3B:
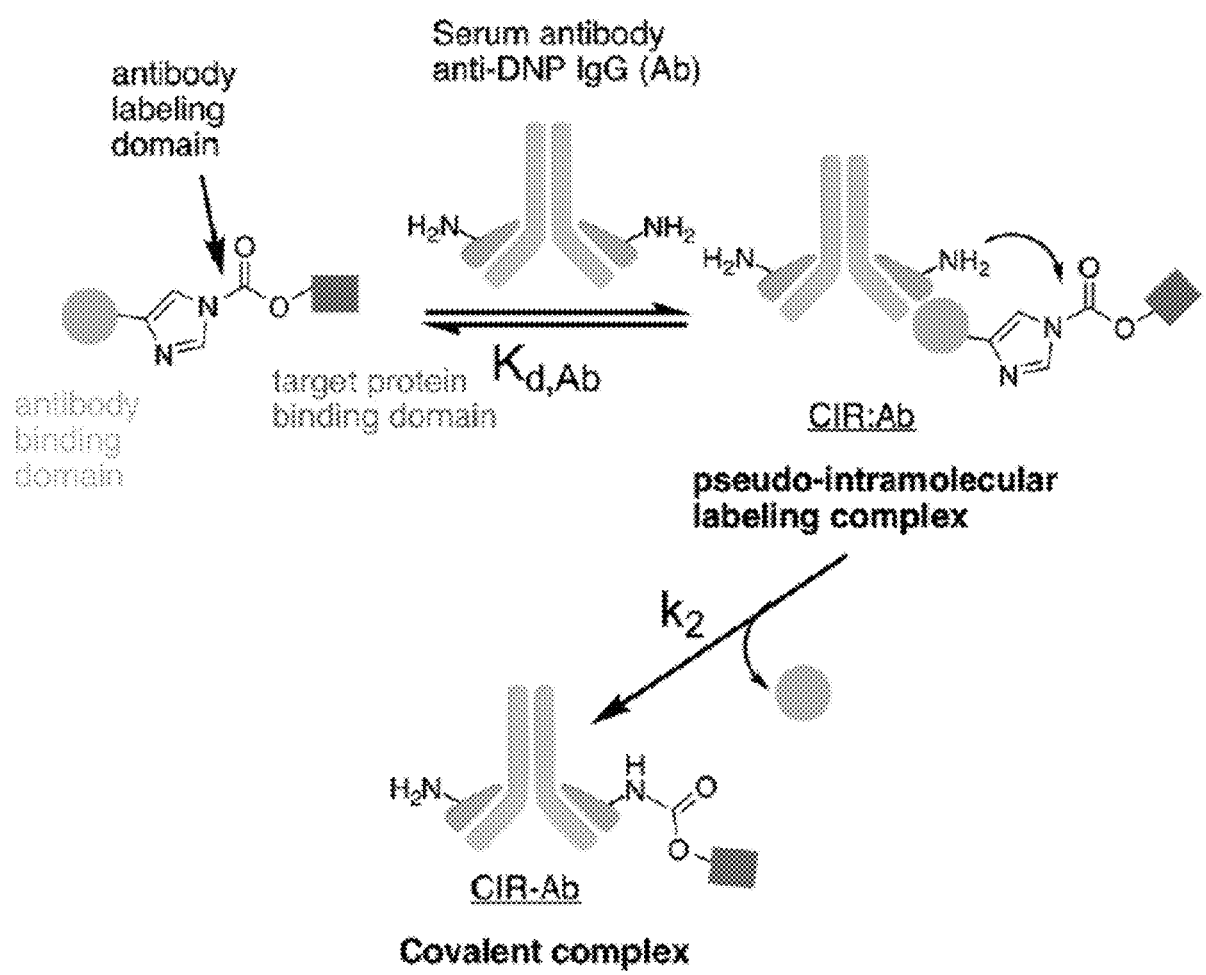

Exemplary CIRs contain a Target Binding Domain (TBD) attached to the ALD through a polyethyleneglycol (PEG) spacer (linker 2). Biotin and glutamate urea ligands were selected to equip labelled anti-DNP with the ability to bind immobilized streptavidin or cell surface Prostate Specific Membrane Antigen (PSMA), a prostate tumor surface protein. To study anti-DNP (Ab) labelling in human serum, CIRs were also synthesized to contain a fluorescein in place of a TBD. As covalent labelling controls, non-reactive analogs of CIRs (NCIR 6-8, Scheme 5, Examples 6-8) were synthesized. Finally, to probe the kinetic effective molarity of the CIR-Ab labeling reaction (FIG. 3B), CIR 4 with fewer rotatable bonds separating ABD from ALD (linker 1) was synthesized (FIG. 3A). CIR 4 is therefore hypothesized to label Ab more rapidly than CIR 1 following binding to form non-covalent complex. Specifically, FIG. 3A illustrates chemical structures of CIR tools synthesized and evaluated in this study. FIG. 3B illustrates CIR antibody labelling employing a pre-equilibrium kinetic mechanism. Labelling via acylimidazole chemistry results in ejection of the ABD from CIR.

Figure 4A:
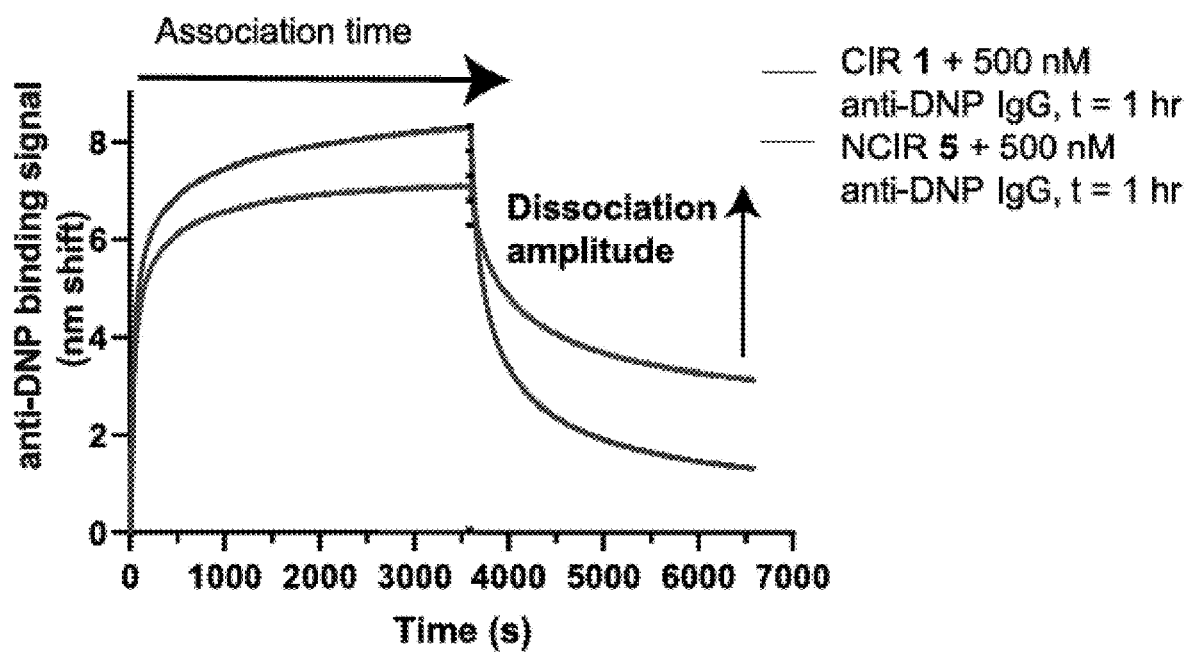
FIGS. 4A and 4B are graphs of covalent antibody recruiting assays.
Figure 4B:
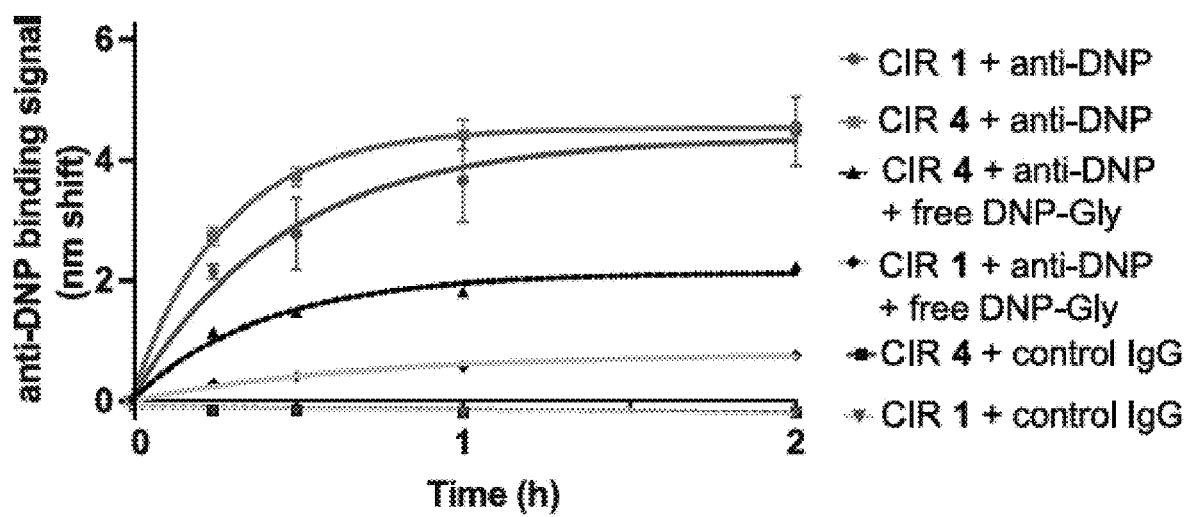

CIR 1 and CIR 4 time dependent antibody labelling selectivity was tested using a biolayer interferometry "octet" biosensor assay, with CIR bound via its desthiobiotin TBD to streptavidin probes. In these assays, the amount of time saturating concentrations of antibody were varied, and were incubated with now "CIR reactive" probes (association time) prior to placing probes in dissociation buffer (FIGS. 4 A-B). Specifically, FIG. 4 A-B illustrate biosensor immobilized CIR—anti-DNP IgG labelling timecourse assays. FIG. 4A illustrates results following a 1 hr antibody/probe association time (reaction time), a substantial fraction of bound antibody was covalently linked to CIR immobilized on strep-probes. This was demonstrated by the stability of bound antibody to dissociation in the presence of 1 mM DNP-glycine/PBS buffer, in contrast to antibody recruited non-covalently to NCIR immobilized on probes. Near saturating (500 nM) concentrations of polyclonal anti-DNP IgG were used in these assays. FIG. 4B illustrates the rate of anti-DNP IgG or control IgG covalently antibody recruitment by CIR, in the presence or absence of 1 mM DNP-glycine, was measured by decreases in antibody dissociation amplitude (Δnm shift) with reaction time. A plot of decreasing Δnm shift vs. reaction time was fit to a first order exponential rate equation using graph pad prism to extract $k_{obs}$ which could be converted to $k_2$ employing a pre-equillibrium kinetic model (see octet binding and kinetics assays below).

The measurement of the decrease in antibody dissociation amplitude (A nm shift) with reaction time (proportional to reaction conversion), enabled the estimation of pseudo-intramolecular antibody labelling rate constants describing CIR-Ab formation (CIR 1: $k_2 \approx 4.1 \times 10^{-4}$ $s^{-1}$, CIR 4: $k_2 \approx 8.2 \times 10^{-4}$ $s^{-1}$). Due to its weaker target protein binding affinity relative to CIR 1, modified "octet" solution labelling kinetic assays were performed with CIR 3 using PSMA coated probes, which yielded a comparable rate constant $k_2=1.4 \times 10^{-4}$ $s^{-1}$ as anticipated. Interestingly, despite their structural resemblance, these three derivatives exhibited modestly different hydrolytic stabilities with CIR 1 being most stable ($t_{1/2}$ hydrolysis=28 h, vs. CIR 3 $t_{1/2} \approx 12$ h and CIR 4 $t_{1/2}=11$ h). The extent of antibody labelling was substantially decreased in control experiments using free DNP-glycine (1 mM) competitor ligand, or control IgG (500 nM), consistent with CIR selectivity for labelling anti-DNP. DNP-glycine competes with and reduces the rate of a selective proximity induced CIR labelling reaction, but not potential off-target bi-molecular reactions with amino acids distal to the DNP binding site. Similarly control IgG lacks DNP binding ability and can only react non-specifically with CIR.

Figure 5D:
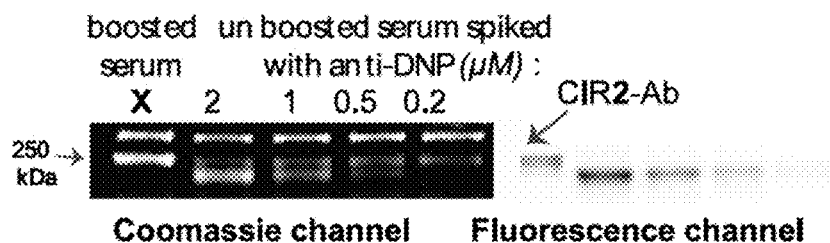
Figure 5D:
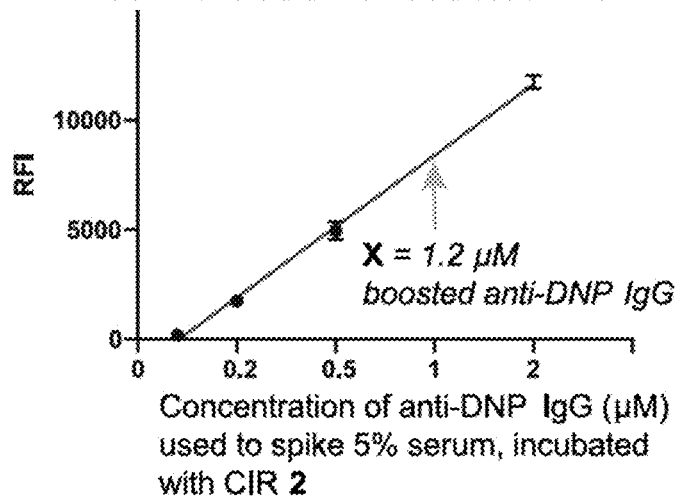

Due to the apparent increased hydrolytic susceptibility of CIR 4 coupled with its apparent lower degree of selective labelling in DNP-gly competition experiments, additional validation experiments were pursued using CIR 1. Next, evaluation of anti-DNP IgG labelling selectivity, and potential ability of CIR to stoichiometrically and quantitatively label anti-DNP were performed. This was carried out employing fluorescent derivative CIR 2 in solution assays monitored by non-reducing SDS-PAGE (FIGS. 5 A-D). Specifically, FIGS. 5 A-D show florescence and densitometry imaging and analysis in solution anti-DNP IgG (Ab)—CIR 2 labelling studies monitored by fluorescence non-reducing SDS-PAGE. FIG. 5A shows increases in fluorescence band intensity with time (RFU calculated according to adjacent Gel image), incubating polyclonal anti-DNP IgG (1 µM) with 2 eq. CIR 2 (CIR 2-Ab) in PBS alone or 10% human serum (spiked with anti-DNP IgG). Changes in fluorescence protein band intensity with time were measured via densitometry analysis. Curve fitting analysis was performed using a first order rate equation (see Example 11). In FIG. 5B, antibody labelling stoichiometry was assessed by plotting reaction endpoint fluorescence band intensities, for parallel reactions employing increasing molar equivalents of CIR 2. An arrow is included to illustrate the fluoresence plateau expected if all available "spiked" antibody (200 nM) is covalently linked to two CIR 2 molecules. FIG. 5C shows results for incubation of 2 eq of CIR 2 with pooled human serum alone or spiked with polyclonal anti-DNP IgG followed by densitometry analysis. anti-DNP IgG (=250 kDa band), HSA (=50 kDa band). Lanes 1 and 2 are spiked with 200 nM and 1 µM anti-DNP IgG respectively, Lane 3 was not spiked with anti-DNP and only contains potential endogenous anti-DNP. Lanes 4-6 are a repeat of Lanes 1-3 in the presence of competitor DNP-Gly. Observed off target HSA labelling is annotated. In FIG. 5D, serum isolated from Balbc mice boosted (X) or not boosted with DNP/adjuvent to produce anti-DNP IgG, was incubated with CIR 2 for 5 hours. To estimate the mouse serum concentration of boosted mouse anti-DNP IgG, a fluorescence protein band intensity versus concentration standard curve was generating using mouse serum isolated from unboosted mice that was spiked with different concentrations of commercially available polyclonal rabbit anti-DNP IgG, and incubating with a fixed 20 µM concentration of CIR 2 for 5 hours. This was followed by detection of fluorescent anti-DNP IgG protein bands via nondenaturing SDS-PAGE coupled with fluorescence imaging and densitometry analysis.

In PBS spiked with a fixed antibody concentration and CIR 2, the emergence of a fluorescent protein band corresponding to covalently labelled anti-DNP IgG was observed. Quantification of increasing fluorescence band intensity with time via densitometry analysis, enabled for the estimation of the solution pseudo-intramolecular (CIR:Ab) labelling rate constant $k_2$ ($8.1 \times 10^{-4}$ s$^{-1}$). This was in close agreement with that determined for on probe surface labelling by CIR 1 via "octet" above (FIG. 5A).

Consistent with a highly selective labelling reaction, (with minimal labelling of off-target proteins), the apparent labelling kinetics were minimally perturbed by repeating the assay in 10% human serum. Consistent with quantitative and selective labelling of polyclonal anti-DNP IgG (0.2 µM) at both Fab domains, maximum antibody fluorescent labelling was observed using approximately 2 equivalents (0.4 µM) of CIR 2 (FIG. 5B). This is consistent with the selective attachment of one fluorescent ligand to a single reactive amino acid at each DNP binding site of polyclonal anti-DNP IgG. In support of this claim were the results of labelled antibody digestion experiments using papain, which indicated that only the antibody Fab domain, which contains the DNP binding site, was covalently modified.

Selective labelling was also observed in 100% pooled human serum spiked with as low as 200 nM anti-DNP IgG (FIG. 5C, Lanes 1 and 4). HSA labelling was also observed as anticipated, since it is known to bind DNP and is present naturally at >500 µM concentrations in human serum. As a measure of antibody labelling selectivity, the addition of competitor DNP-Gly substantially inhibited antibody labelling consist with observations in biosensor assays. Interestingly antibody labelling was not observed in un-doped serum, suggesting lower<<200 nM anti-DNP, assuming a clonal distribution comparable to polyclonal rabbit IgG which is typically used as a model antibody for polyclonal human anti-DNP. To test a third strategy in the context of true endogenous serum anti-DNP IgG, fluorescent CIRs were employed to probe mouse serum isolated from animals subjected to DNP immunization protocols (FIG. 5D). A single new protein band was detected by Commassie staining in serum isolated from DNP boosted mice, with a MW corresponding to IgG, that was substantially fluorescently labelled by CIR 2. Quantitation of the resultant fluorescent band intensity using standard curve analysis provided a lower limit concentration estimation of ≈23 µM anti-DNP IgG. An important assumption employed to perform quantitative analysis of mouse serum polyclonal anti-DNP IgG is that CIR 2 reacts with comparable kinetics and stoichiometry to that determined against rabbit polyclonal anti-DNP IgG. Arguably, this proof of concept analysis represents the first attempt to quantify endogenous anti-DNP IgG concentrations directly in mouse and human serum. This is difficult to achieve through conventional ELISA protocols and affinity isolation techniques due to albumin binding. The ability to probe endogenous anti-DNP concentrations is serum can prove highly informative in assessing the potential in vivo anti-cancer efficacy achievable using future antibody engager immunotherapeutics.

FIG. 6 shows results using CIR 2 to quantify anti-DNP IgG serum concentrations in DNP immunized (boosted) mice via fluorescence SDS-PAGE. The fluorescence associated with the band representing IgG labelled with CIR 2 in serum from boosted mice (X), was quantified and compared to a standard curve generated from the fluorescence densitometry readings of known concentrations of anti-DNP IgG stoichiometrically labelled with CIR 2. In the lane (X) corresponding to IgG, only one band was preferentially labelled using CIR 2 with comparable kinetics to anti-DNP IgG (obtained from rabbits also boosted to produce anti-DNP IgG). This is consistent with the presence of a high relative concentration of anti-DNP IgG in the serum of immunized mice relative to un-boosted mice. The difference in band migration of hypothesized mouse polyclonal anti-DNP IgG relative to known rabbit polyclonal IgG is likely due to subtle differences in the extent of post translational glycosylation modifications and not in the structure of the DNP binding site. The structure of the DNP binding site across different monoclonal anti-DNP IgG antibodies generated in different species for use in crystallographic or NMR studies, appears to be relatively well conserved and rich in aromatic and lysine residues. Of important note, in contrast to humans, mice do not endogenously produce anti-DNP antibodies.

Figure 7A:
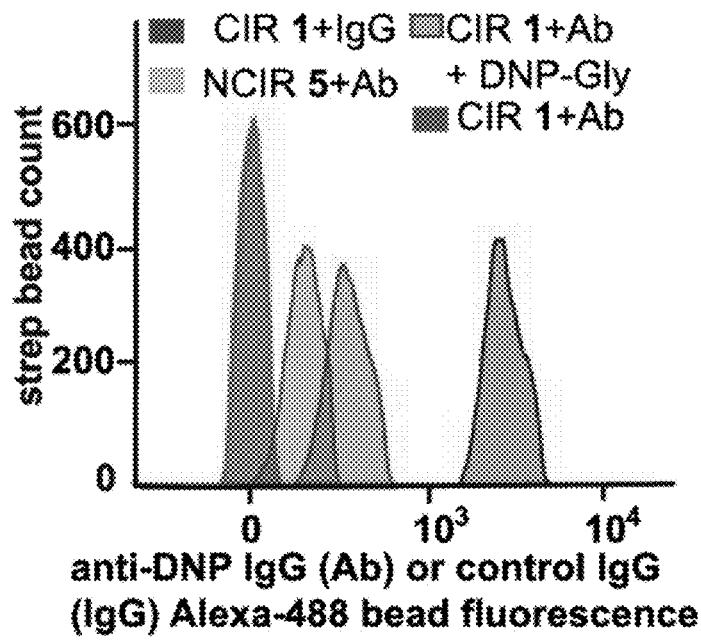
FIGS. 7A to 7F are graphs and illustration of the evaluation of immune recognition of targets via covalent antibody recruitment of exemplary compounds of the application.
Figure 7B:
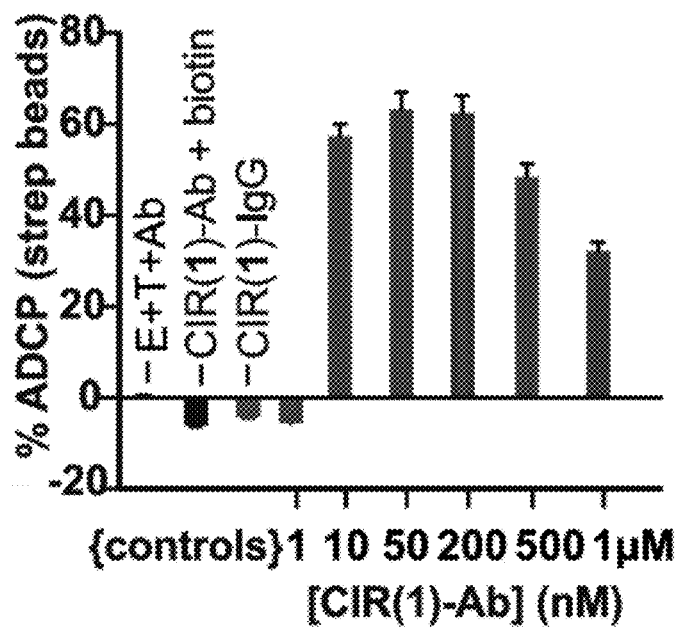
Figure 7C:
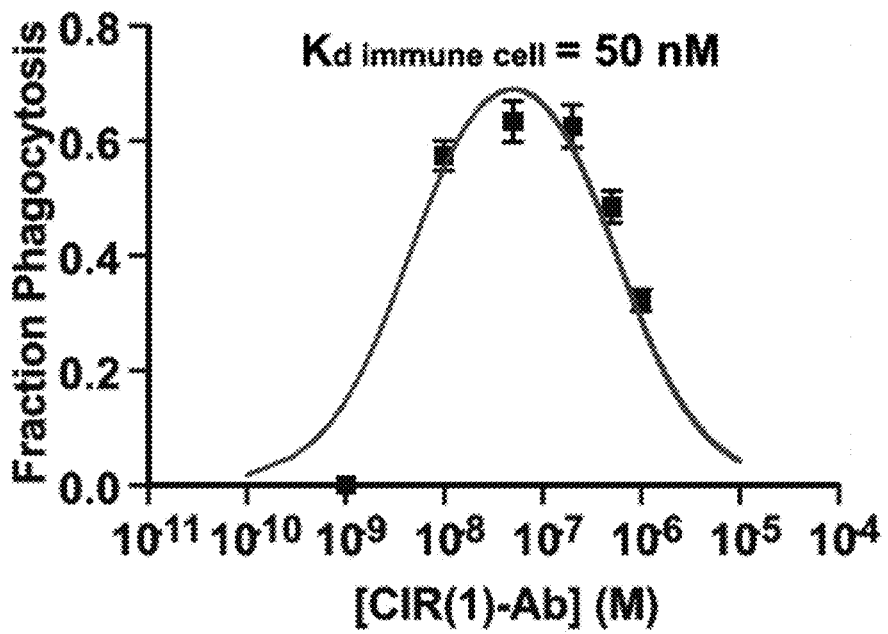
Figure 7D:
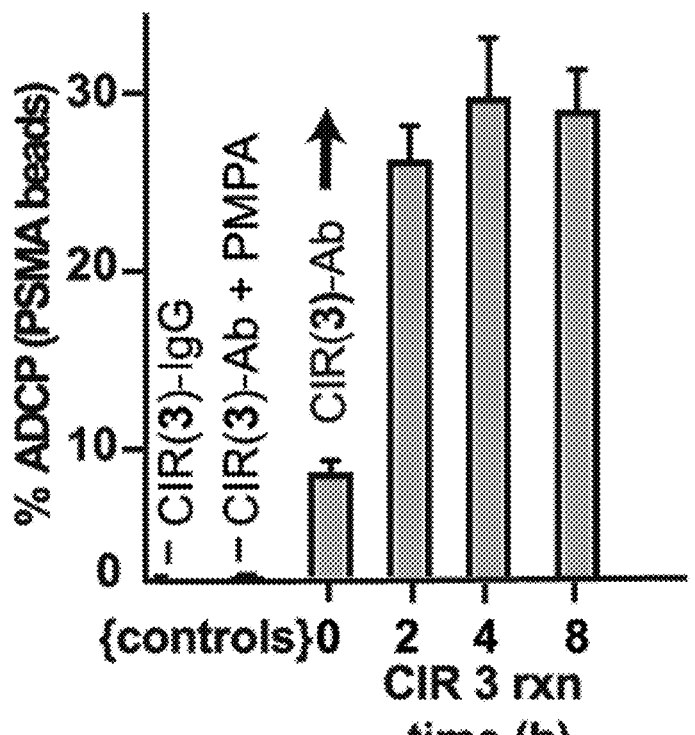
Figure 7D:
Figure 7E:
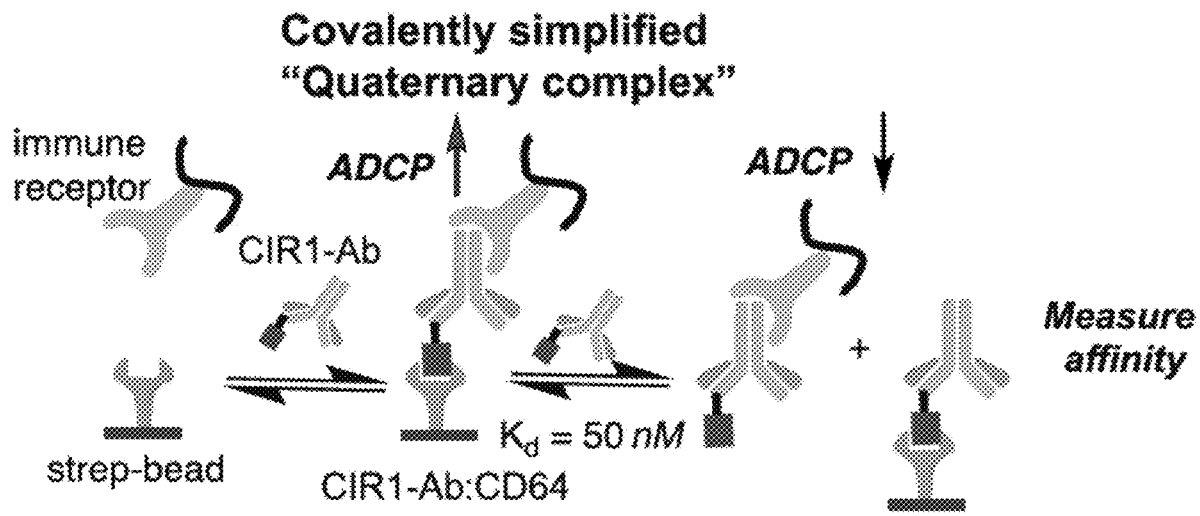
Figure 7F:
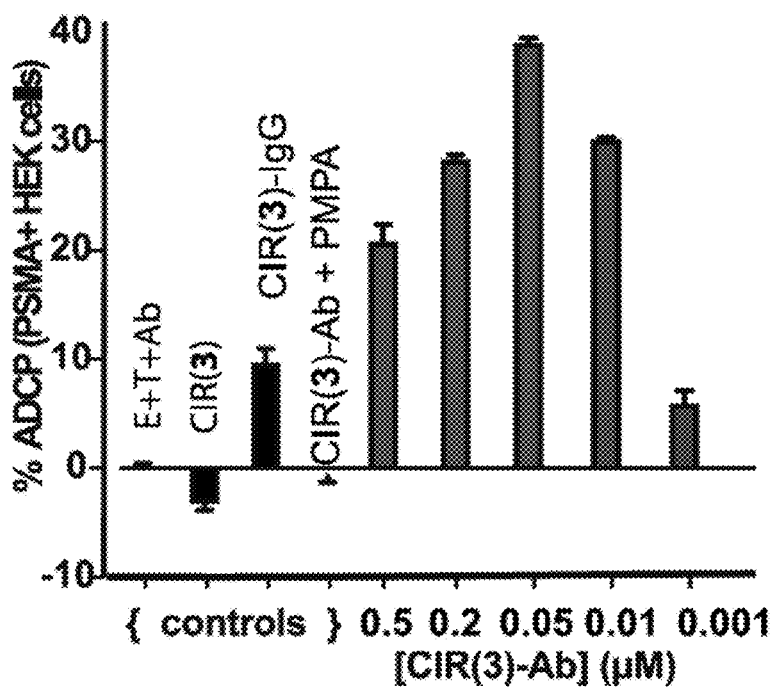

CIR ability to chemically affect immune recognition of targets through covalent simplification of quaternary complex formation was established by studying covalent antibody recruitment to both model beads and transfected HEK293T cells that express high levels of PSMA (>105 receptors/cell). This was carried out in flow cytometry binding and Antibody Dependent Cellular Phagocytosis (ADCP) assays using human monocytes, in addition to fluorescence Antibody Dependent Cellular Cytotoxicity (ADCC) assays employing human natural killer (NK) cells (FIGS. 7 A-F). Specifically, FIGS. 7 A-F illustrate evaluation of CIR mediated immune recognition of targets via covalent antibody recruitment. FIG. 7A shows flow cytometry covalent antibody recruiting assays employing 6 micron beads coated in streptavidin, CIR 1 (400 nM) and Alexa 488 labelled polyclonal anti-DNP IgG (200 nM). Increasing bead fluorescence is proportional to the magnitude of antibody recruitment. FIG. 7B shows flow cytometry ADCP assays using DIO stained beads coated in streptavidin, DID stained u937 human monocyte phagocytic cells, and anti-DNP lgG covalently linked to CIR 1. Phagocytosis is measured by double positive cell events. FIG. 7C shows ADCP data in B fit to a three component binding analytical model using GraphPad Prism. FIG. 7D shows flow cytometry ADCP assays using DIO stained beads coated in PSMA, DID stained u937 human monocyte phagocytic cells, 400 nM CIR 3 and 200 nM anti-DNP IgG. FIG. 7E illustrates a proposed mechanism of CIR mediated ADCP modelled using a 3 component binding analytical model. FIG. 7F shows flow cytometry dual colour (double positive) ADCP assays using DIO stained HEK PSMA+cells and DID stained u937 human monocyte phagocytic cells. E=monocytes, Ab=anti-DNP IgG, IgG=isotype control IgG, CIR3-Ab=CIR3 covalently linked to anti-DNP IgG.

First, evaluation if model streptavidin protein targeting CIR 1 can selectively covalently recruit sub saturating (200 nM) concentrations of Alexa 488 tagged anti-DNP IgG to streptavidin coated bead targets was conducted. To model the likely in vivo scenario of CIR encountering serum antibody prior to localization to targets, these studies involve a pre incubation of CIR 1 or non-reactive analog NCIR 6 with anti-DNP IgG on the time scale of hours, prior to exposure to targets. To unequivocally discern noncovalent binding from covalent reaction, excess free DNP-Gly competitor was added to these solutions prior to addition to beads to prevent antibody re-binding. Here, it was observed that substantially more Ab was recruited to beads by CIR 1 compared to NCIR 6 consistent with covalent antibody recruitment to beads (FIG. 7A). Consistent with a selective DNP binding induced labelling mechanism, covalent recruitment was substantially attenuated when the labelling reaction was performed in the presence of competitor DNP-Gly, or if non-binding control IgG was used in place of anti-DNP (Ab). To assess if covalent antibody recruitment could promote selective immune recognition of the target beads, dual color flow cytometry ADCP assays were performed. Here, the dependence of immune monocyte cell mediated phagocytosis of beads on the concentration of anti-DNP IgG covalently recruited by stoichiometric concentrations of CIR 1 (CIR 1-Ab) was measured. It was observed that CIR 1-Ab promoted selective ADCP of targets in a dose dependent manner, confirmed by competition experiments using free biotin, which inhibit ADCP by displacing CIR 1-Ab from beads. Additionally, CIR 1 was unable to covalently recruit control IgG which can activate ADCP but cannot bind and therefore cannot rapidly covalently react with CIR 1 (FIG. 7B). Since ADCP now occurs through "covalently simplified quaternary complexes" eliminating antibody binding complexity, available ternary binding models may be employed to study quaternary complex stability. Curve fitting analysis of the bell shaped dose response curve in FIG. 7B enabled for extraction of the apparent dissociation constant ($K_d \approx 50$ nM)) describing the target bound anti-DNP IgG:immune receptor binding interactions responsible for ADCP (FIGS. 7 C, E). Since binding of CIR 1-Ab to strep beads is essentially irreversible, both inflection points of the curve reflect the same immune cell receptor binding interaction. The calculated $K_d$ is in surprisingly close agreement with the known monomeric binding affinity between the pro-phagocytic receptor $CD_{64}$ on human monocyte effector cells and monomeric IgG.

Next, it was sought to confirm the covalent antibody recruiting approach could be applied to bonafide tumor protein targets. Towards this end, a time dependent variation of the ADCP assay performed in FIG. 7B was performed but here CIR 3 was employed, PSMA coated beads, and a fixed sub saturating 200 nM concentration of anti-DNP IgG (Ab). It was observed that CIR 3 could selectively affect ADCP of PSMA coated target beads via covalent recruitment of anti-DNP, in a time dependent manner (FIG. 7D). Notably, this was also carried out in a complex biological matrix 10% FBS+RPMI media and complete on the order of a few hours, the time scale of in vivo clearance and immune recognition events. Selectivity for target antibody was again demonstrated by the complete lack of recruitment of control IgG antibody, and selectivity for PSMA via competition experiments using 2-PMPA antagonist.

Finally, analogous to the studies in FIGS. 7 B, C and E, CIR 3 was applied as a tool to probe the stability of covalently simplified quaternary complexes comprising antibodies covalently recruited to live PSMA expressing cells, and human immune monocyte cells (FIG. 7F). It was again observed that PSMA and anti-DNP IgG selective ADCP of cells promoted via covalent antibody recruitment. Interestingly, control IgG which is capable of activating ADCP also appeared to non-specifically bind to HEK cells expressing PSMA. This accounts for the ADCP observed in experiments employing CIRs and control IgG. This is not reflective of a covalent linkage formed between CIR 3 and control IgG consistent with data presented in FIG. 7D. The application of a three component binding model to the ADCP CIR 3-Ab dose response curve again yielded the same apparent dissociation constant $K_d \approx 50$ nM describing the target cell bound anti-DNP IgG:immune receptor binding interactions responsible for ADCP. This is anticipated as immune cells interact with a polyvalent display of the same antibody in both scenarios. It was also validated that CIR 3-Ab can affect another mode of immune cell recognition of PSMA expressing cells via activation of human natural killer cell function in ADCC assays.

Given the known limited infiltration of immune cells into the congested tumor microenvironment, these functional studies suggest low affinity for immune cell receptors present at sub-saturating concentrations can limit AE anti-cancer efficacy, independent of a potentially high binding affinity for the target serum antibody relative to its endogenous concentration.

Taken together, the present results support the potential utility of CIRs as tools to probe immune recognition in vivo via their ability to form a selective covalent bond with serum antibodies directly in human serum. This can enable studies following the effects of AE clearance on anti-cancer efficacy, and the effects of maximizing AE:antibody binding affinity, on quaternary complex formation and immune recognition in vivo. Covalent antibody recruitment also represents a strategic alternative to extensive medicinal chemistry approaches needed, to achieve "irreversibly high" AE binding affinity for target antibody. Finally, since CIRs can potentially quantitatively recruit serum antibodies to a target in vivo, they can serve as useful tools to determine endogenous antibody concentrations in serum, and inform decisions on the potential need to boost antibody titers in AE immunotherapy.

Example 19: Comparison of CIR Versus ARM Target Immune Recognition

A series of covalent (CIR) and non-covalent (ARM) antibody recruiting molecules that use the same DNP hapten to bind anti-DNP antibodies were assessed using a panel of anti-DNP antibodies to represent concentrations and binding affinities found naturally in human serum.

Figure 8:
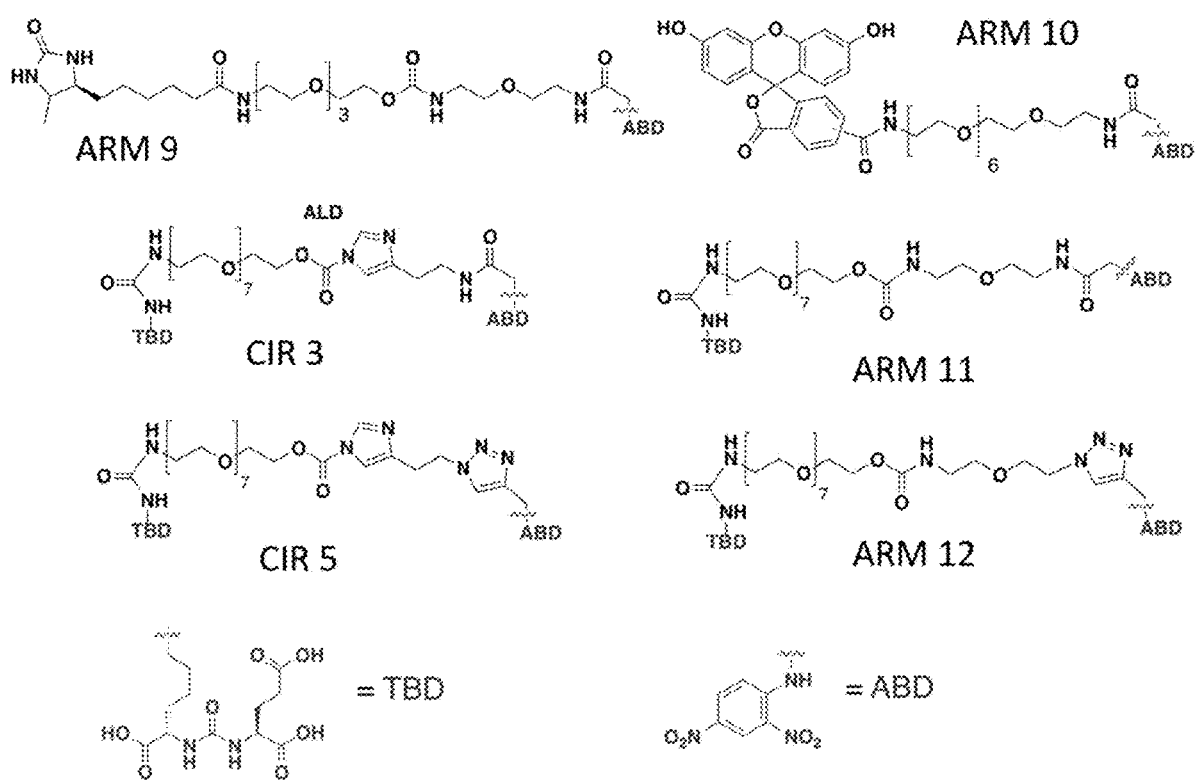
FIG. 8 shows chemical structures of exemplary compounds of the application and comparative non-covalent compounds.

FIG. 8 shows the chemical structures of CIR and non-covalent ARMs and were used for comparative evaluation in kinetics and immune functional assays. Model ARM compounds (ARM 9 and ARM 10) were synthesized to determine anti-DNP binding affinity and the kinetic stability ($k_{off}$) of ARM:Ab complexes. CIR 3 and CIR 5 and their non-covalent analogs, ARM 11 and ARM 12 respectively, share a common glutamate urea derived target binding domain (TBD), selective for PSMA.

CIR 5 was successfully afforded in moderate yield (=50-60%) via a late-stage copper click reaction, coupling a key glutamate urea-acylimidazole-azide intermediate to a propargyl modified DNP hapten. Gratifyingly, the acyl imidazole unit was tolerant to CuAAC conditions (Scheme 4).

ARM 12 was prepared as shown in Scheme 6. Therefore, azido-PEG1-amine was added to carbonate intermediate 20 to yield intermediate 29. Intermediate 21, L-sodium ascorbate, copper sulfate pentahydrate, and intermediate 29 were mixed then purified via HPLC to give intermediate 30. ARM 12 was obtained by adding dioxane·HCl to dried intermediate 30.

Scheme 6

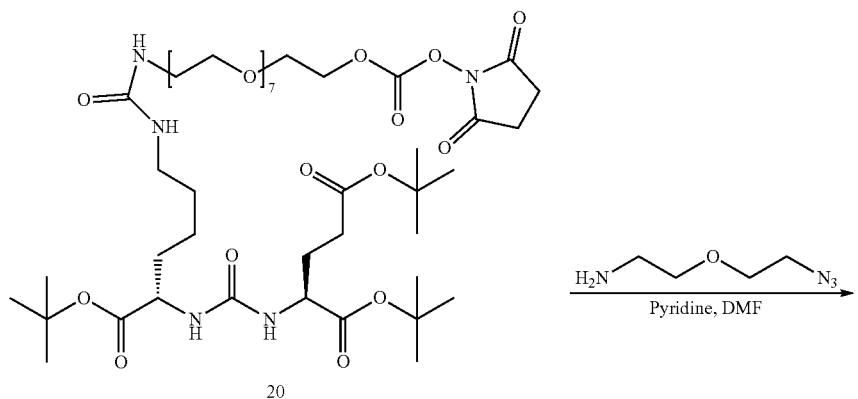

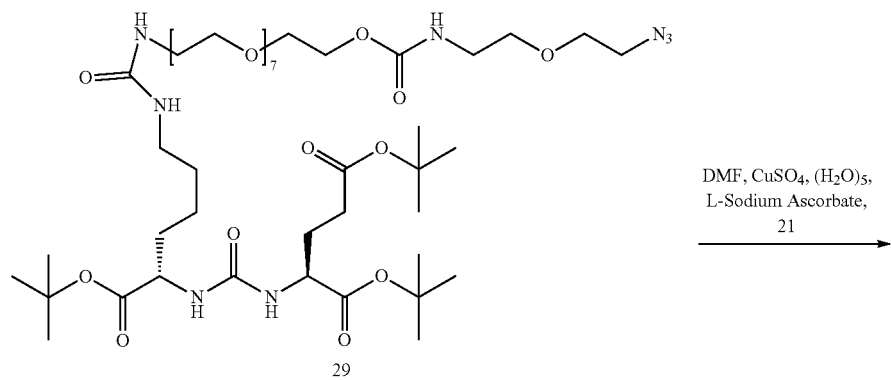

-continued

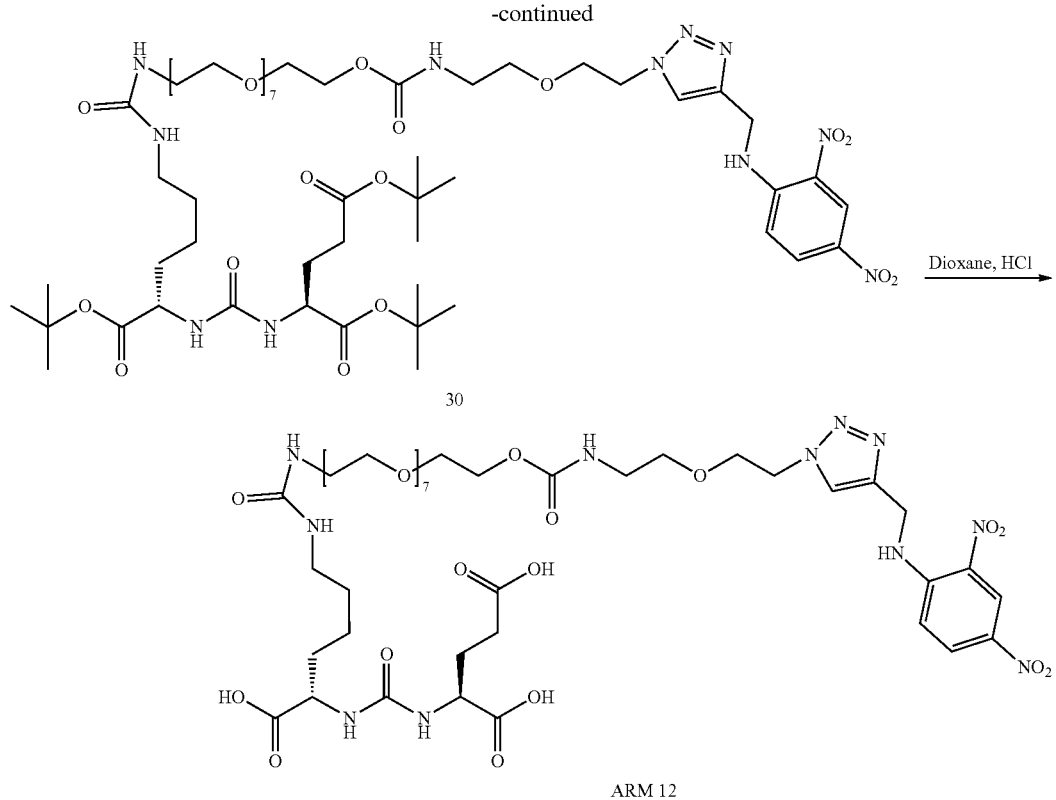

ARM 12

Evaluation of CIR Versus ARM Antibody Recruitment on Target Immune Recognition Using Humanized Anti-DNP SPE7 and Monoclonal Human Anti-DNP Anti-DNP SPE7 were re-engineered to contain a human Fc domain to mimic human IgG1 (mmAb) which can be recognized by human immune receptors. The heavy and light chains of anti-DNP SPE7 antibody was cloned into the EcoRI/NheI sites of pFUSEss-CHIg-hG1 (Invivogen) and the EcoRI/BsiWI sites of pFUSEss-CLIg-hK (Invivogen) respectively. The vectors were transfected at a 1:2 heavy chain to light chain ratio using the Expi293™ Expression System Kit (ThermoFisher A14635) according to manufacturer's protocols. Supernatant was collected when the Expi293 cells reached 60% viability. The antibodies were purified using 5 ml polypropylene columns (Qiagen 34964). with Protein G Agarose (ThermoFisher 15920010), followed by protein concentration and buffer exchange using Amicon Ultra-15 Centrifugal Filter Units. FIG. 9 shows the effects of covalent (CIR) vs. non-covalent (ARM) antibody recruitment on target immune recognition using anti-DNP mmAb.

To assess selective and efficiently covalently recruitment by CIR vs. ARM in a therapeutically relevant setting, a model monoclonal human anti-DNP antibody (mAb) of unknown structure was employed. FIG. 10 shows the effects of covalent (CIR) vs. non-covalent (ARM) antibody recruitment on target immune recognition using anti-DNP mAb.

Characterizing CIR Versus ARM Kinetics

The engineered mmAb was characterized in ARM:Ab complex stability studies using two complementary assays: i) biosensor-based biolayer interferometry (BLI) assays monitoring antibody dissociation from probes pre-coated with ARM 9 to enable direct evaluation of ARM:Ab complex kinetic stability (kof) and ii) fluorescence polarization (FP) assays involving titrating antibody against a fixed concentration of ARM 10 to enable calculation of solution ARM:Ab complex dissociation constants as a measure of thermodynamic stability.

The BLI assay was conducted using an Octet Red96 (ForteBio) with the temperature set at 25° C., the RPM set at 1000 and the acquisition rate set at 5 Hz. A volume of 250 µL of each solution was loaded into a black flat-bottom 96-well plate (Grenier). Streptavidin probes from Fortebio were placed in 1× Kinetics Buffer (Fortebio) for 20 minutes prior to experiment for wetting. The experiment began by placing the streptavidin probes in 1×Kinetics Buffer for three minutes to establish a baseline. ARM 9 was then loaded onto the probes by placing the probes in a 500 nM solution of ARM 9 for three minutes. Next, the probes were placed in a 5% w/v milk quench (Nestle Carnation Instant Skim Milk Powder) solution in order to block any free or non-specific binding sites on the probes surface. The probes were placed in 1×Kinetics Buffer for 30 seconds in order to re-establish a baseline. Association of the antibody to ARM 9 was measured by placing the probe immobilized with ARM 9 into a solution containing 1 µM of either mAb (ACRObiosystems cat. #DNP-M2) or mmAb for 5 minutes. Dissociation of antibody from ARM 9 was measured by placing the probe in 1× Kinetics Buffer for 10 minutes. The experiment was repeated twice, using 500 nM and 250 nM of antibody, for a total of three replicates. A control where no ARM 9 was loaded onto the probe was conducted by placing the Streptavidin probe into a solution of 1×Kinetics Buffer instead of a solution of 500 nM Compound 1 during the loading step. A free DNP competitor control was also conducted where 5 mM DNP-glycine was added to the antibody solution and acted as a competitor to prevent ARM 9 from binding to the antibody. The raw nm shift signal for the association and dissociation step obtained by the Octet Red96 was first baselined to the beginning of the association step (t=0 seconds) by subtracting the association signal at t=0 from the measured signal at each time point. The amplitude of the dissociation curve of three replicates for both mmAb and mAb was set to the same total amplitude of 2.7 nm shift. This value was chosen by constraining the amplitude of each curve to a global shared value and letting GraphPad Prism calculate the shared total amplitude. $k_{off}$ was extracted from the dissociation phase of the binding curve using the 'one-phase exponential decay' model in GraphPad Prism 8. $K_d$ was determined using the equation $K_d=k_{off}/k_{on}$. The $k_{off}$ values used represent duplicate averages determined from BLI assays described above. The $k_{on}$ value used was $2\times10^4$ $M^{-1}$ $s^{-1}$, previously estimated for the association of IgG antibodies with immobilized small molecule haptens.

All FP measurements were done on a TECAN SPARK plate reader, using Griener® Black 96 Well plates. The FP was set to 40 mP using the 50 nM ARM 10 only control, which was used to calculate the G-Factor. The gain was optimized at 80% max RFU with ARM 10 incubated with the highest Ab concentration (3163 nM for mmAb and 800 nM for mAb). A Z-position of 20000 was used. The buffer used was 1% DMSO 0.01% BSA (m/v), and 0.002% Tween 20, in PBS. Binding isotherms were generated by titrating increasing mmAb or mAb concentrations (50-3163 nM, and 50-800 nM respectively) against fixed 50 nM ARM 10. To generate binding isotherms FP signal was converted to "fraction bound" by first baselining FP signals to zero and dividing these values by the highest FP value determined for mmAb. Binding isotherms were analyzed via non-linear curve fitting in GraphPad Prism to calculate $K_d$.

The thermodynamic and kinetic stabilities of ARM:mmAb non-covalent complexes were determined to be on the order of $K_{d(Ab)}\sim10^{-8}$ M and $k_{off}\approx1.0\times10^{-3}$ $s^{-1}$ respectively (Table 1). Repeating these assays using commercial anti-DNP mAb confirmed its affinity for ARMs and the stability of resultant ARM 9:mAb and ARM 10:mAb complexes were both approximately 5-10 times lower than mmAb as anticipated.

TABLE 1

Anti-DNP binding constants for selected antibodies and CIR covalent and ARM non-covalent labeling parameters.

|  | mAb | mmAb |
| --- | --- | --- |
| $K_d$ [a] | 240 ± 40 nM | <80 nM |
| $K_d$ [b] | 410 ± 20 nM | 50 ± 1 nM |
| $K_{off}$ [b] | $8.2 \times 10^{-3} \pm 0$ $s^{-1}$ | $1.0 \times 10^{-3} \pm 0$ $s^{-1}$ |
| $K_{inact}$ [c] | $2.0 \times 10^{-4} \pm 0$ $s^{-1}$ | $4.0 \times 10^{-4} \pm 0$ $s^{-1}$ |
| $K_I$ [c] | 160 ± 70 nM | 30 ± 3 nM |
| $K_{inact}/K_I$ [c] | 1730 ± 1040 ($M^{-1}s^{-1}$) | 12000 ± 1000 ($M^{-1}s^{-1}$) |

[a] Determined using fluorescence ARM 10 in FP titration as assays.
[b] Determined using probe immobilized ARM 9 in BLI assays.
[c] Determined using CIR 3 in BLI kinetics assays.

Kinetic assays to characterize the second order rate constant ($k_{inact}/K_I$) describing the CIR+Ab labeling reaction involved incubating increasing concentrations of CIR 3 or CIR 5 with a fixed concentration (75 nM) of anti-DNP mmAb in solution, for different periods of time. PSMA binding to CIR-Ab complexes increases the total mass associated with the probe surface leading to signal increases (nm shift). CIR 3 (500 nM) and 75 nM of either mmAb or mAb (AcroBiosystems Catalog #DNP-M2) was reacted in 1× Kinetics Buffer (ForteBio) for four hours prior to the experiment. IgG Fc capture (ProG) probes from ForteBio were placed in 1× Kinetics Buffer for 20 minutes prior to the experiment for wetting. The experiment was conducted using an Octet Red96 (ForteBio), where the acquisition rate was set to 5 Hz and the temperature was held at 25° C. The plate shaker setting was 1000 RPM. A volume of 250 µL of each solution was loaded onto a black flat-bottom 96-well plate (Grenier). The experiment began by placing the ProG probes in 1×Kinetics Buffer for four minutes to establish a baseline. Next, the probes were placed into the CIR 3 and anti-DNP antibody reaction mixture to load the covalent complex (CIR-Ab) onto the probe. Next, the probes were placed in a solution of 5 mM DNP-glycine competitor in 1×Kinetics Buffer in order to disrupt any non-covalent or non-specific binding. The baseline was re-established by then placing the probes in 1× Kinetics Buffer for 0.5 minutes. To measure PSMA association, the probes were placed in a solution of 500 nM human PSMA protein in 1× Kinetics Buffer for 10 minutes. The probes were then placed in 1×Kinetics Buffer for 10 minutes to measure dissociation. The raw nm shift signal for the association and dissociation step obtained by the Octet Red96 was first baselined to the beginning of the association step (t=0 second) by subtracting the association signal at t=0 from the measured signal at each time point. The $K_d$ was determined by fitting both the association and dissociation curves using the 'association then dissociation' binding model in GraphPad Prism 8. The experiment was repeated once for a total of two replicates.

The specific labelling of an antibody by a CIR occurs via a two-step mechanism. In the first step, the CIR binds to the antibody via its ABD and forms a reversible complex. $K_I$ represents the binding affinity of this first step and describes the concentration of CIR required to achieve half of the maximal rate of covalent labeling. Under certain conditions, $K_I$ is equal to the dissociation constant $K_d$. In the second step, the covalent bond is formed as the ALD domain of the CIR reacts with the antibody. The first order rate constant $k_{inact}$ represents the maximal rate of this covalent bond formation. By taking both of these constants into account, the rate of covalent bond formation as a function of free CIR can be described by the saturation kinetics second order rate constant $k_{inact}/K_I$ or the ratio $k_{inact}$ to $K_I$. This second order rate constant was determined by monitoring covalent product (CIR-Ab) formation as a function of time via BLI using IgG Fc capture probes (note: a non-specific labeling reaction occurs independent of binding to the DNP binding site with any biological nucleophile and follows second order kinetics without saturation).

The CIR BLI assay was conducted using an Octet Red96 (ForteBio) where the acquisition rate was set to 5 Hz and the temperature was held at 25° C. The plate shaker setting was 1000 RPM. A volume of 250 µL of each solution was loaded into a black flat-bottom 96-well plate (Grenier). IgG Fc capture (ProG) probes from ForteBio were placed in 1×Kinetics Buffer (ForteBio) for 20 minutes prior to the experiment for wetting. The experiment begins by placing the ProG probes in 1×Kinetics Buffer for four minutes to establish a baseline. The probes were then placed in a solution of 75 nM mmAb or mAb (Acro Biosystems Catalog #DNP-M2) and varying concentrations (75 nM, 125 nM, 250 nM, 500 nM, 1000 nM, or 1500 nM) of CIR 3 in 1×Kinetics Buffer. For the initial zero-hour time point reading, the antibody was added immediately before the plate was placed into the Octet Red96 to minimize CIR 3 reaction with the antibody. Next, the probes were placed in a solution of 5 mM DNP-glycine competitor in 1×Kinetics Buffer in order to disrupt any non-covalent binding. The DNP-glycine will outcompete any non-covalently bound CIR 3 with anti-DNP antibody. The baseline was then re-established by placing the probes in 1×Kinetics Buffer for 0.5 minutes. To measure PSMA association, the probes were placed in a solution of 500 nM human PSMA protein in 1×Kinetics Buffer for 10 minutes. Human PSMA protein was generously provided by Dr. Cyril Barinka (Institute of Biotechnology CAS, Czech Republic). Data collection was repeated using the exact same sample plate prepared previously 0.5, one, two, and four hours after addition of the antibody to the reaction mixture. The entire assay was performed in duplicate for each antibody. The BLI assay described above was also used to determine the second-order rate constant describing the solution labelling kinetics of CIR 5 and mmAb, which also included an 8-hour reaction time point measurement.

Control experiments included a) a repetition where 1500 nM ARM 11 was incubated with the anti-DNP antibody instead of CIR 3, and b) a repetition where 75 nM of non-DNP binding human IgG (Jackson ImmunoResearch Catalog #009-000-003) was used instead of mmAb or mAb. The raw nm shift signal for the association and dissociation step obtained by the Octet Red96 was first baselined to the beginning of the association step (t=0 seconds) by subtracting the association signal at t=0 from the measured signal at each time point. The fractional conversion to product (CIR-Ab) was calculated in Excel by setting the maximum PSMA binding signal observed for the highest CIR 3 concentration (1500 nM) at 4 hours to equal 100% reaction. This was assumed to be reaction completion as there was very little increase in product signal, and therefore very little reaction occurring, when CIR 3 and the anti-DNP antibody was allowed to react for longer as illustrated by the t=8 h condition in FIG. 9A (note: longer time points lead to observed rates obscured by CIR 3 hydrolysis). The following equation was used to calculate fractional product conversion: (nm shift amplitude)/(nm shift amplitude at 1500 nM CIR, t=4 h). The fractional conversion to product values were multiplied by the concentration of antibody (75 nM) to determine the CIR-Ab covalent product concentration. A curve of covalent product (CIR-Ab) concentration over time was fit using Dynafit to determine reaction kinetics constants through non-linear least-squares regression analysis. The average rate constants from both trials were calculated and reported in Table 1.

Figure 9A:
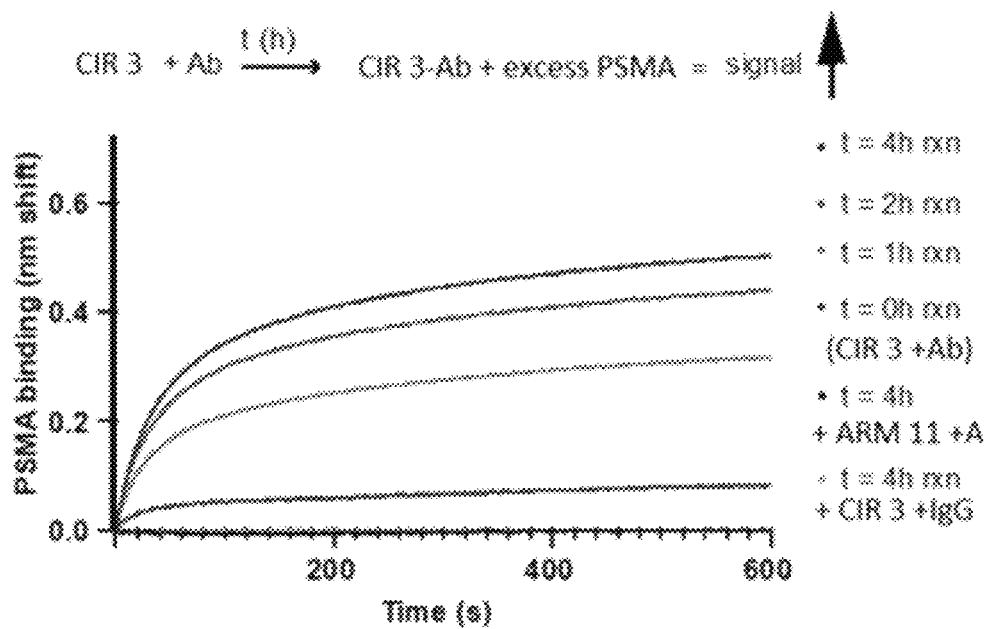
FIGS. 9A to 9F are graphs of antibody recruiting assays and evaluation of immune recognition of targets of exemplary compounds of the application and comparative non-covalent compounds using humanized anti-DNP SPE7.
Figure 9B:
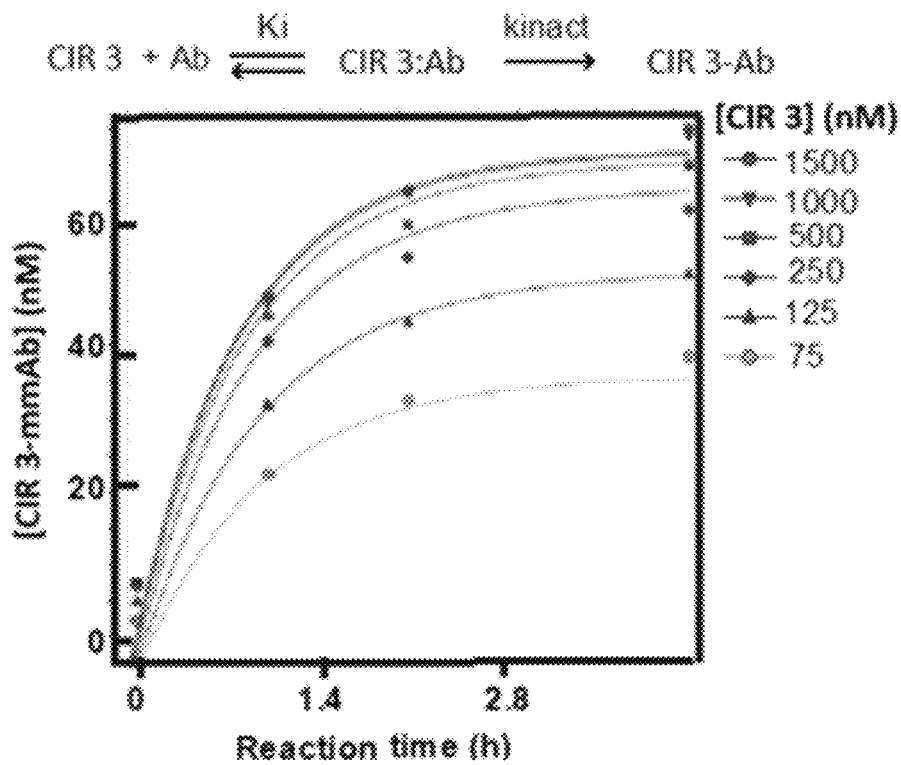

FIG. 9A shows anti-DNP mmAb (75 nM) and CIR 3 (500 nM) covalent labeling kinetics. The increase in labeled antibody (CIR 3-Ab) with time leads to a greater fraction of Fc probes occupied by product vs. unreacted antibody, consistent with increased formation of covalent CIR-Ab complexes (note: CIR only remains on the probe when linked covalently to anti-DNP). Control experiments employed non-DNP binding human IgG (75 nM) or ARM 11 (1500 nM). Using either the control antibody or ARM 11, which lacks the reactive acylimidazole group, showed baseline signal. CIR 5 demonstrated similar kinetics to CIR 3, confirming a similar binding affinity and hydrolytic stability. FIG. 9B shows a plot of increasing PSMA binding amplitude with time (proportional to CIR-Ab formation) from data presented in FIG. 9A, analyzed via numerical integration methods using Dynafit software to extract kinetic constants. Repeating the kinetics assay at increasing concentrations of CIR and a fixed anti-DNP concentration, yields saturation kinetics from which the first order antibody labeling rate constant ($k_{inact}$), can be determined. $k_{inact}$ describes the intramolecular labeling reaction within the CIR:mmAb complex. This analysis also generated a kinetic constant ($K_I$)≈30 nM proportional (and under certain conditions equivalent) to the binding dissociation constant $K_{d(Ab)}$. Resulting saturation kinetics could be analyzed using numerical integration methods, to extract a second order rate constant $k_{inact}/K_I$≈12000 M$^{-1}$ s$^{-1}$ for CIR-Ab formation (Table 1).

Figure 10A:
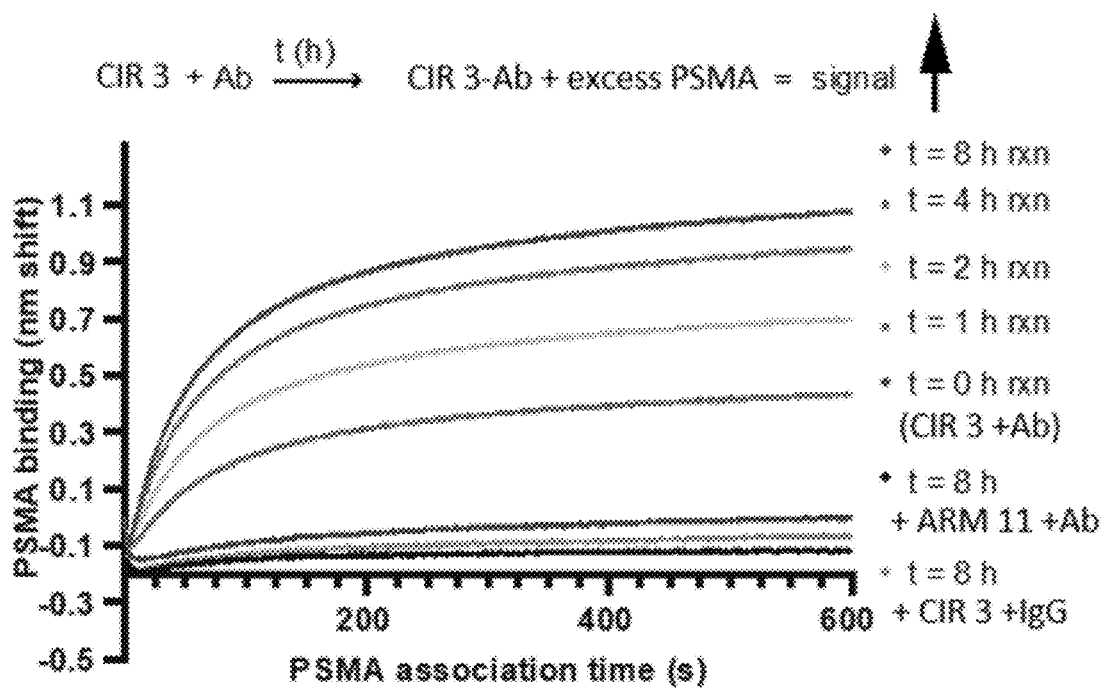
FIGS. 10A to 10D are graphs of antibody recruiting assays and evaluation of immune recognition of targets of an exemplary compound of the application and a comparative non-covalent compound using monoclonal human anti-DNP.
Figure 10B:
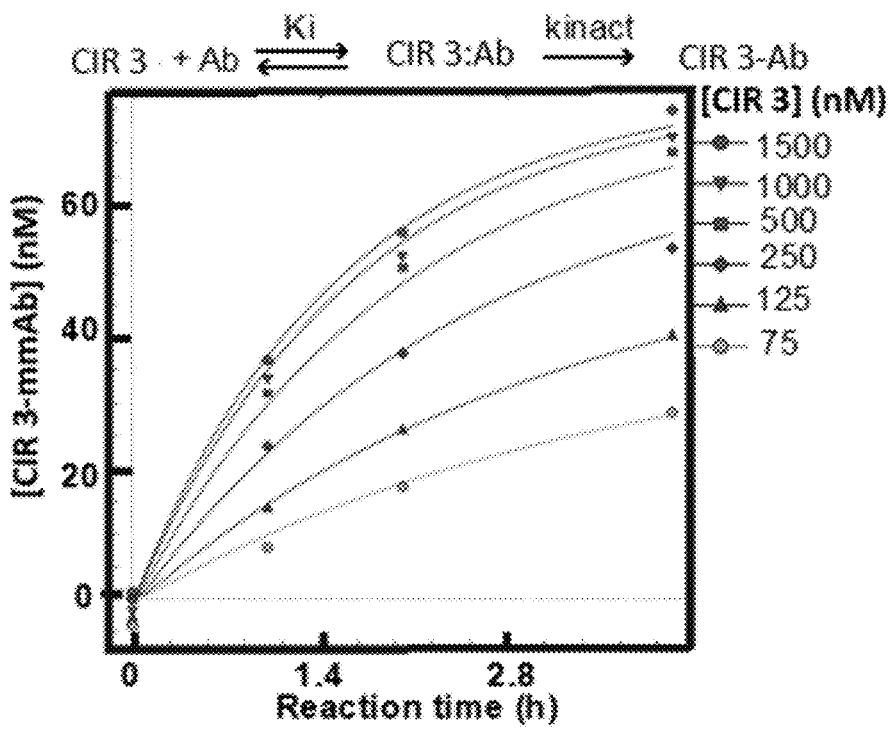

FIG. 10A shows covalent labeling kinetics using anti-DNP mAb (75 nM) and CIR 3 (500 nM) covalent labeling kinetics. Control experiments employed non-DNP binding human control IgG (75 nM) or ARM 11 (1500 nM). FIG. 10B shows a plot of increasing PSMA binding amplitude with time (proportional to CIR-Ab formation) from data presented in FIG. 10A, analyzed via numerical integration methods using Dynafit software to extract kinetic constants, and repeated at increasing concentrations of CIR and a fixed anti-DNP concentration to extract $k_{inact}$ and $K_I$. CIR 3 was again observed to selectively covalently modify mAb albeit with modestly slower kinetics due to a weaker binding affinity for DNP on CIR. The observation of saturation kinetics is consistent with a binding dependent and selective covalent antibody labeling reaction as observed for the CIR 3+mmAb reaction. Despite the unknown structure and sequence of anti-DNP mAb IgG, the determination of a similar $k_{inact}$ to mmAb suggests that mAb is also reacting through a single or select few lysine residues proximal to its DNP binding site.

Evaluating CIR Versus ARM Immune Recognition Using ADCC and ADCP Assays

Covalent vs. non-covalent antibody recruitment were compared in functional immune assays. Activation of NK cell CD16α immune receptors was assessed via luminescence based ADCC assays. ADCC was quantified using the ADCC Reportor Bioassay kit (Promega G7010). All ADCC induced luminescence was measured on a SpectraMax i3 plate reader (Molecular Devices). The human IgG isotype control used was purchased from Jackson ImmunoResearch (009-000-003). The human IgG1 monoclonal anti-DNP antibody (mAb) was purchased from Acrobiosystems (DNP-M2). Human IgG from serum was purchased from Innovative Research (IHUIGGAP1000MG). Anti-DNP depleted serum was made from human IgG from serum (Innovative Research). For PSMA competition controls, 2-PMPA was purchased from Sigma (SML1612). Hek-293T (PSMA+/−) cell lines were generously given by Dr. Cyril Barinka (Institute of Biotechnology CAS, Czech Republic). Ultra low IgG FBS was purchased from Fischer Scientific (A3381901). RPMI-1640 was purchased as a powder from Fischer Scientific (31800089) and resuspended. DMEM was purchased as a powder from Fischer Scientific (12800082) and resuspended. Pen/Strep was purchased from Fischer Scientific (15140-122). FBS was purchased from Fischer Scientific (12484-028). Zeocin was purchased from Fischer Scientific (R25001). HEK-PSMA cells were cultured in DMEM media with 2 mM L-glut, 1% Pen/Strep, 10% FBS, 50 ug/mL Zeocin. HEK cells were cultured in DMEM media with 2 mM L-glut, 1% Pen/Strep, 10% FBS.

Preparation of antibody-CIR/ARM stocks were mixed overnight prior to addition to the ADCC plate. In the case of mmAb and mAb, incubation was carried out at 600 nM antibody and 1.2 µM CIR or ARM. In the case of IgG from serum, incubation was completed at 230 µM antibody and 8.7 µM CIR or ARM. In all cases, DMSO was kept close to 1%. After the overnight incubation, a dilution series was completed on the antibody-CIR/ARM stocks in RPMI (1% DMSO). Target cells were seeded at a density of 2.5×10$^4$ cells per well in opaque 96 well flat-bottom plates (Corning Costar, 3917) in complete media. Sixteen hours after seeding, cells were washed gently with 100 μL of neat RPMI. To the cells, 25 μL of RPMI supplemented with 4% ultra-low IgG FBS was added followed by 25 μL of antibody+/−CIR/ARM conditions described above. After a 30-minute incubation, 25 μL of supplemented RPMI containing $7.5 \times 10^4$ Jurkat effector cells expressing human FcgRIIIa ($CD_{16}$) were added to each well. The plates were then incubated for 6 additional hours. 75 μL of Bio-Glo Luciferase Assay Reagent was added to each well, and luminescence was quantified using the SpectraMax i3 plate reader.

The labeling reaction was first carried out with mmAb anti-DNP antibodies to consume all free CIR and form covalent complexes (CIR 3-Ab). ARMs were also pre-equilibrated with mmAb to consume all free ARM and form non-covalent complexes (ARM 11:Ab). Different dilutions of these solutions were then added to PSMA expressing target cells (PSMA+) in the presence of CD16α immune receptor expressing Jurkat T cells. This assay format was chosen to model the therapeutically relevant scenario, wherein ARMs are administered by I.V. to complex all available anti-DNP present in human serum prior to localization to cancer cells. Complex formation can occur either covalently (via CIRs) or reversibly (via ARMs). The different dilutions of CIR-Ab and ARM:Ab solutions, therefore reflect how different natural concentrations of serum anti-DNP antibody potential present in a subject, govern ARM or CIR antibody recruitment to target cells and immune recognition.

Figure 9C:
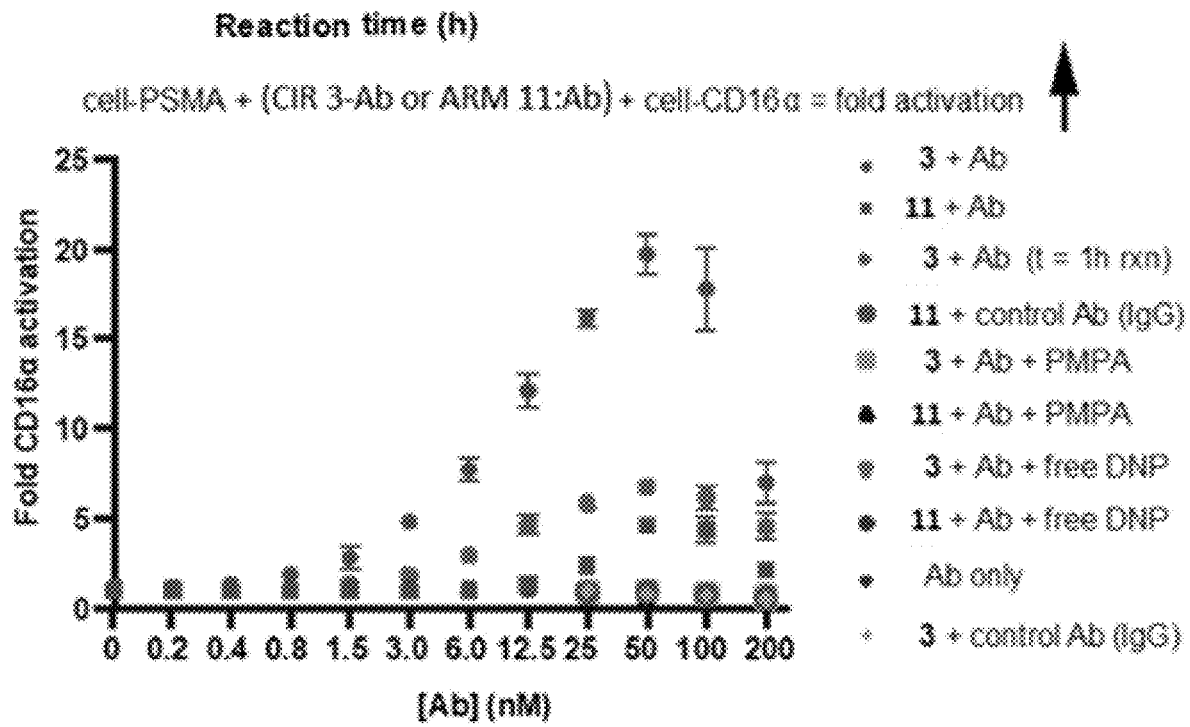
Figure 9D:
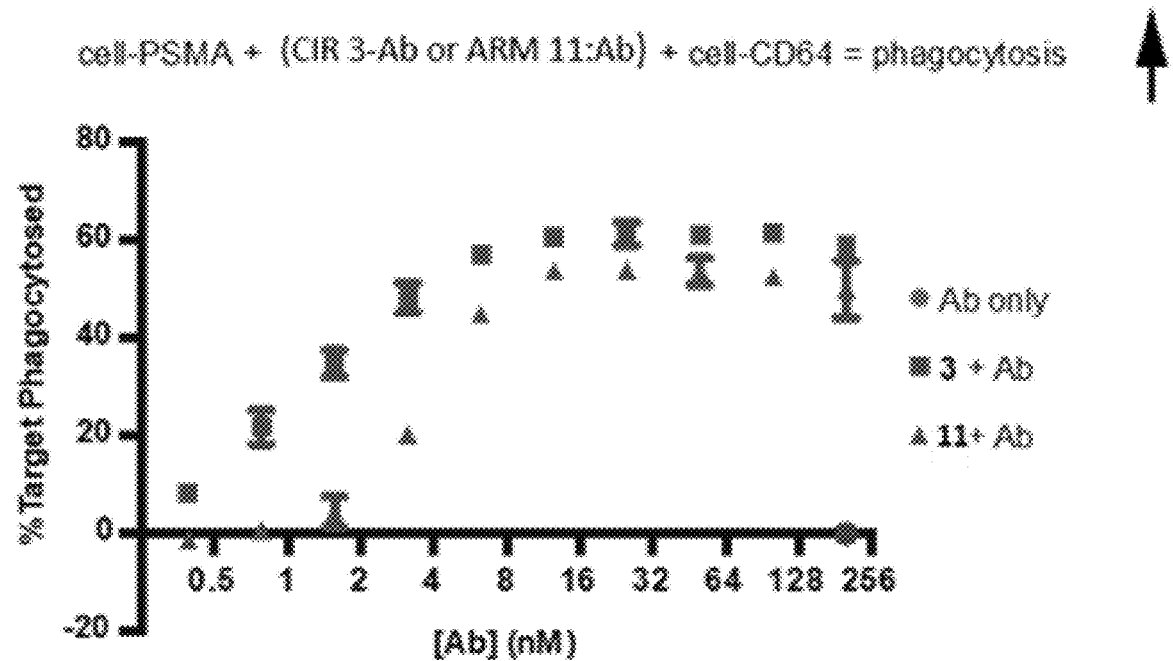
Figure 9E:
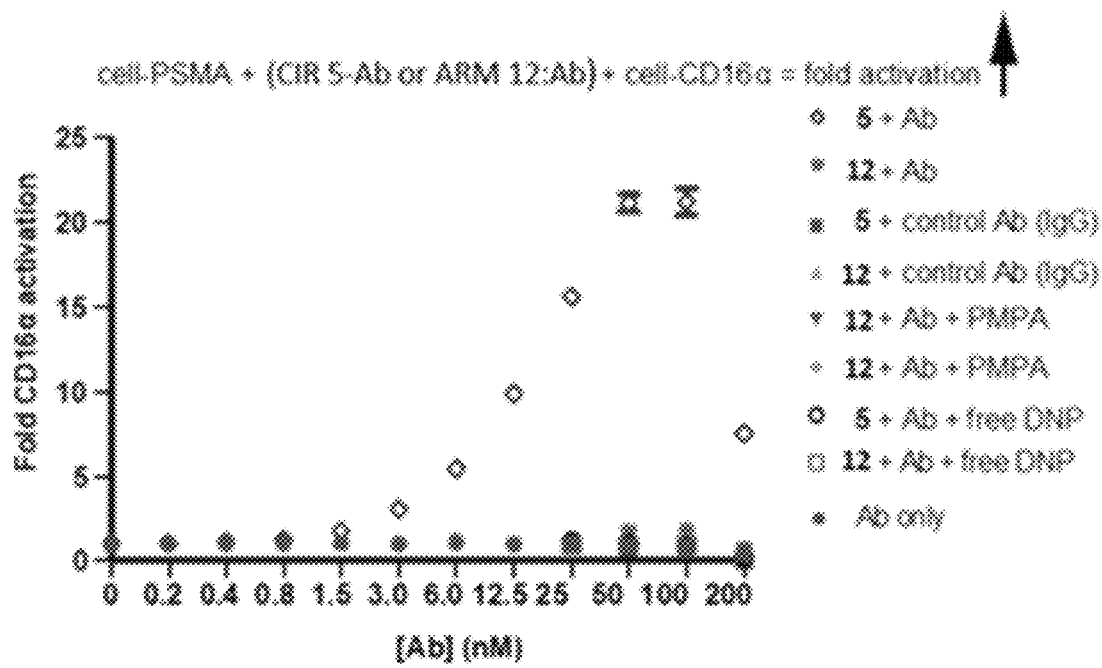

FIG. 9C shows CD16α based target immune recognition of target PSMA+HEK cells mediated by CIR 3 and ARM 11 while FIG. 9E shows these experiments using CIR 5 and ARM 12. Antibody complexes were prepared by incubating anti-DNP IgG mmAb (600 nM) with 2 eq. CIR or ARM overnight prior to dilutions directly into PSMA+HEK cell media solutions at 37° C., followed by the addition of Jurkat T cells. Jurkat T cells are engineered to couple antibody dependent CD16α activation to luciferase expression, resulting in a detectable "fold activation" signal increase. Control experiments involved the addition of 12 mM free DNP glycine competitor, or 6 mM PMPA to cell solutions. An additional control involved incubating CIR with human IgG control antibody (control Ab) in place of anti-DNP mmAb. In these assays, it was observed that non-covalent antibody recruitment via ARM 11 or ARM 12 was largely unable to mediate immune recognition of target HEK cells across a biologically relevant range of potential serum antibody concentrations ($10^{-7}$-$10^{-9}$ M). Covalent antibody recruitment by CIR 3 or CIR 5 however led to robust target immune recognition demonstrating function even at low $10^{-9}$ M concentrations of mmAb antibody. Key control experiments using: a) free DNP which inhibits non-covalent antibody binding (and reaction) with anti-DNP, b) the competitive PSMA binding inhibitor 2-(phosphonomethyl)pentanedioic acid (2-PMPA), which inhibits CIR or ARM binding to PSMA and c) non-DNP binding monoclonal control IgG antibody which can react with CIRs bimolecularly but not bind the DNP hapten, were shown to significantly decrease CD16α activation. These control experiments support the selective covalent recruitment of anti-DNP antibodies to cell surface PSMA. Despite containing abundant reactive lysine residues, monoclonal human control IgG cannot be covalently recruited by CIR 3 or CIR 5 since the selective reaction cannot be templated through a binding interaction. Control IgG shares the same Fc hinge domain as mmAb and therefore binds CD16α with the same affinity ($K_d$, ≈, $10^{-6}$ M) but requires recruitment to target cells in order to cluster and activate CD16a. An additional control was included where CIR 3 was incubated with mmAb for only 1 hr preventing complete reaction conversion which leads to a mixture of covalent CIR-Ab and non-covalent CIR:Ab complexes. As anticipated, this attenuated CD16α activation, consistent with the lack of function associated with non-covalent antibody recruitment (FIG. 9C). A bell-shaped dose response curve was also observed as the CIR 3-Ab concentration was increased. This is consistent with a ternary complex binding equilibrium between CIR 3-Ab, PSMA, and $CD_{16}\alpha$ that governs immune recognition. Excess CIR 3-Ab drives the dissociation of immunologically active complexes via competitive binding interactions with $CD_{16}\alpha$ (autoinhibition). Although predominant antibody dependent cancer immune recognition mechanisms involve $CD_{16}\alpha$ activation on NK cells, monocytes and macrophages also play an important role via antibody dependent activation of $CD_{64}$ receptors on their cell surface leading to phagocytosis of cancer cells. Therefore, the effects of covalent vs. non-covalent antibody recruitment on $CD_{64}$ mediated target immune recognition of HEK PSMA+targets were tested. For this, a two colour ADCP flow cytometry assay with CIR 3 and ARM 11 was used.

ADCP flow cytometry experiments were run on a BD LSRII Flow Cytometer. The human IgG isotype control used was purchased from Jackson ImmunoResearch (009-000-003). The human IgG1 monoclonal anti-DNP antibody (mAb) was purchased from acrobiosystems (DNP-M2). PSMA expression was confirmed with an anti-PSMA antibody Alexa 647 conjugate (Novus Biologicals, Catalog #FAB4234R). For PSMA competition controls, PMPA was purchased from Sigma (SML1612). Hek-293T (PSMA+/−) cell lines were generously given by Dr. Cyril Barinka (Institute of Biotechnology CAS, Czech Republic). U937 cells were generously given by Dr. John Valliant (McMaster University, Canada). LNCaP cells were generously given by Dr. Karen Mossman (McMaster University, Canada). IFN-γ was purchased from Fischer Scientific (PHC4031). Ultra low IgG FBS was purchased from Fischer Scientific (A3381901). RPMI-1640 was purchased as a powder from Fischer Scientific (31800089) and resuspended. DMEM was purchased as a powder from Fischer Scientific (12800082) and resuspended. DiD cell dye was purchased from Fischer Scientific (V22887). DiO cell dye was purchased from Fischer Scientific (V22886). TrypLE Express was purchased from Fischer Scientific (12604013). 96-Well U-bottom plates were purchased from FischerScientific (08-772-17). Pen/Strep was purchased from Fischer Scientific (15140-122). FBS was purchased from Fischer Scientific (12484-028). Zeocin was purchased from Fischer Scientific (R25001). HEK-PSMA cells were cultured in DMEM media with 2 mM L-glut, 1% Pen/Strep, 10% FBS, 50 ug/mL Zeocin. HEK cells were cultured in DMEM media with 2 mM L-glut, 1% Pen/Strep, 10% FBS. LNCaP cells were cultured in RPMI media with 1% Sodium Pyruvate, 1% Pen/Strep, 10% FBS. U937 monocytes were cultured in RPMI media with 2 mM L-Glut, 1% Pen/Strep, 10% FBS.

For preparation of effector monocytes, 24 hours prior to inducing phagocytosis U937 monocytes were seeded at 500,000 cells/mL and activated with IFN-γ (0.1 mg/mL). After incubation, these cells were then counted and washed twice with serum free assay media (neat RPMI). Cells were then suspended to a concentration of 1 million cells/mL and stained with 1.9 μM Vybrant DiD Cell-Labelling Solution for 30 minutes (37° C., 5% $CO_2$). Cells were then washed 3× with warm assay media (AM, 14% Ultra Low IgG FBS in RPMI) and resuspended to a concentration of $3.0 \times 10^6$ million cells/mL to be plated for use in assay (50 µL holds 150,000 cells). Prior to overnight incubation, antibody-CIR/ARM experimental and control conditions were prepared. For each antibody condition, antibody-CIR/ARM were incubated together at a ratio of 2:1 (CIR/ARM:Ab) and at a concentration of 4× the top antibody concentration listed. If competitors are used, they are added to the antibody stock solution at a concentration of 5000× excess to CIR/ARM if competing for PSMA, and 10,000× excess if competing for anti-DNP antibody. On the day of the experiment, target cells (90% confluent in a T-150 flask) were suspended with TrypLE and quenched with complete growth media. These cells were then counted and washed twice with serum free assay media (neat RPMI). Cells were then suspended to a concentration of 1 million cells/mL and stained with 5.7 µM Vybrant DiO Cell-Labelling Solution for 30 minutes (37° C., 5% $CO_2$). Cells were then washed 3× with warm assay media (AM, 14% Ultra Low IgG FBS in RPMI) and resuspended to a concentration of $6.0 \times 10^6$ million cells/mL to be plated for use in assay (25 µL holds 150,000 cells). To a U-bottom 96-well plate, 25 µL of target cells followed by 25 µL of each antibody condition were added (for PSMA expressions check, 1.5 µL anti-PSMA A647 antibody added with 25 µL assay media). Next, 50 µL of activated monocytes were added to these wells. The plate was centrifuged at 800 rpm for 2 minutes to pellet cells and placed in a 37° C. 5% $CO_2$ incubator for 1 hour. Plates were placed on ice and all conditions were then run on flow cytometry to determine ADCP. DiO stained cells were detected in the A488 channel, DiD stained cells were detected in the APC Cy7 channel, PSMA expression was confirmed with the Alexa 647 channel. The following voltages were used: FSC: 430, SSC: 290, A488: 260, APC Cy7: 410, A647: 490. ADCP was determined by plotting monocyte stain against bead stain, and was quantified as % Target Phagocytosed= [(Double Positive Events)/(Target Only Events+Double Positive Events)]*100. This was normalized to antibody only control.

CIR 3 or ARM 11 (640 nM) was incubated with 320 nM antibody (mmAb or mAb) at room temperature overnight. After overnight incubation, a dilution series (1:2, 1:3, 1:3) was conducted using each condition stock which was then equilibrated for 90 minutes prior to addition to the assay well plate. HEK293 cells transfected with PSMA, were washed 3× and placed in a flow buffer containing 4% FBS, 0.5 mM EDTA/EGTA, 0.1% Sodium Azide, at a concentration of $2 \times 10^6$ Cells/mL. 75 µL of cells were added (150 000 Cells per sample) and kept on ice. 25 µL of antibody+CIR or antibody+ARM conditions prepared above were added to the target cells (experimental antibody concentrations: 80 nM, 40 nM, 13.3 nM, 4.4 nM, 1.5 nM). For the DNP Control, 4.5 mM was added to antibody for 5 minutes, then the CIR/ARM was added, and the solution incubated overnight. For the 2-PMPA Control, 0.5 mM was added to cells for 5 minutes, then the Ab/CIR solution and Ab/ARM solution was added. Afterwards 1 µL of 0.5 mg/mL Goat anti-Human IgG Fc Secondary Antibody, PE, (Catalog #12-4998-82) was added to every condition, and mixed. Conditions were run in duplicate. PSMA loading/expression was confirmed with an anti-PSMA antibody Alexa 647 conjugate (Novus Biologicals, Catalog #FAB4234R). Voltages were FSC: 330, SSC: 270, Alexa 647: 490, PE: 320.

Figure 9F:
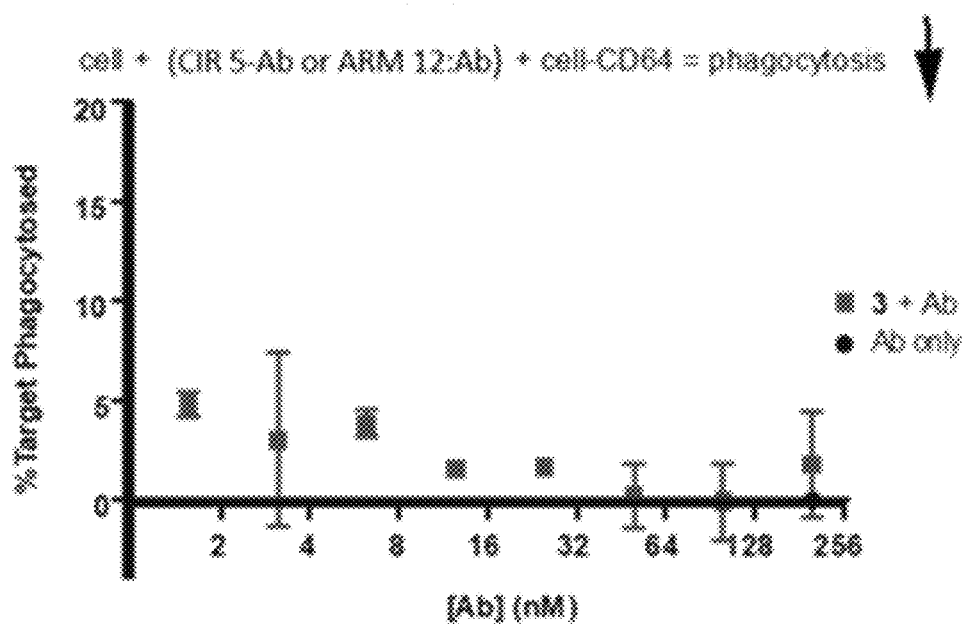

$CD_{64}$ based target immune recognition mediated by CIR 3 and ARM 11 was evaluated in two-colour flow cytometry phagocytosis assays using PSMA+HEK cells in FIG. 9D and using PSMA-isogenic control cell lines in FIG. 9F. Antibody complexes were prepared by incubating anti-DNP IgG mmAb (800 nM) with 2 eq. CIR or ARM overnight prior to dilutions directly into PSMA+HEK cell media solutions at 37° C., followed by the addition of human u937 monocytes. Here, $CD_{64}$-based recognition was measured via phagocytosis of target cells by monocytic immune cells expressing $CD_{64}$ receptor, each stained with a unique membrane dye. In contrast to the case with $CD_{16}\alpha$ based target recognition, covalent antibody recruitment only provided a functional enhancement relative to ARM 11 at low antibody concentrations (FIG. 9D). At higher mmAb concentrations, ARMs and CIRs function with similar efficiencies. Parallel experiments using PSMA-isogenic control cell lines further confirmed $CD_{64}$ based immune recognition is dependent on CIR and ARM binding to cell surface PSMA (FIG. 9F).

Figure 11:
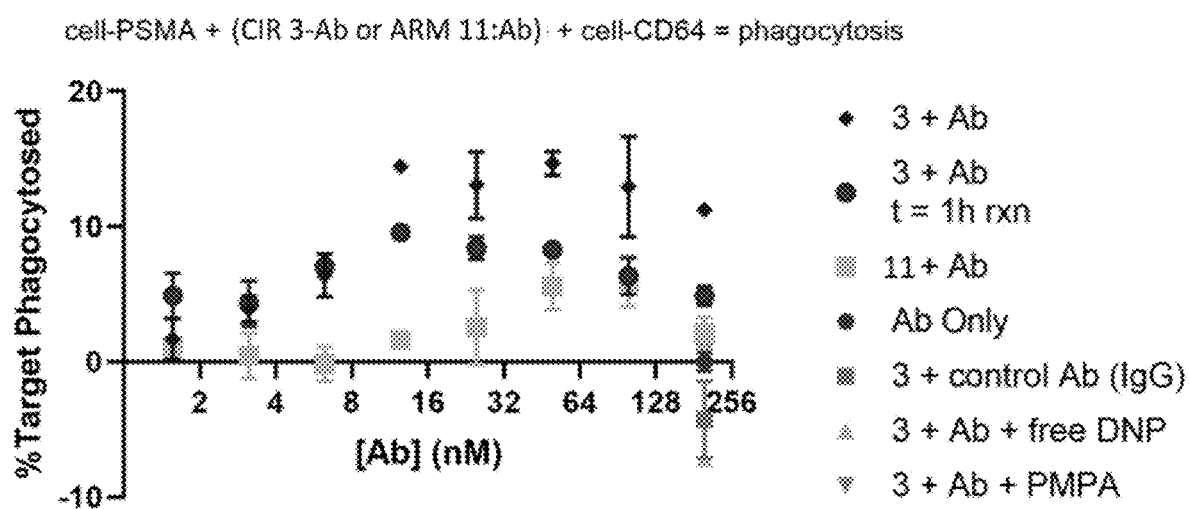
FIG. 11 shows immune recognition of targets of an exemplary compound of the application and a comparative non-covalent compound on PSMA+LNCaP cells using flow cytometry ADCP assays.

CIR 3 vs. ARM 11 in ADCP assays were also evaluated in the context of lower PSMA expressing LNCaP cells which could not be used in the above $CD_{16}\alpha$ activation assay. This is because antibody dependent $CD_{64}$ activation does not require as high a density of cell associated antibodies as $CD_{16}\alpha$ activation, which is dictated by the number and density of cancer receptor binding sites (i.e. PSMA). FIG. 11 shows CIR 3 or ARM 11 induced ADCP with mmAb on LNCaP target cells. Comparison of CIR 3 and ARM 11 mediated immune receptor complex formation with mmAb on PSMA+LNCaP cells, was determined using a flow cytometry-based ADCP assay. Interestingly, in these ADCP studies, covalent antibody recruitment again demonstrates a significant functional advantage compared to non-covalent recruitment across all antibody concentrations tested. Taken together, these results demonstrate that covalent stabilization of ARM:Ab complexes enhances target immune recognition across a range of therapeutically relevant anti-DNP IgG antibody concentrations. Interestingly, this enhancement occurs despite the model anti-DNP antibody (mmAb) already having a relatively strong affinity for ARMs forming thermodynamically stable ARM:Ab complexes.

Figure 10C:
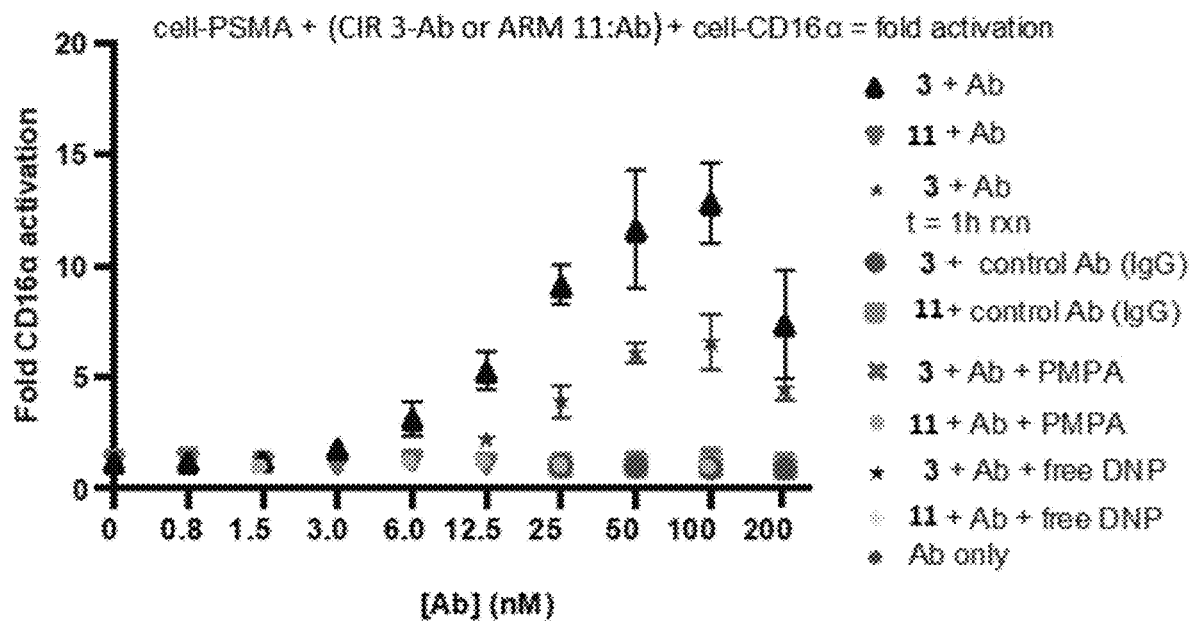
Figure 10D:
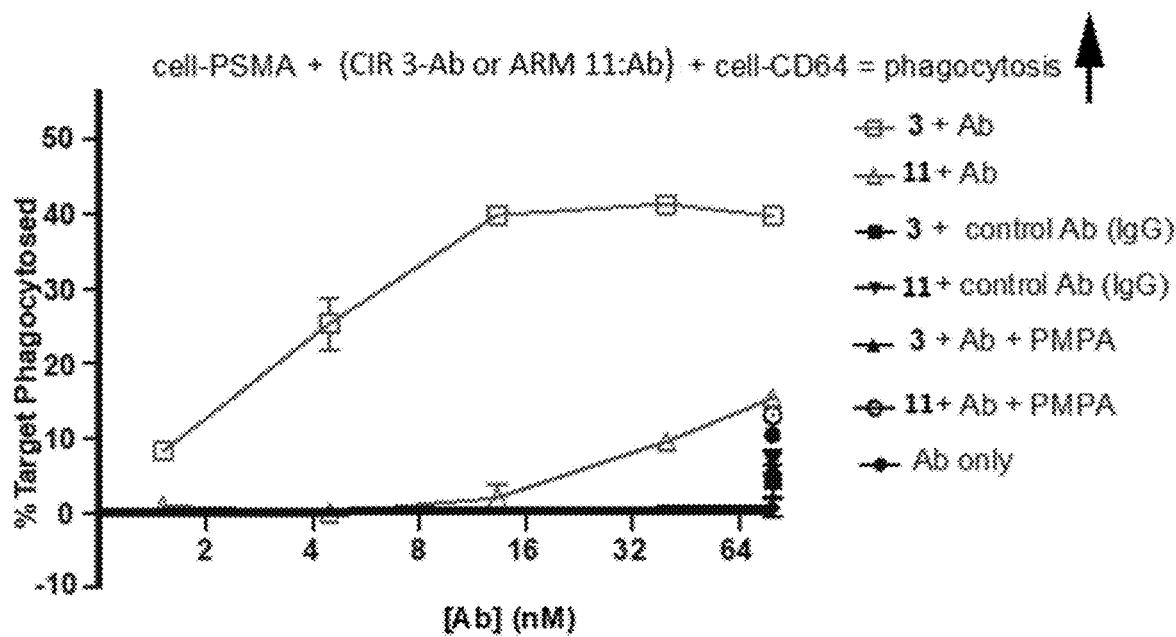

The effects of covalent vs. non-covalent anti-DNP mAb recruitment on both $CD_{16}\alpha$ and $CD_{64}$ based modes of target immune recognition were next evaluated as a comparison to using mmAb. FIG. 10C shows $CD_{16}\alpha$ based target immune recognition of target PSMA+HEK cells mediated by CIR 3 and ARM 11. Antibody complexes were prepared by incubating anti-DNP IgG mAb (600 nM) with 2 eq. CIR or ARM overnight prior to dilutions directly into PSMA+HEK cell media solutions at 37° C., followed by the addition of Jurkat T cells. Control experiments involved the addition of 5 mM free DNP glycine competitor, or 2.5 mM PMPA to cell solutions. An additional control involved incubating CIR 3 with human IgG control antibody (control Ab) in place of anti-DNP mAb. In these $CD_{16}\alpha$ receptor activation assays, it was again observed that non-covalent antibody recruitment via ARM 11 was largely unable to mediate immune recognition of target HEK cells across the biologically relevant range of antibody concentrations tested ($10^{-7}$-$10^{-9}$ M). Covalent antibody recruitment of the weaker affinity anti-DNP mAb by CIR 3 also demonstrated similar functional potency and efficacy to that observed using mmAb. Control experiments using PSMA competitive binding ligand 2-PMPA and non-DNP binding control IgG antibody again significantly decreased $CD_{16}\alpha$ activation. The incubation of CIR 3 with mAb for only 1 hour preventing complete reaction conversion again led to attenuation of $CD_{16}\alpha$ activation. FIG. 10D shows $CD_{64}$ based target immune recognition of target PSMA+HEK cells mediated by CIR 3 and ARM 11, evaluated in two-color flow cytometry phagocytosis assays. Antibody complexes were prepared by incubating anti-DNP IgG mmAb (320 nM) with 2 eq. CIR or ARM overnight prior to dilutions directly into PSMA+HEK cell media solutions at 37° C., followed by the addition of human u937 monocytes. In agreement with results of $CD_{16}\alpha$ receptor activation assays, covalent antibody recruitment in ADCP assays provided a substantial functional enhancement relative to ARM 11 across all antibody concentrations tested. This was in contrast to the results obtained in ADCP assays using higher affinity antibody mmAb. Select control conditions confirmed ADCP was dependent on selective binding to PSMA (+PMPA) and mAb anti-DNP antibody (+free DNP), and in the case of CIR, dependent on the selective covalent labeling of anti-DNP antibody (control Ab). Taken together, these results demonstrate that the CIR strategy can be used to efficiently covalent recruit weaker affinity antibody to target receptors and exert a functional advantage relative ARMs.

Evaluation of CIR Versus ARM Antibody Recruitment to the Surface of PSMA Expressing Target Cells by Flow Cytometry Elimination equilibrium of the ARM:antibody through a covalent linkage to CIRs, and its impact on total antibody recruitment to target cells, at different therapeutically relevant antibody concentrations was next evaluated. This was done to determine if the covalent enhancement observed in functional assays was due to increased antibody recruitment to target cells. Identical dilution experiments described above for functional assays with (CIR-Ab) and non-covalent (ARM:Ab) complexes on PSMA+target cells, using both mAb and mmAb anti DNP antibodies were performed. These studies were also done at 37° C. as above in functional assays, to accurately report on the levels of antibody recruitment governing target cell immune recognition. In these assays, fluorescently labeled secondary IgG antibody (anti-IgG) was used in place of immune cells, to detect antibody recruited to the cell surface. Anti-DNP antibody recruited to target cells via ARMs can subsequently bind fluorescent secondary antibody. This leads to increases in the mean fluorescence intensity (MFI) of associated cell populations, detectable in flow cytometry.

Figure 12A:
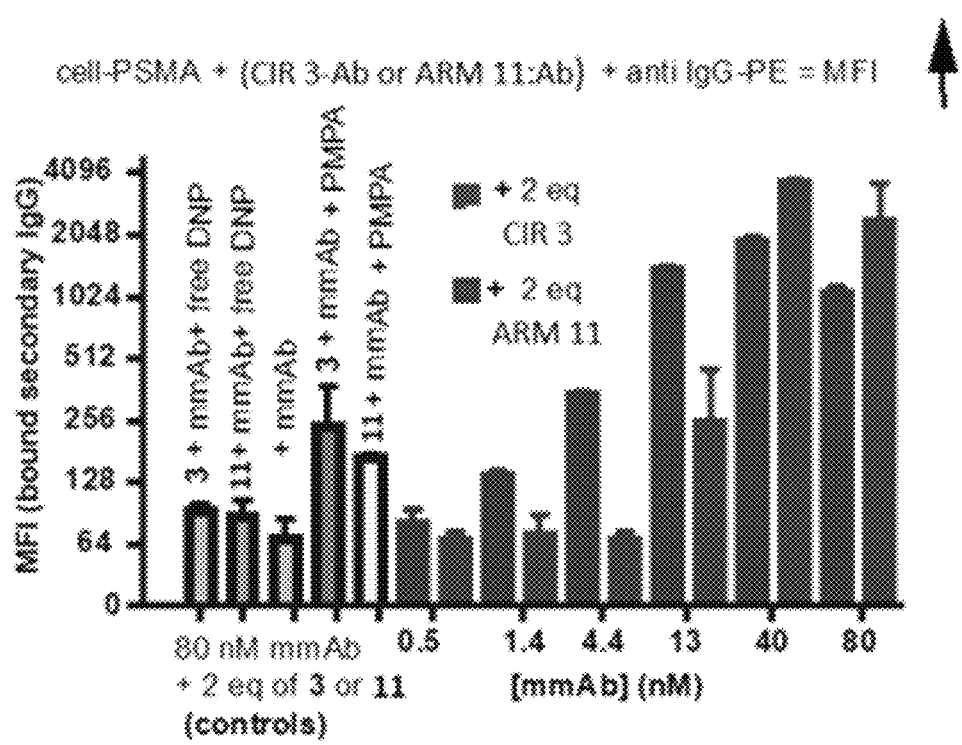
FIGS. 12A and 12B are graphs of the evaluation of immune recognition of targets via antibody recruitment of an exemplary compound of the application and a comparative non-covalent compound.
Figure 12B:
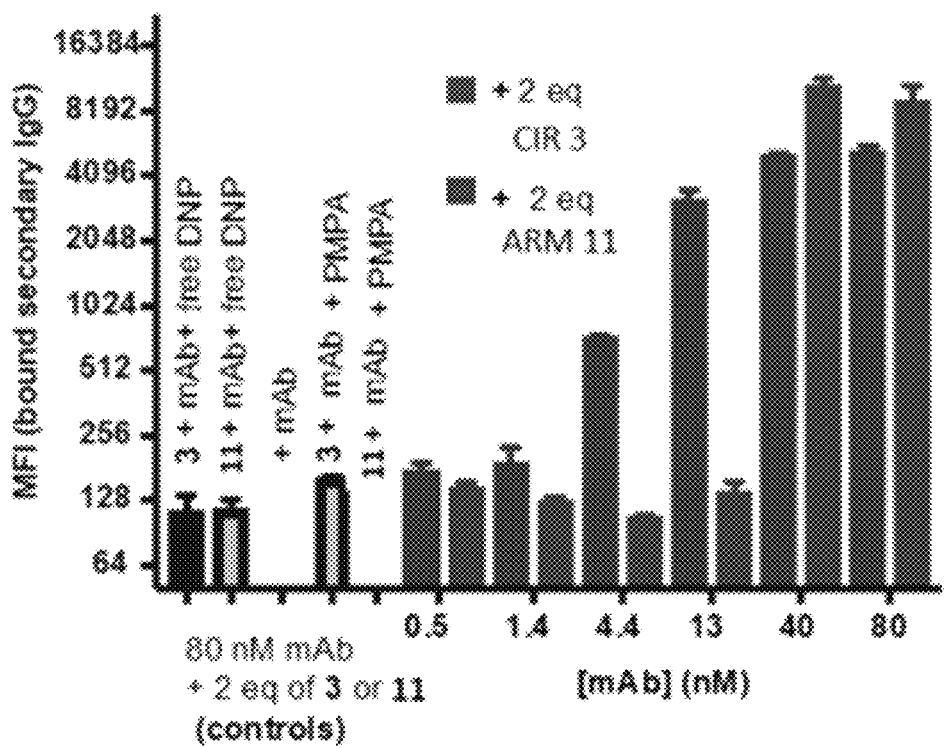

FIG. 12 shows evaluation of covalent (CIR 3) vs non-covalent (ARM 11) total antibody recruitment to target HEK PSMA+cells via flow cytometry. Specifically, FIG. 12A shows anti-DNP mmAb recruitment to the cell surface while FIG. 12B shows anti-DNP mAb recruitment to the cell surface detected via flow cytometry, using fluorescently (PE) tagged anti-human IgG secondary antibody. Antibody recruitment to the cell surface is proportional to the mean fluorescence intensity (MFI) of cell populations, bound to mmAb antibody complexes comprising CIR 3 or ARM 11. Antibody complexes were prepared by incubating anti-DNP IgG mmAb (320 nM) with 2 eq. CIR or ARM overnight prior to dilutions directly into PSMA+HEK cell media solutions at 37° C. Control experiments employed 4.5 mM free DNP glycine competitor, or 0.5 mM PMPA. In these experiments, at sub-saturating mAb or mmAb antibody concentrations (<40 nM) used in functional assays above, CIR 3 was observed to enable more total antibody recruitment to the target cell surface compared to ARM 11. At higher antibody concentrations (40-80 nM) both covalent and non-covalent approaches recruit anti-DNP with comparable efficiencies. Control experiments confirmed antibody recruitment was selective for anti-DNP IgG against PSMA expressing target cells. In these experiments, the addition of free DNP or the PSMA binding inhibitor PMPA resulted in a significant decrease in cell MFI signal. Taken together, the results of antibody recruiting assays demonstrate that at sub-saturating antibody concentrations (i.e. [Ab]<10× $K_{d(Ab)}$), covalent stabilization enables increased antibody recruitment to target cells. Interestingly, CIR and ARM both recruit comparable amounts of mAb and mmAb to the target surface when [Ab]>40 nM and appear to saturate all available PSMA binding sites. This result suggests that the functional covalent enhancement observed in FIGS. 9-10 at antibody concentrations beyond 40 nM mAb or mmAb, is not only due to enhanced antibody recruitment relative to ARMs.

Evaluation of CIR Versus ARM Recruitment of Human Serum Anti-DNP IgG on Immune Receptor Activation To determine if actual human serum anti-DNP IgG (sAb) isolated directly from serum can be covalently recruited to target cells and activate immune receptor function, a protocol to isolate and characterize endogenous human anti-DNP antibodies from human serum was first developed. DNP hapten coated BSA beads were used to extract anti-DNP IgG from pan IgG antibodies, pre-isolated from pooled human serum. Anti-DNP specific antibody was quantified using BLI. The concentration of anti-DNP antibody isolated was determined by looking at the binding of the isolated antibody sample to ARM 9 loaded onto Streptavidin probes on the Octet Red96. The amplitude of anti-DNP antibody binding to probe-ARM after 5 minutes of association was compared to a standard curve constructed using 5-100 nM of mmAb in PBS to calculate anti-DNP concentration. The equation of the standard curve is: nm shift amplitude=0.04779 (Ab concentration in nM)−0.1918. This equation was derived using the 'simple linear regression' model in GraphPad Prism 8. This method of antibody quantification relies on the assumption that the isolated serum antibody has a similar binding affinity for probe-ARM as mmAb. However, as seen from Table 1 and FIG. 12A, it is likely that mmAb has a higher affinity ($K_d$~80 nM) for the DNP hapten of ARM 9 than the isolated serum antibody ($K_d$~460 nM). This means that at the same fixed concentration of antibody, more mmAb than isolated serum antibody would bind to the probe. More mmAb binding to the probe would result in a higher nm shift amplitude for the mmAb sample compared to the serum antibody at the same concentration, as mass increases the nm shift amplitude. As a result, the standard curve could have underestimated the concentration of serum antibody isolated as the nm shift values reported for each concentration in the curve may be higher than they would be for serum antibody binding. The nm shift amplitude of the isolated anti-DNP antibody sample was 2.83. When this value is substituted into the equation from the standard curve, the concentration of anti-DNP antibody isolated from serum is calculated to be 63 nM.

The concentration of endogenous anti-DNP antibody in pooled human serum was estimated by comparing the fraction of anti-DNP isolated using affinity chromatography compared to the total IgG concentration in the sample loaded onto the column. From the affinity column, 0.5 mL of 63 nM anti-DNP antibody was isolated. As the molecular weight of IgG is 150 kDa, 63 nM of anti-DNP antibody is about 0.00945 mg/mL. Therefore, the total amount of anti-DNP antibody isolated from 109.2 mg (3 mL of 36.4 mg/mL) of human serum IgG was 0.00472 mg (0.5 mL×0.00945 mg/mL). The fraction of anti-DNP IgG in the human serum IgG sample is $4.3 \times 10^5$, as seen in the following calculation: amount of anti-DNP antibody in sample/total amount of antibody in sample=fraction of anti-DNP IgG. The concentration of IgG in human serum is assumed to be 7-16 mg/ml. Using an average value of 11.5 mg/mL, the concentration of anti-DNP IgG in human serum would be $5.0 \times 10^{-4}$ mg/mL, which is on the order of $10^{-9}$ M. This value was calculated using: concentration of IgG in serum X fraction of anti-DNP IgG in serum IgG=concentration of anti-DNP Ab in serum. This same method was used to estimate the concentration of endogenous anti-DNP Ab in the pan IgG solution used in $CD_{16}\alpha$ activation assays. This pan IgG solution was estimated to have an endogenous anti-DNP antibody concentration of 10 nM and this value was calculated using: concentration of pan IgG X fraction of anti-DNP IgG in total IgG=concentration of anti-DNP in pan IgG. Total IgG concentration was determined using the initial binding rate of the isolated antibody sample to ProG probes on the Octet Red96. ProG probes are Fc capture probes that bind the Fc portion of specifically IgG antibodies. A higher concentration of IgG would result in more IgG initially loading onto the probe (a higher initial rate) before an equilibrium can be established. The initial binding rate of antibody to the probe was measured by monitoring antibody binding (nm shift) over time for the first 20 seconds the probe was placed in the antibody solution. The initial binding rate was then linearly derived from the curve of antibody binding (nm shift) over time using the 'calculate binding rate' option of 'quantitation' method in the Octet Systems Data Analysis software. A standard curve was constructed using 5-5000 nM of mmAb in PBS. The equation of the standard curve is (binding rate, $s^{-1}$)=0.0001852 (IgG concentration, nM)+0.03719 and was derived using the 'simple linear regression' model on GraphPad Prism 8. The serum IgG sample depleted of anti-DNP was first diluted 1:10 in PBS before being quantified. The initial binding rate of the anti-DNP depleted serum IgG sample was 0.639 $s^{-1}$, which calculated to 3250 nM of IgG in the sample. Taking into account the 1:10 dilution, the total concentration of IgG in the anti-DNP depleted serum IgG sample was 32 µM.

Affinity analysis of isolated anti-DNP antibody via BLI was conducted using the same protocol as mmAb with ARM 9. Association of the isolated anti-DNP antibody to ARM 9 was measured by placing the probe into a solution of 60 nM isolated anti-DNP antibody for 5 minutes. Dissociation of antibody from ARM 9 was measured by placing the probe in 1×Kinetics Buffer for 10 minutes. The experiment was repeated twice, with an isolated anti-DNP antibody concentration of 50 nM and 40 nM respectively, for a total of three replicates. Anti-DNP IgG was isolated from human serum IgG (Cedarlane Labs) using affinity chromatography. The enriched anti-DNP antibody sample had 63.19 nM of anti-DNP antibody in 1.92 µM of total IgG. The enriched antibody sample was reacted with 2.5 µM of CIR 3 in PBS overnight at room temperature. A sample of 32.75 µM IgG that was depleted of anti-DNP antibody was also reacted with 2.5 µM of CIR 3 in PBS overnight at room temperature as a negative control.

The ability of CIR 3 to recruit the tumour antigen PSMA to anti-DNP antibodies was measured using BLI. Anti-DNP IgG was isolated from human serum IgG (Cedarlane Labs) using affinity chromatography. The enriched anti-DNP antibody sample had 63.19 nM of anti-DNP antibody in 1.92 µM of total IgG. The enriched antibody sample was reacted with 2.5 µM of CIR 3 in PBS overnight at room temperature. A sample of 32.75 µM IgG that was depleted of anti-DNP antibody was also reacted with 2.5 µM of CIR 3 in PBS overnight at room temperature as a negative control. The BLI experiment was conducted using an Octet Red96 (ForteBio) with the temperature set at 25° C., the RPM set at 1000, and the acquisition rate set at 5 Hz. The isolated anti-DNP and CIR 3 reaction samples were suspended in 1×Kinetics Buffer (ForteBio) by doping in a 1:10 dilution of 10×Kinetics Buffer stock. A volume of 200 µL of each solution was loaded into a black flat-bottom 96-well plate (Grenier). Fc capture (ProG) biosensors from ForteBio were placed in 1×Kinetics Buffer for 20 minutes prior to the experiment for wetting. First, the probes were placed in 1×Kinetics Buffer for 4 minutes to establish a baseline. Then the probes were submerged in the antibody-CIR 3 reaction sample for 3 minutes to load the antibodies onto the probe. After the loading step, the probes were submerged for 20 minutes in 5 mM DNP-glycine in Kinetics Buffer, which acts as a competitor to disrupt any non-covalent interactions between CIR 3 and the antibodies. A wash step where the probe was submerged in 1× Kinetics Buffer for 10 minutes to allow any non-specific interactions to dissociate from the probe was repeated eight times and a different well of 1×Kinetics Buffer was used for each repeat. Association of PSMA to the probe was measured by submerging the probe in 500 nM PSMA for 10 minutes. Dissociation of PSMA from the probe was measured by submerging the probe in 1×Kinetics Buffer for 10 minutes.

FIG. 13 shows evaluation of the effects of covalent versus non-covalent recruitment of endogenous human serum anti-DNP IgG, on immune receptor activation. Specifically, FIG. 13A shows characterization of endogenous sAb binding affinity for ARM 9 immobilized on streptavidin probes using BLI. Depleted serum IgG is derived from pan serum human IgG passed through DNP coated beads to remove endogenous anti-DNP IgG. FIG. 13B shows, analogous to experiments in FIG. 9, use of BLI Fc capture probes to validate CIR 3 selective covalent recruitment of endogenous sAb versus non-DNP binding "depleted" human serum pan IgG. FIG. 13C shows, analogous to experiments in FIGS. 9-10, Promega $CD_{16}\alpha$ activation assays were used to study the effects of covalent vs. non-covalent antibody recruitment on immune receptor activation using sAb. In these assays CIR 3 or ARM 11 (8.7 µM) was added directly to pan human IgG (non-depleted 230 µM) as a source of endogenous sAb. Controls were included analogous to those described for experiments in FIGS. 9-10. FIG. 13D shows select conditions used in FIG. 13C in the context of isogenic control HEK cell lines lacking PSMA expression.

Figure 13A:
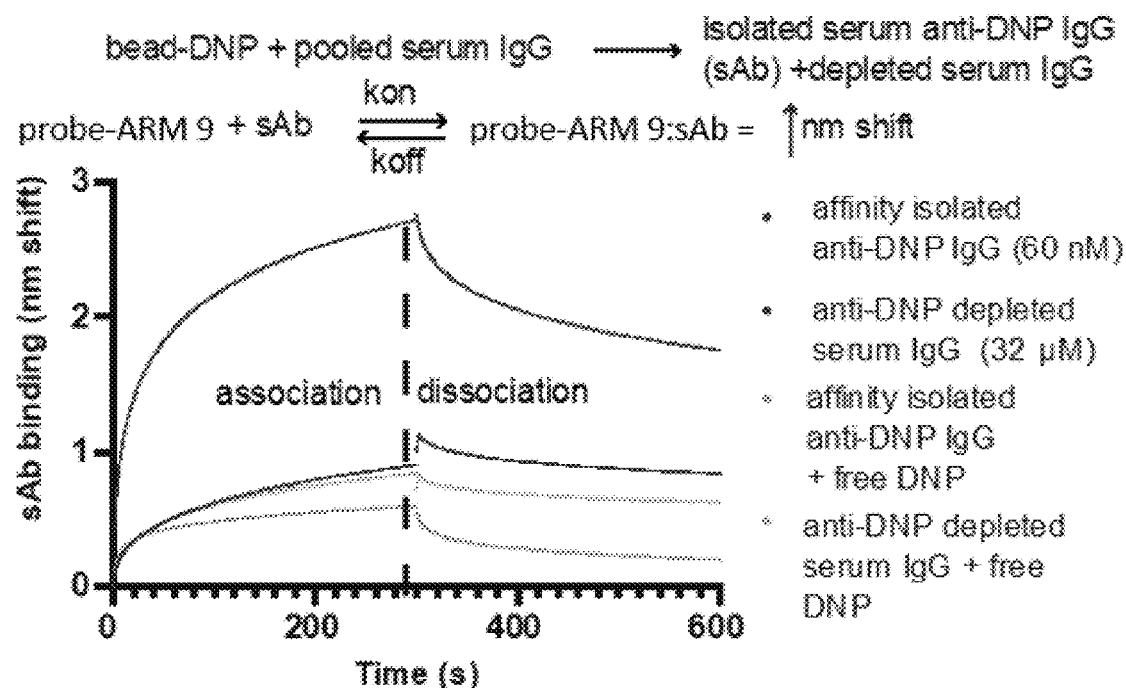
FIGS. 13A to 13D are graphs of antibody recruiting assays and evaluation of immune recognition of targets of an exemplary compound of the application and a comparative non-covalent compound using human serum anti-DNP IgG.
Figure 13B:
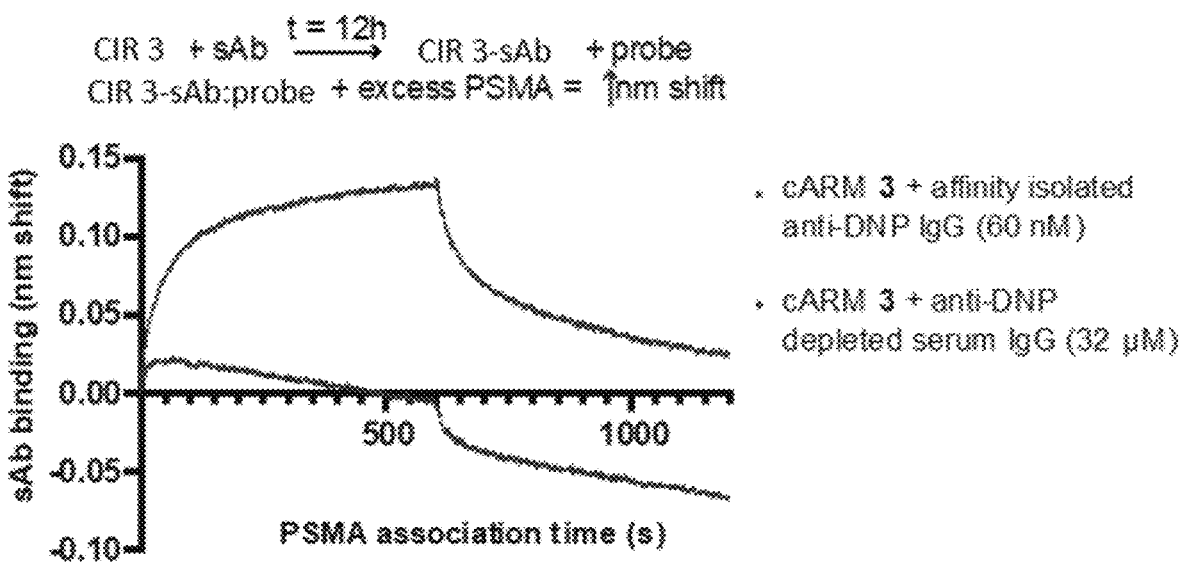

BLI analysis of the resulting enriched anti-DNP IgG solutions enabled estimation of the endogenous concentration in pooled human serum, which was found to be present at sub-saturating concentrations as hypothesized: [sAb]≈$10^{-8}$-$10^{-9}$ M, $k_{off(ARM:sAb)}$≈9.2×$10^{-3}$ $s^{-1}$, apparent $K_{d(Ab)}$≈4.6×$10^{-7}$ (FIG. 13A). The stability of ARM:sAb complexes is therefore similar to that determined for weaker binding human mAb. Controls for the successful isolation of bonafide polyclonal serum anti-DNP IgG, and its depletion from pooled human IgG samples (FIGS. 13A and C) are demonstrated by the following: i) samples of human IgG (32 µM) depleted of the endogenous anti-DNP IgG population via affinity isolation, show substantial reduction of antibody binding to probes immobilized with ARM 9, compared to dilute affinity enriched solutions of anti-DNP IgG (60 nM), ii) the antibody binding signal observed using 60 nM affinity enriched serum anti-DNP IgG samples is substantially reduced in the presence of free competitor DNP, iii) incubation of CIR 3 with the above 60 nM anti-DNP IgG enriched sample led to substantial covalent antibody labeling and resultant PSMA binding to Fc capture probes in BLI kinetic assays described in FIG. 9, and iv) covalent antibody labeling is substantially reduced when CIR 3 is incubated with concentrated pooled human IgG samples (32 µM) affinity depleted of the endogenous anti-DNP IgG population (FIG. 13B). These results further support the utility of the CIR strategy to selectively covalently recruit endogenous serum anti-DNP IgG in a therapeutically relevant human subject setting.

Figure 13C:
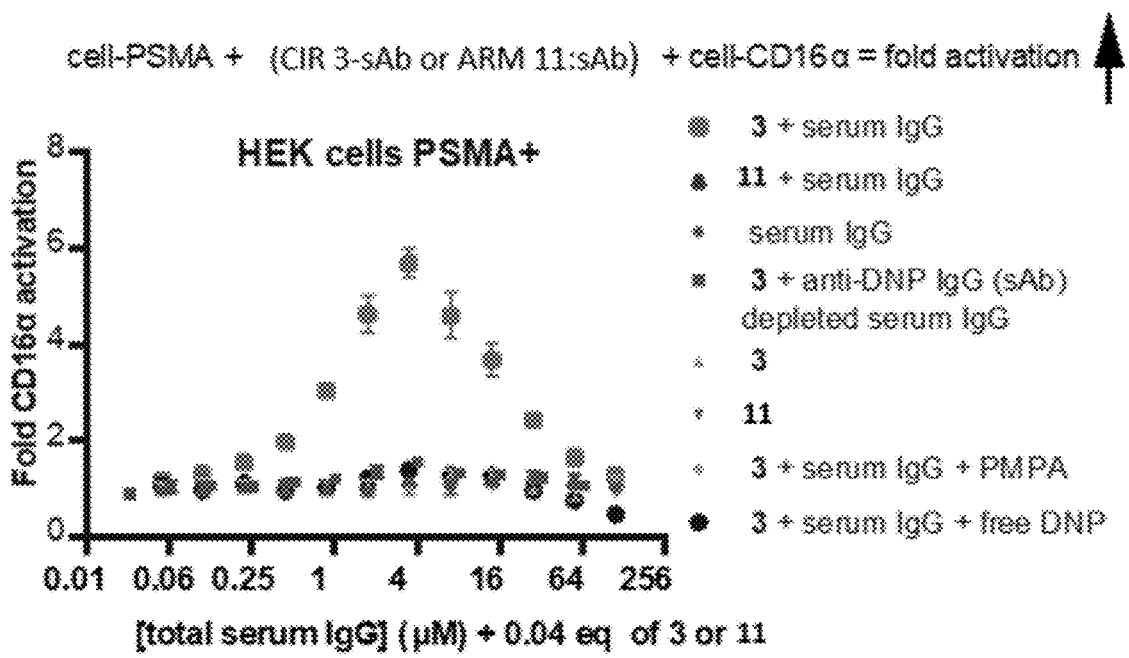
Figure 13D:
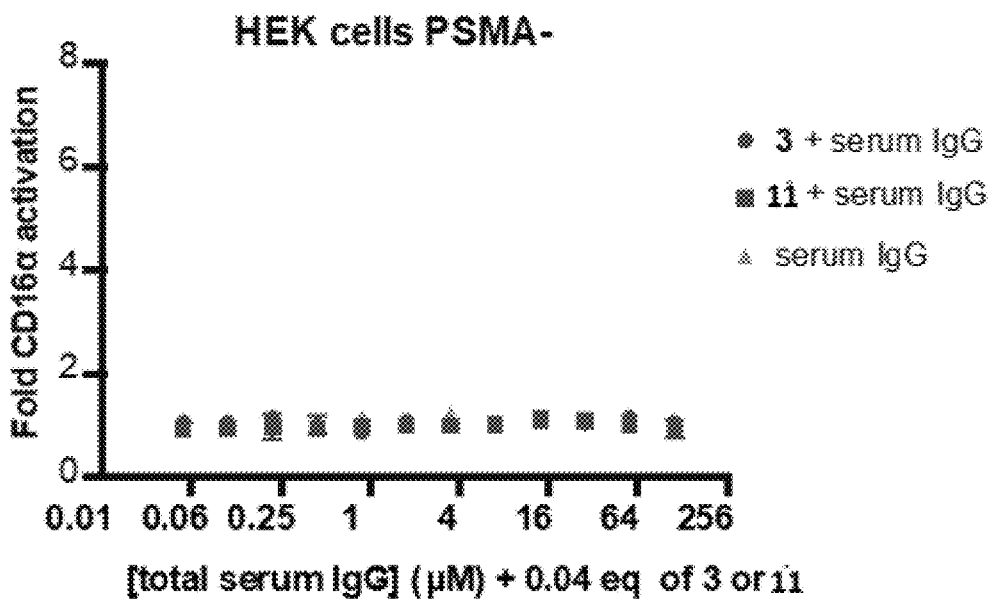

To determine if the covalent enhancement observed mAb is maintained, covalent recruitment of endogenous sAb in $CD_{16}\alpha$ activation assays was studied using a pan IgG solution (230 µM) isolated from pooled human serum containing an estimated native concentration of ~ 10 nM anti-DNP IgG. CIR 3 or ARM 11 was incubated with the pan IgG sample to form covalently stabilized (CIR-Ab) and non-covalent (ARM:Ab) complexes respectively, prior to dilution into target and immune cell solutions. Consistent with the results obtained using mAb and mmAb anti-DNP, CIR 3 covalent recruitment of sAb, within pooled serum IgG, mediated efficient $CD_{16}\alpha$ activation in sharp contrast to reversible recruitment via ARM 11 (FIG. 13C). In support of the selective covalent recruitment of a subpopulation of sAb, complete loss of immune cell receptor activation was observed when anti-DNP depleted IgG sample was used as an antibody source. Notably, this sample contains abundant IgG capable of potentially activating $CD_{16}\alpha$ if recruited to a target cell surface. Control experiments were performed confirming selective target PSMA binding and antibody recruitment. A complete loss of function was observed when experiments were repeated on isogenic control PSMA negative HEK cells (FIG. 13D), or free DNP competitor was added to the natural pooled IgG sample, blocking CIR binding and covalent recruitment of sAb. Taken together, the results of these studies demonstrate that ARM mediated target immune recognition is limited by the stability of ARM:Ab complexes, in the therapeutically relevant context of human serum anti-DNP antibody.

Discussion

Figure 14A:
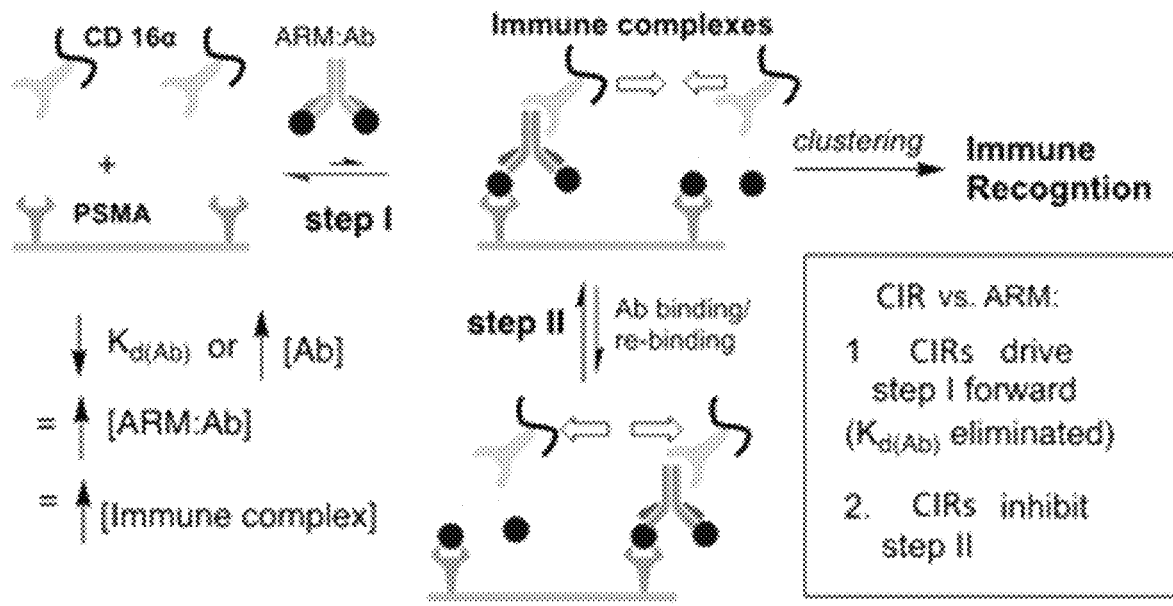
FIGS. 14A and 14B are schematic illustrations of embodiments of the application.
Figure 14B:
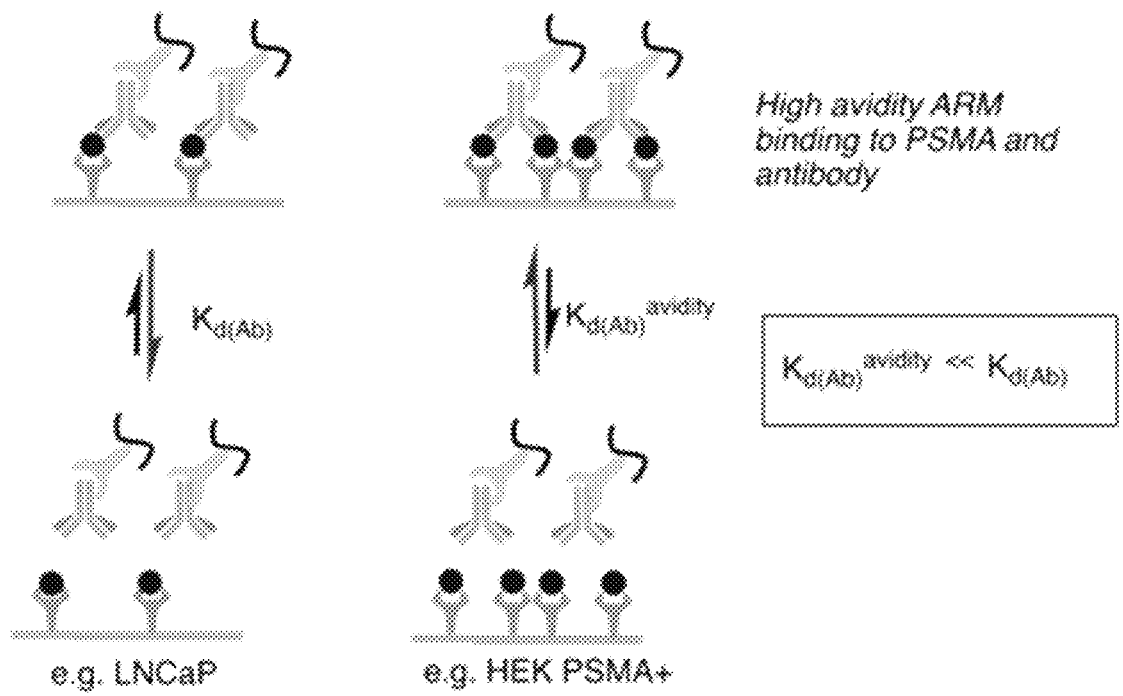

Without being limited by theory, FIG. 14 shows a proposed immune complex kinetic stability model of antibody dependent immune recognition of target cells, to explain origins of covalent enhancement. Specifically, FIG. 14A shows high concentrations of antibody favor formation of ARM:Ab complexes which drive formation of immune complexes (step 1). Rapid antibody dissociation/reassociation within these complexes attenuates immune receptor clustering (step 11). Darker and lighter antibodies depict antibody re-binding to different locations. White arrows depict efficient or non-efficient immune receptor clustering. Covalent antibody recruitment acts to both effectively increase [ARM:Ab] and to inhibit antibody re-binding. FIG. 14B shows high cancer protein expression (e.g. PSMA on HEK cells) enables high avidity binding of ARMs to both PSMA and antibody increasing apparent binding affinity in the presence of target cells. Lower cancer protein expression (e.g. PSMA on LNCaP) prevents high avidity binding interactions.

Without being limited by theory, the origins of the functional covalent enhancement observed herein, in the context of both macrophage ($CD_{64}$) and NK cell (CD16a) models of target immune recognition, is likely at least in part due to the enhanced recruitment of antibodies to target cancer receptors. Enhanced antibody recruitment enables increased engagement of immune cell receptors $CD_{64}$ or $CD_{16}\alpha$ to form "immune complexes" leading to a functional response (FIG. 14). Covalent antibody recruitment may be envisioned to enable a higher occupancy of cell surface PSMA sites with antibody at sub-saturating antibody concentrations $(([Ab]<10\times K_{d(Ab)})$. Under these conditions, non-covalent recruitment would be limited by the dissociation of ARM: Ab non-covalent complexes which is not possible with kinetically stabilized CIR-Ab complexes. Indeed, it was observed that CIRs can enhance antibody recruitment to target HEK cells relative to ARMs, in flow cytometry experiments at antibody concentrations below 40 nM of both mAb and mmAb (FIG. 12). Above these antibody concentrations, maximal antibody recruitment is achieved via both ARMs and CIRs, to occupy all possible PSMA sites with antibody. The data presented herein supports natural serum anti-DNP antibodies fall within a sub-saturating concentration and binding affinity regime and demonstrate CIRs exert a functional enhancement relative to ARMs. As such, in the therapeutically relevant context of subject serum, CIRs can achieve a functional enhancement by increasing antibody recruitment to cancer cells driving the formation of immune complexes (FIG. 14A, step I). Notably, antibody recruiting experiments could not be performed using sAb due to limited quantities that can be isolated from pooled human serum.

If CIRs only exert a functional enhancement relative to ARMs by increasing antibody recruitment to target cells, then this enhancement should cease as the concentration of antibody increases and ARMs eventually maximize antibody recruitment. Under these conditions, both CIRs and ARMs will form immune complexes with equal efficiency. Interestingly the results presented herein show this only to be the case in macrophage ($CD_{64}$) models of target immune recognition of HEK PSMA+ cell lines using higher affinity mmAb (FIG. 9D). Here, the CIR covalent enhancement was most significant at lower antibody concentrations, with ARM function increasing with antibody concentrations. In the context of lower affinity mAb, however, increasing antibody concentration only enabled a subtle increase in ARM mediated $CD_{64}$ immune function (FIG. 10D), that never approached the efficacy achieved using CIRs. This result is surprising as ARMs can maximize antibody recruitment by 40 nM mAb concentrations akin to CIRs (FIG. 12A). The lack of ARM function was even more pronounced in NK cell ($CD_{16}\alpha$) models of target immune recognition. Here ARMs were observed to completely lack function with both mAb or mmAb antibodies even beyond 200 nM antibody concentrations (FIGS. 9C and E and FIG. 10C), in sharp contrast to the robust efficacy achieved using CIRs. This result was surprising given the demonstrated ability of ARMs to maximally recruit antibodies to target cells akin to CIRs, and saturate all surface PSMA binding sites well below 200 nM anti-DNP antibody (FIG. 12). Notably, 200 nM antibody concentrations likely approach the upper limit of what can be found naturally in human serum in the absence of vaccination. Taken together, these results suggest target immune recognition is not only governed by the number of antibodies recruited to the target cell surface and number/concentration of immune complexes formed. It is proposed these results can be rationalized on the basis of covalent stabilization effects on immune receptor complexes themselves (FIG. 14A, step II).

Antibody dependent immune recognition of cancer cells minimally requires cell recruited antibodies to bind activation receptors like $CD_{16}\alpha$ (R) or $CD_{64}$ (R) to form reversible immune complexes (FIG. 14A). These immune complexes cluster (self-associate) to activate immune receptor signaling needed for function. This is why antibody dependent recognition mechanisms require a critical threshold density of recruited antibodies. As such, it is hypothesized that activation of receptor signaling is highly sensitive not only to the number but also to the kinetic stability/lifetime of immune complexes, and that immune complexes ideally remain intact long enough to enforce clustering and signalling. Covalent stabilization may enhance the kinetic stability of immune complexes by removing the ARM:antibody equilibrium. This would inhibit antibody dissociation/rebinding events that can occur within immune complexes that decrease the efficiency of $CD_{64}/CD_{16}\alpha$ receptor clustering (FIG. 14B, step II). The interaction between target cell recruited antibody and $CD_{16}\alpha$ is particularly weak compared to the other binding interactions within the immune complex ($K_{d(Ab:CD16)} \approx 10^{-6}$ M). Since ARM/CIR binding interaction for PSMA is strong ($K_{d(C)} \leq 10^{-8}$ M), the kinetic stability of immune complexes involving $CD_{16}\alpha$ and efficiency of $CD_{16}\alpha$ clustering may be highly sensitive to the ARM:Ab dissociation rate governed by $k_{off}$. When immune receptor affinity for the antibody Fc domain increases, such as the case for $CD_{64}$ ($K_{d(Ab:CD64)} \approx 10^{-8}$ M), the efficiency of receptor clustering may be less sensitive to ARM:Ab dissociation events, especially when Ab affinity for ARM is sufficiently high (e.g. mmAb, FIG. 9D). Without being limited by theory, this model of covalent functional enhancement can explain why the results of $CD_{64}$-based immune recognition assays are more congruent with flow cytometry antibody recruiting data compared to assays involving $CD_{16}\alpha$. This model also rectifies how CIRs confer a functional enhancement over ARMs even when both approaches achieve maximal antibody recruitment to target cells and form the same number of immune complexes.

Interestingly, in flow cytometry assays, target cell saturation with ARM:antibody complexes (mAb and mmAb) appeared at substantially lower antibody concentrations (40 nM) than predicted, based on the solution $K_d$Ab) values calculated for mAb and mmAb (Table 1). This suggests ARM apparent affinity for both anti-DNP IgG classes and the stability of ARM:Ab complexes in the presence of target cells, far exceeds what was determined in solution (FIG. 14B). This observation is consistent with high avidity binding to PSMA and anti-DNP. It is hypothesized that this is facilitated by a sufficiently high density of PSMA on the target surface that enables anti-DNP IgG to contact two cell bound ARM molecules simultaneously. Additional support of high avidity antibody binding ($K_{d(Ab)}^{avidity}$) to ARMs localized on the target cell surface, is the observation of a steep increase in MFI signal when a critical threshold fraction of cell surface PSMA receptors are occupied with ARM ([ARM]≈26 nM) in FIG. 12. The fact that non-covalent ARM:Ab complexes on target HEK cells fail to promote $CD_{16}\alpha$ activation despite being additionally avidity stabilized, suggests ARM:Ab complexes require exceptional kinetic stability to mediate natural killer cell ($CD_{16}\alpha$) driven target immune recognition. This would require significant medicinal chemistry efforts to increase ARM binding affinity for its target antibody to dramatically decrease the binding $k_{off}$.

Notably, in the context of lower PSMA expressing LNCaP cell lines, ARMs were largely unable to mediate target immune recognition ($CD_{64}$) at any antibody concentration tested in contrast to CIRs (FIG. 11). These results suggest lower PSMA expressing target cells inhibit high avidity antibody recruitment needed to sufficiently stabilize immune complexes critical for ARM function (FIG. 14B). In this scenario, the covalent enhancement may arise due to a combination of increased antibody recruitment and increased kinetic stabilization of immune complexes.

Results from the kinetic assay developed to characterize CIR second order kinetics data demonstrated that the CIR strategy can be used to efficiently form kinetically stable complexes (CIR-Ab), when anti-DNP antibodies are present at sub-saturating concentrations. The $k_{inact}/K_I$ values estimated for covalent modification of mAb ($\approx 1730$ M$^{-1}$ s$^{-1}$), which shares an ARM binding affinity similar to that determined for human serum anti-DNP sAb ($K_{d(Ab)} \approx 10^{-7}$ M), predict even as low as 10 nM concentrations of anti-DNP antibody in a subject's serum can be completely covalently labelled within in a few hours following I.V. administration of 500 nM CIR. As such CIR-Ab formation can occur at a rate competitive with ARM clearance rates in vivo ($t_{1/2} \approx$ hrs). Thus, in in vivo applications, the administration of excess CIR up to 1 μM concentrations, is not anticipated to lead to substantial off-target labeling. In kinetic BLI assays, high covalent reaction selectivity for the DNP hapten binding site on both mAb and mmAb was observed, even when a 20-fold excess (1.5 μM) of CIR 3 was used. Non-selective labeling at these excess CIR concentrations would have enabled PSMA binding to probes loaded with the human control antibody (FIG. 9A and FIG. 10A). Together with high labeling selectivity results for model anti-DNP spiked into 100% human serum, these kinetics data support the hypothesis that in in vivo applications, excess CIR can be administered to enhance antibody reaction kinetics if necessary, without sacrificing selectivity. Excess un-reacted CIR can be eliminated via clearance mechanisms to prevent autoinhibition, leaving stable covalent "CIR-Ab" complexes.

The results of the experiments presented herein illuminate key biological parameters and binding affinity requirements underlying ARM immunotherapeutic efficacy. It has been demonstrated that ARMs optimally have a minimal affinity for their target antibody in solution on the order of $K_{d(Ab)} \approx 10^{-8}$ M, and high avidity antibody recruitment to the target cell surface, to enable efficient immune recognition of cancer targets. It was also revealed that the stability of ARM:Ab complexes is a determinant for ARM function especially when natural killer cell activation receptors (CD 16a) are involved in target cell recognition. As suggested by the lack of function associated with even stable ARM: mmAb complexes, the magnitude of kinetic stability to enable ARM mediated NK cell function ($<k_{off} \approx 1.0 \times 10^{-3}$ s$^{-1}$ for ARM:mmAb), may be difficult to achieve through medicinal chemistry efforts aimed at enhancing ARM binding affinity for its target antibody. Without being limited by theory, the findings presented herein support a model for antibody dependent immune recognition where efficacy is directly dependent on both the concentration and kinetic stability of immune complexes themselves that enforce receptor clustering. As such, efforts to directly covalently recruit immune receptors themselves may lead to even greater functional enhancements, given the intrinsically limited binding affinity of natural antibodies for these receptors. It is further revealed that widely studied anti-DNP antibodies for use in synthetic tumor immunotherapy, naturally exist in human serum at sub-saturating concentrations well below the $K_{d(Ab)}$ and as such are likely to limit the maximal therapeutic efficacy achievable by ARMs. The CIR covalent stabilization strategy, however, enables ARMs to overcome these biological constraints enforced by the host to affect robust immune function. As such the CIR strategy shows promise as a tumor immunotherapeutic strategy, where CIR-Ab complexes can be efficiently formed and remain in circulation for several days hijacking the natural circulation times of serum antibodies. Non-covalent ARM:antibody complexes (ARM:Ab) however, are prone to dissociation that will be driven forward by the standard in vivo clearance of ARMs. Finally, CIRs represent a potentially general covalent strategy to enhance the function of proximity-inducing molecules in immunological settings where native species concentrations/affinities are limiting.

Figure 15:
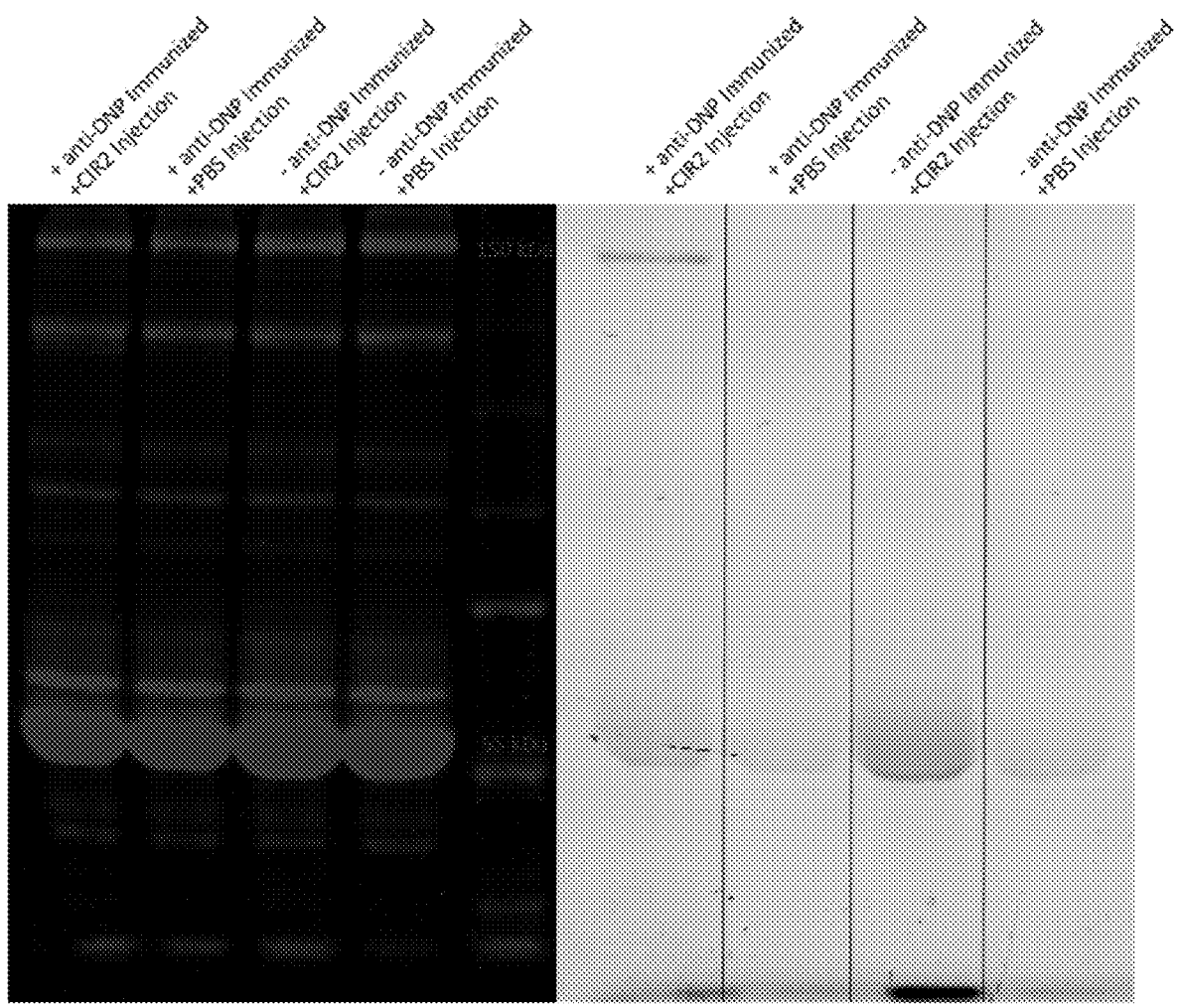
FIG. 15 shows results from in vivo administration of an exemplary compound of the application in mice via fluorescence imaging of SDS-PAGE.

Example 20: In Vivo Administration of CIRs to Selectively Label Anti-DNP Antibodies In vivo antibody recruitment of CIRs was evaluated by administration of the fluorescent derivative CIR 2 in mice using four different cage conditions with 5 mice per cage and monitoring by non-reducing SDS-PAGE. The four cage conditions were: 1) anti-DNP immunized+received CIR 2 injection, 2) anti-DNP immunized+received PBS injection, 3) not anti-DNP immunized+received CIR 2 injection, and 4) not anti-DNP immunized+received PBS injection. Mice that received the CIR 2 injection received 200 µL of 6.58 µM, giving a final concentration in the mice of 800 nM (10× above $K_d$). Blood was taken from the mice after about 6 hr. Serum was isolated from the blood, diluted to 10% in PBS and run on a 10% SDS-PAGE gel to image antibody labelling. FIG. 15 shows results from in vivo administration of CIR 2 or PBS in mice via fluorescence imaging of SDS-PAGE, with cage conditions 1-4 corresponding to Lanes 1-4 (Lane 5=marker) of the gel.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

All publications, patents and patent applications are herein incorporated by reference in their entirety to the same extent as if each individual publication, patent or patent application was specifically and individually indicated to be incorporated by reference in its entirety. Where a term in the present disclosure is found to be defined differently in a document incorporated herein by reference, the definition provided herein is to serve as the definition for the term.

FULL CITATIONS FOR DOCUMENTS REFERENCED IN THE APPLICATION i. Y. Lu, P. S. Low, Folate targeting of haptens to cancer cell surfaces mediates immunotherapy of syngeneic murine tumors. *Cancer immunology, immunotherapy: CII* 51, 153-162 (2002); published online EpubMay (10.1007/s00262-002-0266-6); C. Rader, S. C. Sinha, M. Popkov, R. A. Lerner, C. F. Barbas, 3rd, Chemically programmed monoclonal antibodies for cancer therapy: adaptor immunotherapy based on a covalent antibody catalyst. *Proceedings of the National Academy of Sciences of the United States of America* 100, 5396-5400 (2003); published online EpubApr 29 (10.1073/pnas.0931308100); C. B. Carlson, P. Mowery, R. M. Owen, E. C. Dykhuizen, L. L. Kiessling, Selective tumor cell targeting using low-affinity, multivalent interactions. *ACS chemical biology* 2, 119-127 (2007); published online EpubFeb 20 (10.1021/cb6003788); R. P. Murelli, A. X. Zhang, J. Michel, W. L. Jorgensen, D. A. Spiegel, Chemical control over immune recognition: a class of antibody-recruiting small molecules that target prostate cancer. *Journal of the American Chemical Society* 131, 17090-17092 (2009); published online EpubDec 02 (10.1021/ja906844e); A. Dubrovska, C. Kim, J. Elliott, W. Shen, T. H. Kuo, D. I. Koo, C. Li, T. Tuntland, J. Chang, T. Groessl, X. Wu, V. Gorney, T. Ramirez-Montagut, D. A. Spiegel, C. Y. Cho, P. G. Schultz, A chemically induced vaccine strategy for prostate cancer. *ACS chemical biology* 6, 1223-1231 (2011); published online EpubNov 18 (10.1021/cb200222 s); R. T. Sheridan, J. Hudon, J. A. Hank, P. M. Sondel, L. L. Kiessling, Rhamnose glycoconjugates for the recruitment of endogenous anti-carbohydrate antibodies to tumor cells. *Chembiochem: a European journal of chemical biology* 15, 1393-1398 (2014); published online EpubJul 07 (10.1002/cbic.201402019); A. F. Rullo, K. J. Fitzgerald, V. Muthusamy, M. Liu, C. Yuan, M. Huang, M. Kim, A. E. Cho, D. A. Spiegel, Re-engineering the Immune Response to Metastatic Cancer: Antibody-Recruiting Small Molecules Targeting the Urokinase Receptor. *Angewandte Chemie* 55, 3642-3646 (2016); published online EpubMar 07 (10.1002/anie.201510866); Y Lu, P. S. Low, Targeted immunotherapy of cancer: development of antibody-induced cellular immunity. *The Journal of pharmacy and pharmacology* 55, 163-167 (2003; C. G. Parker, R. A. Domaoal, K. S. Anderson, D. A. Spiegel, An antibody-recruiting small molecule that targets HIV gp120. *Journal of the American Chemical Society* 131, 16392-16394 (2009); published online EpubNov 18 (10.1021/ja9057647); C. E. Jakobsche, P. J. McEnaney, A. X. Zhang, D. A. Spiegel, Reprogramming urokinase into an antibody-recruiting anticancer agent. *ACS chemical biology* 7, 316-321 (2012); published online EpubFeb 17 (10.1021/cb200374e).

ii. K. Akiyama, S. Ebihara, A. Yada, K. Matsumura, S. Aiba, T. Nukiwa, T. Takai, Targeting apoptotic tumor cells to Fc gamma R provides efficient and versatile vaccination against tumors by dendritic cells. *Journal of immunology* 170, 1641-1648 (2003); published online EpubFeb. 15, 2003; Y. Lu, E. Sega, C. P. Leamon, P. S. Low, Folate receptor-targeted immunotherapy of cancer: mechanism and therapeutic potential. *Advanced drug delivery reviews* 56, 1161-1176 (2004); published online EpubApr 29 (10.1016/j.addr.2004.01.009).

iii. E. F. Douglass, Jr., C. J. Miller, G. Sparer, H. Shapiro, D. A. Spiegel, A comprehensive mathematical model for three-body binding equilibria. *Journal of the American Chemical Society* 135, 6092-6099 (2013); published online EpubApr 24 (10.1021/ja311795d).

iv. V. Huynh, A. H. Jesmer, M. M. Shoaib, A. D. D'Angelo, A. F. Rullo, R. G. Wylie, Improved Efficacy of Antibody Cancer Immunotherapeutics through Local and Sustained Delivery. *Chembiochem: a European journal of chemical biology* 20, 747-753 (2019); published online EpubMar 15 (10.1002/cbic.201800579).

The invention claimed is:

1. A compound of Formula I or a pharmaceutically acceptable salt and/or solvate thereof:

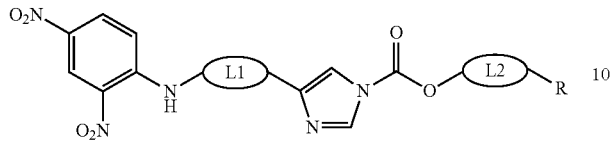

I wherein

L¹ and L² are, independently, linker groups selected from $C_{1-20}$ alkylene, optionally interrupted by triazolyl and/or one or more heteromoieties selected from O, S, S(O), $SO_2$, $OSO_2$, $SO_2O$, $OSO_2O$, $NR^8$, C(O), NHC(O) and C(O)NH, wherein $R^8$ is H or $C_{1-4}$alkyl;

and

R is a target binding domain (TBD), wherein the TBD is (1)

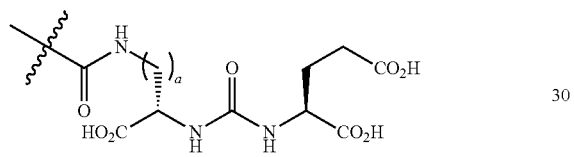

wherein a is an integer from 0 to 10, 1 to 15, 1 to 10, 1 to 8, or 1, 2, 3, 4, 5 or 6;

(2)

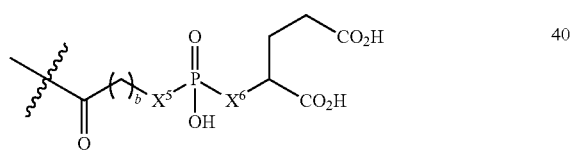

wherein $X^5$ and $X^6$ are independently $CH_2$, O, NH or S; and b is an integer from 0 to 10, 1 to 15, 1 to 10, 1 to 8, or 1, 2, 3, 4, 5 or 6;

(3)

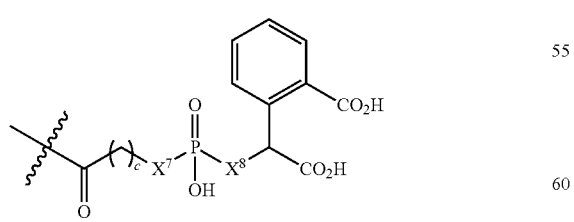

wherein $X^7$ and $X^8$ are independently $CH_2$, O, NH or S; and c is an integer from 0 to 10, 1 to 15, 1 to 10, 1 to 8, or 1, 2, 3, 4, 5 or 6;

(4)

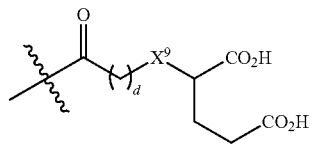

wherein $X^9$ is O, $CH_2$, $NR^5$, S(O), $SO_2$, $SO_2O$, $OSO_2$ or $OSO_2O$;

$R^5$ is H, $C_{1-4}$alkyl or $C(O)C_{1-4}$alkyl; and d is an integer from 0 to 10, 1 to 15, 1 to 10, 1 to 8, or 1, 2, 3, 4, 5 or 6; or (5) biotin or a biotin analog:

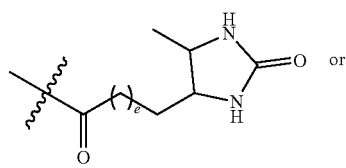

or

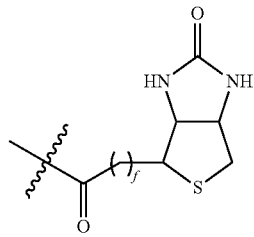

wherein e and f are, independently, an integer from 0 to 10, 1 to 15, 1 to 10, 1 to 8, or 1, 2, 3, 4, 5 or 6.

2. The compound of claim 1, wherein L¹ and L² are independently, a group having the following structure:

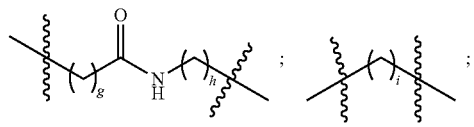

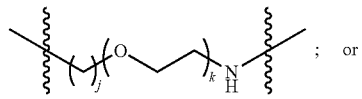

; or

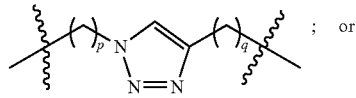

; or

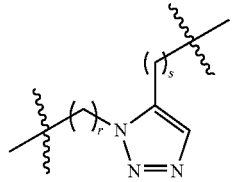

wherein, g, h, i, j, k, p, q, r and s are, independently, 1, 2, 3, 4, 5, 6, 7, 8, 9 or 10.

3. The compound of claim 1 which is:

| Compound I.D. | Example # | Structure |
|---|---|---|
| I-1 CIR 1 | 1 | *(structure)* |
| 1-3 CIR 3 | 3 | *(structure)* |
| 1-4 CIR 4 | 4 | *(structure)* |
| 1-5 CIR 5 | 5 | *(structure)* | or a pharmaceutically acceptable salt and/or solvate thereof.

4. A composition comprising the compound of claim 1 and a carrier.

5. A method for recruiting an antibody for immunotherapy, either in a biological sample or in a subject, comprising administering an effective amount of the compound of claim 1 to the biological sample or subject.

6. A method for recruiting an antibody and targeting a cell for provoking an immune response to the cell, either in a biological sample or in a subject, comprising administering an effective amount of the compound of claim 1 to the biological sample or the subject.

7. A method for binding tumor antigens in a cell, either in a biological sample or in a subject, comprising administering an effective amount of the compound of claim 1 to the biological sample or the subject.

8. A method for provoking cellular phagocytosis of a target cell, either in a biological sample or in a subject, comprising administering an effective amount of the compound of claim 1 to the biological sample or the subject.

9. The compound of claim 1, wherein a, b, c, d, e and f are, independently, 1, 2, 3, 4, 5 or 6.

10. The compound of claim 1, wherein a, b, c, d, e and f are, independently, 2, 3, or 4.

11. The compound of claim 1, wherein a, b, c, d, e and f are 4.

12. The compound of claim 1, wherein the TBD is one of the following groups:

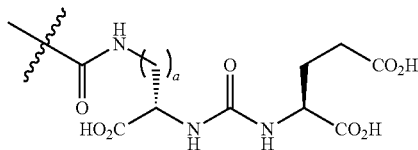

wherein a is 1, 2, 3, 4, 5 or 6; or

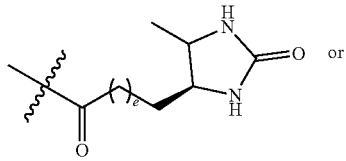

or

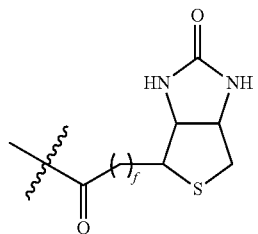

wherein e and f are, independently, is 1, 2, 3, 4, 5 or 6.

13. The compound of claim 1, wherein the TBD is

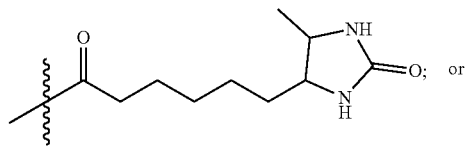

or

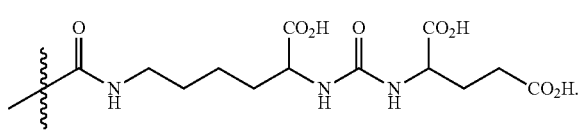

14. The compound of claim 2, wherein j is 2 and k is 3.

15. The compound of claim 2, wherein g is 1 and h is 2.

* * * * *